(12) United States Patent
Klein et al.

(10) Patent No.: US 12,241,851 B2
(45) Date of Patent: Mar. 4, 2025

(54) SYSTEM AND METHOD FOR PROCESSING ANALYTE SIGNALS IN GMR-BASED DETECTION OF BIOMARKERS

(71) Applicant: Zepto Life Technology, Inc., St. Paul, MN (US)

(72) Inventors: Todd Michael Klein, Wayzata, MN (US); Michael Monroe Reinhart Sandstedt, Minneapolis, MN (US); Keping Song, Lauderdale, MN (US)

(73) Assignee: Zepto Life Technology, Inc., St. Paul, MN (US)

( * ) Notice: Subject to any disclaimer, the term of this patent is extended or adjusted under 35 U.S.C. 154(b) by 741 days.

(21) Appl. No.: 15/734,395

(22) PCT Filed: Jul. 26, 2019

(86) PCT No.: PCT/US2019/043791
§ 371 (c)(1),
(2) Date: Dec. 2, 2020

(87) PCT Pub. No.: WO2020/023934
PCT Pub. Date: Jan. 30, 2020

(65) Prior Publication Data
US 2021/0172927 A1    Jun. 10, 2021

Related U.S. Application Data

(60) Provisional application No. 62/711,396, filed on Jul. 27, 2018.

(51) Int. Cl.
*G01N 27/12* (2006.01)
*B01L 3/00* (2006.01)
(Continued)

(52) U.S. Cl.
CPC ........ *G01N 27/12* (2013.01); *B01L 3/502715* (2013.01); *B01L 3/50273* (2013.01);
(Continued)

(58) Field of Classification Search
CPC ................. G01N 27/12; G01N 27/745; G01N 33/54306; G01R 33/093; G01R 33/1269;
(Continued)

(56) References Cited

U.S. PATENT DOCUMENTS

| | | |
|---|---|---|
| 5,371,469 A | 12/1994 | Anderson |
| 5,646,001 A | 7/1997 | Terstappen et al. |

(Continued)

FOREIGN PATENT DOCUMENTS

| | | |
|---|---|---|
| AU | 2023200506 | 3/2023 |
| CN | 1538386 A | 10/2004 |

(Continued)

OTHER PUBLICATIONS

Mak, Andy C., et al. "Sensitive giant magnetoresistive-based immunoassay for multiplex mycotoxin detection." Biosensors and Bioelectronics 25.7 (2010): 1635-1639. (Year: 2010).*

(Continued)

*Primary Examiner* — Russell S Negin
*Assistant Examiner* — Guozhen Liu
(74) *Attorney, Agent, or Firm* — Schwegman Lundberg & Woessner, P.A.

(57) ABSTRACT

A signal processing system used for GMR-based detection of a target analyte in a sample under test, comprising: a measurement circuit configuration unit configured to build a GMR sensor measurement circuit by routing in at least one GMR sensor, and to build a reference resistor measurement circuit by routing in at least one reference resistor; a magnetic field excitation unit configured to apply an AC magnetic field of frequency $\omega_2$ to the at least one GMR sensor;

(Continued)

a carrier signal applying unit configured to apply a carrier signal of frequency $\omega_1$ to the GMR sensor measurement circuit, and apply carrier signals of frequency $\omega_1$, $\omega_1+\omega_2$, and $\omega_1-\omega_2$ to the reference resistor measurement circuit; a measurement signal pick-up unit coupled to the measurement circuits, configured to collect reference resistor measurement signals from the reference resistor measurement circuit and GMR sensor measurement signals from the GMR sensor measurement circuit; and a phase sensitive solution unit coupled to the measurement signal pick-up unit, configured to analytically solve for resistance change of the at least one GMR sensor based on both the reference resistor measurement signals from the reference resistor measurement circuit and the GMR sensor measurement signals from the GMR sensor measurement circuit.

24 Claims, 38 Drawing Sheets

(51) Int. Cl.
G01N 27/74 (2006.01)
G01N 33/18 (2006.01)
G01N 33/487 (2006.01)
G01N 33/49 (2006.01)
G01N 33/493 (2006.01)
G01N 33/543 (2006.01)
G01R 33/09 (2006.01)
G01R 33/12 (2006.01)

(52) U.S. Cl.
CPC .............. B01L 3/567 (2013.01); G01N 27/74 (2013.01); G01N 27/745 (2013.01); G01N 33/1813 (2013.01); G01N 33/48707 (2013.01); G01N 33/49 (2013.01); G01N 33/493 (2013.01); G01N 33/54306 (2013.01); G01R 33/093 (2013.01); G01R 33/1269 (2013.01); G01R 33/1276 (2013.01); B01L 2200/026 (2013.01); B01L 2200/027 (2013.01); B01L 2200/04 (2013.01); B01L 2200/0684 (2013.01); B01L 2200/16 (2013.01); B01L 2300/025 (2013.01); B01L 2300/0663 (2013.01); B01L 2300/0681 (2013.01); B01L 2300/0816 (2013.01); B01L 2300/0819 (2013.01); B01L 2300/0883 (2013.01); B01L 2300/0887 (2013.01); B01L 2300/123 (2013.01); B01L 2300/14 (2013.01); B01L 2400/043 (2013.01); B01L 2400/0487 (2013.01); B01L 2400/06 (2013.01)

(58) Field of Classification Search
CPC ................ G01R 33/1276; G01R 33/09; B01L 2400/043
USPC ........................................................ 702/19
See application file for complete search history.

(56) References Cited

U.S. PATENT DOCUMENTS

| 5,981,297 | A | 11/1999 | Baselt |
| 6,426,043 | B1 | 7/2002 | Cohen et al. |
| 6,437,563 | B1 | 8/2002 | Simmonds et al. |
| 7,910,074 | B2 | 3/2011 | Li et al. |
| 8,889,760 | B2 | 11/2014 | Kurdyumov et al. |
| 9,487,663 | B2 | 11/2016 | Kurdyumov et al. |
| 9,994,721 | B2 | 6/2018 | Kurdyumov et al. |
| 10,253,193 | B2 | 4/2019 | Kurdyumov et al. |
| 10,315,987 | B2 | 6/2019 | Kurdyumov |
| 10,688,493 | B2 | 6/2020 | Kim et al. |
| 11,579,107 | B2 | 2/2023 | Klein et al. |
| 11,639,908 | B2 | 5/2023 | Klein et al. |
| 2002/0119470 | A1 | 8/2002 | Nerenberg et al. |
| 2003/0044323 | A1 | 3/2003 | Diamond et al. |
| 2003/0153092 | A1 | 8/2003 | Skinner et al. |
| 2005/0085619 | A1 | 4/2005 | Wilson |
| 2006/0115514 | A1 | 6/2006 | Gengrinovitch |
| 2008/0129286 | A1 | 6/2008 | Kahlman et al. |
| 2008/0190735 | A1 | 8/2008 | Luoma |
| 2008/0238411 | A1 | 10/2008 | Kahlman et al. |
| 2008/0246471 | A1 | 10/2008 | Kahlman et al. |
| 2008/0278156 | A1 | 11/2008 | De Boer |
| 2008/0284419 | A1 | 11/2008 | Ikeda |
| 2008/0309329 | A1 | 12/2008 | Kahlman et al. |
| 2009/0066318 | A1 | 3/2009 | Kahlman et al. |
| 2009/0130745 | A1 | 5/2009 | Williams et al. |
| 2009/0163785 | A1 | 6/2009 | Nelson |
| 2009/0184706 | A1 | 7/2009 | Duric et al. |
| 2010/0259250 | A1 | 10/2010 | Kahlman |
| 2010/0267169 | A1 | 10/2010 | Hajimiri et al. |
| 2010/0323355 | A1 | 12/2010 | Dittmer |
| 2010/0324828 | A1 | 12/2010 | Kahlman et al. |
| 2011/0005932 | A1 | 1/2011 | Jovanovich et al. |
| 2011/0117676 | A1 | 5/2011 | Ikeda et al. |
| 2011/0241664 | A1 | 10/2011 | Zhang |
| 2012/0115214 | A1 | 5/2012 | Battrell et al. |
| 2012/0231971 | A1 | 9/2012 | Choi et al. |
| 2012/0315621 | A1 | 12/2012 | Lu et al. |
| 2013/0102489 | A1 | 4/2013 | Osterfeld et al. |
| 2013/0130262 | A1 | 5/2013 | Battrell et al. |
| 2013/0331298 | A1 | 12/2013 | Rea |
| 2013/0343966 | A1 | 12/2013 | Medoro et al. |
| 2014/0120523 | A1 | 5/2014 | Lowery, Jr. et al. |
| 2014/0178900 | A1 | 6/2014 | Jung et al. |
| 2014/0248612 | A1 | 9/2014 | Princen et al. |
| 2014/0292318 | A1 | 10/2014 | Wang et al. |
| 2015/0136604 | A1 | 5/2015 | Nielsen et al. |
| 2015/0197784 | A1 | 7/2015 | Williams et al. |
| 2015/0198594 | A1 | 7/2015 | Williams et al. |
| 2015/0338427 | A1 | 11/2015 | Pollack et al. |
| 2016/0011182 | A1 | 1/2016 | Qiu |
| 2016/0025756 | A1 | 1/2016 | Pollack et al. |
| 2016/0090633 | A1 | 3/2016 | Platero et al. |
| 2016/0193603 | A1 | 7/2016 | Battrell et al. |
| 2016/0194691 | A1 | 7/2016 | Powell et al. |
| 2016/0209405 | A1 | 7/2016 | Wang et al. |
| 2017/0097337 | A1 | 4/2017 | Shultz et al. |
| 2017/0113221 | A1 | 4/2017 | Hoffman et al. |
| 2017/0113222 | A1 | 4/2017 | Grummitt et al. |
| 2017/0241971 | A1 | 8/2017 | Liu et al. |
| 2017/0260567 | A1 | 9/2017 | Selden et al. |
| 2017/0312751 | A1 | 11/2017 | Glezer et al. |
| 2017/0356056 | A1 | 12/2017 | Powell et al. |
| 2018/0021783 | A1 | 1/2018 | Arlett et al. |
| 2018/0067094 | A1 | 3/2018 | Sinha et al. |
| 2018/0099278 | A1 | 4/2018 | Niemeyer et al. |
| 2018/0100869 | A1 | 4/2018 | Niemeyer et al. |
| 2018/0299407 | A1 | 10/2018 | Haratani et al. |
| 2018/0314046 | A1 | 11/2018 | Sakurai et al. |
| 2019/0283025 | A1 | 9/2019 | Brenk et al. |
| 2021/0131989 | A1 | 5/2021 | Klein et al. |
| 2021/0138462 | A1 | 5/2021 | Klein et al. |
| 2021/0370289 | A1 | 12/2021 | Klein et al. |
| 2023/0102733 | A1 | 3/2023 | Klein et al. |

FOREIGN PATENT DOCUMENTS

| CN | 101563610 | A | 10/2009 |
| CN | 101578529 | A | 11/2009 |
| CN | 101632018 | A | 1/2010 |
| CN | 101855366 | A | 10/2010 |
| CN | 103078520 | A | 5/2013 |
| CN | 103260513 | A | 8/2013 |
| CN | 103698320 | A | 4/2014 |
| CN | 104530413 | A | 4/2015 |
| CN | 104707674 | A | 6/2015 |
| CN | 105163661 | A | 12/2015 |
| CN | 105529710 | A | 4/2016 |

(56) References Cited

FOREIGN PATENT DOCUMENTS

| | | |
|---|---|---|
| CN | 106249021 A | 12/2016 |
| CN | 107430140 A | 12/2017 |
| CN | 107513577 A | 12/2017 |
| CN | 107690581 A | 2/2018 |
| CN | 107810060 A | 3/2018 |
| CN | 109563199 A | 4/2019 |
| CN | 111065923 | 4/2020 |
| CN | 110959118 | 8/2024 |
| EP | 1936350 A1 | 6/2008 |
| EP | 3324189 A1 | 5/2018 |
| EP | 4130749 | 2/2023 |
| GB | 1278311 A | 6/1972 |
| IN | 534863 | 4/2024 |
| JP | 2005180921 A | 7/2005 |
| JP | 2008511842 A | 4/2008 |
| JP | 2008522151 A | 6/2008 |
| JP | 2008544246 A | 12/2008 |
| JP | 2009008475 A | 1/2009 |
| JP | 2009511860 A | 3/2009 |
| JP | 2009511895 A | 3/2009 |
| JP | 2009530602 A | 8/2009 |
| JP | 2009-249512 A | 10/2009 |
| JP | 2009-250926 A | 10/2009 |
| JP | 2009236933 A | 10/2009 |
| JP | 2009539098 A | 11/2009 |
| JP | 2010500547 A | 1/2010 |
| JP | 2011503585 A | 1/2011 |
| JP | 2011-221017 A | 11/2011 |
| JP | 2012-513586 A | 6/2012 |
| JP | 2012-516455 A | 7/2012 |
| JP | 2013-518289 A | 5/2013 |
| JP | 2016-509206 A | 3/2016 |
| JP | 2016512339 A | 4/2016 |
| JP | 2016-534333 A | 11/2016 |
| JP | 2017-520239 A | 7/2017 |
| JP | 2018507403 A | 3/2018 |
| JP | WO2017082227 A1 | 8/2018 |
| JP | 2018525980 A | 9/2018 |
| JP | 2019533808 A | 11/2019 |
| JP | 7410912 B2 | 12/2023 |
| KR | 101304323 B1 | 9/2013 |
| KR | 10-2016-0080112 A | 7/2016 |
| WO | WO-03054523 A2 | 7/2003 |
| WO | WO-2005016115 A2 | 2/2005 |
| WO | 2006059270 A2 | 6/2006 |
| WO | 2007042959 A2 | 4/2007 |
| WO | 2007092909 A2 | 8/2007 |
| WO | 2008047533 A1 | 4/2008 |
| WO | 2008101196 A1 | 8/2008 |
| WO | 2009024922 A2 | 2/2009 |
| WO | WO-2009039437 A1 | 3/2009 |
| WO | 2012085884 A1 | 6/2012 |
| WO | WO-2016035197 A1 | 3/2016 |
| WO | 2016124907 A1 | 8/2016 |
| WO | WO-2017030999 A1 | 2/2017 |
| WO | WO-2017170238 A1 | 10/2017 |
| WO | 2018053501 A1 | 3/2018 |
| WO | 2018057647 A1 | 3/2018 |
| WO | WO-2020023903 A1 | 1/2020 |
| WO | WO-2020023916 A1 | 1/2020 |
| WO | WO-2020023924 A1 | 1/2020 |
| WO | WO-2020023934 A1 | 1/2020 |

OTHER PUBLICATIONS

Office Action mailed Oct. 20, 2022 in U.S. Appl. No. 16/770,195.
International Search Report and Written Opinion mailed Nov. 15, 2019 in International Application PCT/US2019/043766.
International Preliminary Report on Patentability mailed Feb. 11, 2021 in International Application PCT/US2019/043766.
International Preliminary Report on Patentability mailed Feb. 11, 2021 in International Application PCT/US2019/043753.
International Search Report and Written Opinion mailed Nov. 13, 2019 in International Application PCT/US2019/043720.
International Preliminary Report on Patentability mailed Feb. 11, 2021 in International Application PCT/US2019/043720.
International Search Report and Written Opinion mailed Nov. 13, 2019 in International Application PCT/US2019/043791.
International Preliminary Report on Patentability mailed Feb. 11, 2021 in International Application PCT/US2019/043791.
Office Action issued Feb. 2, 2021 in Japanese Application 2019-560695.
Office Action issued Feb. 2, 2021 in Japanese Application 2019-560691.
Extended European Search Report issued Mar. 15, 2021 in European Application 19816192.9.
International Search Report and Written Opinion mailed May 8, 2019 in International Application PCT/US2019/021837.
International Preliminary Report on Patentability issued Sep. 22, 2020 in International Application PCT/US2019/021837.
Office Action mailed Oct. 4, 2022 in Japanese Patent Application No. 2021-143806.
Extended European Search Report issued Apr. 21, 2021 in European Application 19816193.7.
Office Action issued Apr. 27, 2021 in Japanese Application 2019-560705.
Office Action issued May 18, 2021 in Japanese Application 2019-560698.
Notice of Allowance mailed May 18, 2021 in Japanese Application 2019-560695.
Supplementary European Search Report issued Jan. 5, 2022 in EP Application No. 19816194.5.
Teh et al: "Highly sensitive and selective detection of Pb 2+ ions using a novel and simple DNAzyme-based quartz crystal microbalance with dissipation biosensor", Analyst, vol. i 39, No. 20, Jan. 1, 2014, pp. 5170-5175.
Han et al: "CMOS Integrated DNA Microarray Based on GMR Sensors", Electron Devices Meeting, 2006. IEDM '06. International, IEEE, PI, Dec. 1, 2006, pp. 1-4.
Han et al: "Magnetic Nanotechnology for Biodetection", Journal of the Association for Laboratory Automation, Elsevier, vol. 15, No. 2, Apr. 1, 2010, pp. 93-98.
Yu et al: "Giant Magnetoresistive Biosensors for Molecular Diagnosis: SurfaceChemistry and Assay Development", SPIE, PO Box 10 Bellingham WA 98227-0010 USA, vol. 7035 , pp. 1-9.
Huo et al: "A Novel High-Sensitivity Cardiac Multibiomarker Detection System Based on Microfluidic Chip and GMR Sensors", IEEE Transactions on Magnetics, IEEE Service Center, New York, NY, US, vol. 51, No. 11, Nov. 1, 2015 (Nov. 1, 2015), pp. 1-4.
Wu et al: "Comparison of Hydroxylated Print Additives on Antibody Microarray Performance", Journal of Proteome Research, vol. 5, No. ii, Oct. 19, 2006, pp. 2956-2965.
Chu et al: "Bioconjugated Magnetic Nanoparticles for the Detection of Bacteria", Journal of Biomedical Nanotechnology, American Scientific Publishers, US, vol. 9, No. 12, Jan. 1, 2013.
Gaster et al: "Matrix-insensitive protein assays push the limits of biosensors in medicine", Nature Medicine, Oct. 11, 2009, pp. 1-7.
McGhee et al: "DNAzyme sensors for detection of metal ions in the environment and imaging them in living cells", Current Opinion in Biotechnology, London, GB, vol. 45, Apr. 28, 2017, pp. 191-2001.
Wang et al: "Surface Modification for Protein and DNA null Immobilization onto GMR Biosensor", IEEE Transactions on Magnetics, IEEE Service Center, New York, NY, US, vol. 49, No. 1, Jan. 1, 2013 (Jan. 1, 2013), pp. 296-299.
Huo et al: "A novel high-sensitivity cardiac multi-biomarkers detecting system based on microfluidic chip and GMR sensor", 2015 IEEE Magnetics Conference (INTERMAG), IEEE, May 11, 2015 p. 1.
Office Action issued Feb. 23, 2022 in Canadian Patent Application No. 3,106,680.
Penultimate Official Action issued Mar. 17, 2023 in Japanese Patent Application No. 2021-170183.
Office Action issued Mar. 18, 2022 in Canadian Patent Application No. 3,106,320.
Han et al., "A Novel Zero-Drift Detection Method for Highly Sensitive GMR Biochips", IEEE Transactions on Magnetics, IEEE, USA, vol. 42, No. 10, Oct. 1, 2006, pp. 3560-3562.

(56) References Cited

OTHER PUBLICATIONS

First Office Action issued on Sep. 28, 2023 in Chinese Application No. 201980032488.7.
English Translation of Japanese Patent Application No. 2021-170183 Notice of Rejection mailed Sep. 25, 2023.
English Translation of Japanese Patent Application No. 2021-170183 Denial of Entry of Amendment mailed Sep. 25, 2023.
Son et al., "Preparation and Properties of PEG-Modified PHEMA Hydrogel and the Morphological Effect", Macromolecular Research, 2006, pp. 394-399, vol. 14, No. 3, Sungkyunkwan University, Suwon, Gyeonggi, Korea.
Quinn et al., "Photo-crosslinked copolymers of 2-hydroxyethyl methacrylate, poly(ethylene glycol) tetra-acrylate and ethylene dimethacrylate for improving biocompatibility of biosensors", Biomaterials, 1995, pp. 389-396, vol. 16, No. 5, Elsevier Science Limited, Great Britain.
Office Action mailed Aug. 11, 2023 in U.S. Appl. No. 16/770,195.
"U.S. Appl. No. 16/766,126, Corrected Notice of Allowability mailed Jan. 5, 2023", 3 pgs.
"U.S. Appl. No. 16/766,126, Corrected Notice of Allowability mailed Jul. 15, 2022", 3 pgs.
"U.S. Appl. No. 16/766,126, Notice of Allowance mailed Jun. 29, 2022", 11 pgs.
"U.S. Appl. No. 16/766,126, Notice of Allowance mailed Sep. 21, 2022", 11 pgs.
"U.S. Appl. No. 16/766,126, Preliminary Amendment filed May 21, 2020", 16 pgs.
"U.S. Appl. No. 16/766,126, Supplemental Preliminary Amendment filed Jun. 10, 2020", 8 pgs.
"U.S. Appl. No. 16/768,107, Corrected Notice of Allowability mailed Jan. 12, 2023", 3 pgs.
"U.S. Appl. No. 16/768,107, Non Final Office Action mailed Jun. 27, 2022", 8 pgs.
"U.S. Appl. No. 16/768,107, Notice of Allowance mailed Dec. 20, 2022", 7 pgs.
"U.S. Appl. No. 16/768,107, Preliminary Amendment filed May 29, 2020", 12 pgs.
"U.S. Appl. No. 16/768,107, Response filed Sep. 27, 2022 to Non Final Office Action mailed Jun. 27, 2022", 10 pgs.
"U.S. Appl. No. 16/770,195, Non Final Office Action mailed Dec. 20, 2023", 27 pgs.
"U.S. Appl. No. 16/770,195, Preliminary Amendment filed Jun. 5, 2020", 12 pgs.
"U.S. Appl. No. 16/770,195, Response filed Mar. 17, 2023 to Non Final Office Action mailed Oct. 20, 2022", 11 pgs.
"U.S. Appl. No. 16/770,195, Response filed Aug. 12, 2022 to Restriction Requirement mailed Jun. 13, 2022", 3 pgs.
"U.S. Appl. No. 16/770,195, Response filed Oct. 31, 2023 to Final Office Action mailed Aug. 11, 2023", 13 pgs.
"U.S. Appl. No. 16/770,195, Restriction Requirement mailed Jun. 13, 2022", 9 pgs.
"U.S. Appl. No. 18/061,231, Non Final Office Action mailed Jan. 19, 2024", 14 pgs.
"U.S. Appl. No. 18/061,231, Response filed Apr. 19, 2024 to Non Final Office Action mailed Jan. 19, 2024", 13 pgs.
"U.S. Appl. No. 18/061,231, Response filed Sep. 29, 2023 to Restriction Requirement mailed Aug. 1, 2023", 9 pgs.
"U.S. Appl. No. 18/061,231, Restriction Requirement mailed Aug. 1, 2023", 8 pgs.
"Australian Application Serial No. 2019310601, First Examination Report mailed May 25, 2023", 5 pgs.
"Australian Application Serial No. 2023200506, First Examination Report mailed Feb. 14, 2024", 3 pgs.
"Chinese Application Serial No. 201980003616.5, Office Action mailed Sep. 28, 2023", w/English Translation, 20 pgs.
"Chinese Application Serial No. 201980003616.5, Response filed Apr. 1, 2024 to Office Action mailed Sep. 28, 2023", W/English Claims, 24 pgs.
"Chinese Application Serial No. 201980003656.X, Office Action mailed Sep. 28, 2023", w/ English Translation, 17 pgs.
"Chinese Application Serial No. 201980003656.X, Response filed Apr. 1, 2024 to Office Action mailed Sep. 28, 2023", W/English Claims, 92 pgs.
"Chinese Application Serial No. 201980003656.X, Response filed Apr. 19, 2024 to Consultation by Telephone / In Person—Response Needed filed Apr. 8, 2024", W/ English Claims, 89 pgs.
"Chinese Application Serial No. 201980032488.7, Response filed Mar. 28, 2024 to Office Action mailed Sep. 28, 2023", W/English Claims, 23 pgs.
"European Application Serial No. 15818539.7, Extended European Search Report mailed Mar. 14, 2018", 15 pgs.
"European Application Serial No. 19816193.7, Communication Pursuant to Article 94(3) EPC mailed Apr. 26, 2023", 6 pgs.
"European Application Serial No. 19816194.5, Partial Supplementary European Search Report mailed Sep. 27, 2021", 23 pgs.
"European Application Serial No. 19840618.3, Extended European Search Report mailed Feb. 7, 2022", 10 pgs.
"European Application Serial No. 20864198.5, Extended European Search Report mailed Aug. 30, 2023", 9 pgs.
"European Application Serial No. 20913973.2, Partial Supplementary European Search Report mailed Sep. 14, 2023", 15 pgs.
"European Application Serial No. 22182712.4, Extended European Search Report mailed Dec. 5, 2022", 8 pgs.
"International Application Serial No. PCT/US2015/039747, International Preliminary Report on Patentability mailed Jan. 19, 2017", 7 pgs.
"International Application Serial No. PCT/US2015/039747, International Search Report mailed Dec. 11, 2015", 4 pgs.
"International Application Serial No. PCT/US2015/039747, Written Opinion mailed Dec. 11, 2015", 5 pgs.
"International Application Serial No. PCT/US2019/043720, International Search Report mailed Nov. 13, 2019", 6 pgs.
"International Application Serial No. PCT/US2019/043753, International Search Report mailed Nov. 13, 2019", 6 pgs.
"International Application Serial No. PCT/US2019/043753, Written Opinion mailed Nov. 13, 2019", 7 pgs.
"International Application Serial No. PCT/US2020/014068, International Search Report mailed Jun. 16, 2020", 6 pgs.
"International Application Serial No. PCT/US2020/014068, Written Opinion mailed Jun. 16, 2020", 14 pgs.
"International Application Serial No. PCT/US2020/014570, International Search Report mailed Jul. 6, 2020", 6 pgs.
"International Application Serial No. PCT/US2020/014570, Written Opinion mailed Jul. 06, 2020", 7 pgs.
"International Application Serial No. PCT/US2021/012131, International Search Report mailed May 27, 2021", 5 pgs.
"International Application Serial No. PCT/US2021/012131, Written Opinion mailed May, 27, 2021", 9 pgs.
"New biosensor microchip could speed up drug development", ScienceDaily, (2011).
Bajpai, "Blood protein adsorption onto macroporous semi-interpenetrating polymer networks (IPNs) of poly(ethylene glycol) (PEG) and poly(2-hydroxyethyl methacrylate) (PHEMA) and assessment of in vitro blood compatibility", Polymer International, val. 56, No. 2, (Feb. 2007), 231-244.
Baselt, D R, et al., "A biosensor based on magnetoresistance technology", Biosensors & Bioelectronics, 13(7-8), Elsevier Science LTD., (1998), 731-739.
Bayley, Hagan, "Photogenerated reactive intermediates and their properties", Laboratory Techniques in Biochemistry and Molecular Biology, Chapter 2 Vol. 12, Elsevier, (1983), 8-24.
Capanema, Nadia S.V, et al., "Superabsorbent crosslinked carboxymethyl cellulose-PEG hydrogels for potential wound dressing applications", International Journal of Biological Macromolecules, 106, (Aug. 26, 2017), 1218-1234.
Cha, et al., "Immobilization of oriented protein molecules on poly(ethylene glycol)-coated Si(111)", Proteomics, vol. 4, WILEY-VCH Verlag Gmbh & Co., Minneapolis, MN., (2004), 12 pgs.
Djamal, M., et al., "Giant Magnetoresistance Sensors Based on Ferrite Material and Its Applications", Researchgate; 2017; DOI: 10.5772/intechopen.70548. Magnetic sensors—Development Trends and application, (2017), 24 pgs.

(56) References Cited

OTHER PUBLICATIONS

Doyle, et al., "Catalytic Carbene Insertion into C-H Bonds", Chemical Reviews, vol. 110, No. 2, American Chemical Society, (2010), 704-724.
Edelstein, R. L, et al., "The BARC biosensor applied to the detection of biological warfare agents", Biosensors & Bioelectronics, 14, Elsevier Science B.V, (2000), 805-813.
Gaster, et al., "Quantification of protein interactions and solution transport using high-density GMR sensor arrays", Nat Nanotechnol, (2011), 314-320.
Graham, et al., "Magnetic field-assisted DNA hybridisation and simultaneous detection using micron-sized spin-valve sensors and magnetic nanoparticles", Sensors and Actuators B: Chemical, vol. 107 Elsevier Science B.V, (Feb. 2005), 936-944.
Graham, D. L., et al., "Magnetoresistive-based biosensors and biochips", TRENDS in Biotechnology, 22(9), Elsevier Ltd., (Sep. 2004), 455-462.
Hulme, S. E, et al., "Incorporation of prefabricated screw, pneumatic, and solenoid valves into microfluidic devices", Lab On a Chip, vol. 9, Department of Chemistry and Chemical Biology, Harvard University, Cambridge, Ma, USA, <https://pubs.rsc.org/en/content/articlehtml/2009/lc/b809673b>, (2009), 21 pgs.
Huo, Weisong, et al., "A Novel High-Sensitivity Cardiac Multibiomarker Detection System Based on Microfluidic Chip and GMR Sensors", IEEE Transactions On Magnetics, IEEE Service Center, New York, NY, US, vol. 51, No. 11, (Nov. 1, 2015), 4 pgs.
Klein, T., et al., "Development of a multiplexed giant magnetoresistive biosensor array prototype to quantify ovarian cancer biomarkers", Biosensors and Bioelectronics, vol. 126, Elsevier B.V, (Oct. 23, 2018), 14 pgs.
Koets, et al., "Rapid DNA multi-analyte immunoassay on a magnetoresistance biosensor", Biosensors and Bioelectronics, vol. 24, Elsevier B.V, (Oct. 8, 2008), 1893-1898.
Litwin, Douglas B, et al., "Single-Molecule FRET Methods to Study Glutamate Receptors", Methods in Molecular Biology, Author manuscript, (Jan. 1, 2020), 17 pgs.
Liu, et al., "Functional Nucleic Acid Sensors", Chem. Rev., Author Manuscript 109(5), (May 2009), 1948-1998.
Lu, et al., "New highly sensitive and selective catalytic DNA biosensors for metal ions", Biosensors and Bioelectronics, vol. 18 Elsevier Science BV, (2003), 12 pgs.
Martins, et al., "Femtomolar limit of detection with a magnetoresistive biochip", Biosensors and Bioelectronics, vol. 24, Elsevier B.V, (Feb. 6, 2009), 6 pgs.
Osterberg, F W, et al., "Bead Capture on Magnetic Sensors in a Microfluidic System", IEEE Sensors Journal, vol. 9, No. 6, Denmark, (Jun. 1, 2009), 682-688.
Rizzi, Giovanni, et al., "Denaturation strategies for detection of double stranded PCR products on GMR magnetic biosensor array", Biosensors and Bioelectronics, vol. 93, Elsevier B.V., Denmark, (Jul. 1, 2017), 20 pgs.
Sun, Xuecheng, et al., "Separable detecting of Escherichia coli O157H:H7by a giant magneto-resistance-based bio-sensing system", Sensors and Actuators B; Chemical, Elsevier Bv, Nl, vol. 234, (May 7, 2016), 485-492.
Tavakoli, et al., "Hydrogel Based Sensors for Biomedical Applications: An Updated Review; Polymers", (2017).
Teramura, Y, et al., "Surface plasmon resonance-based highly sensitive immunosensing for brain natriuretic peptide using nanobeads for signal amplification", Analytical Biochemistry, No. 357, Elsevier Inc., Japan, (2006), 208-215.
Tian, et al., "Rapid Newcastle Disease Virus Detection Based on Loop-Mediated Isothermal Amplification and optomagnetic Readout", ACS Sensors, vol. 1, ACS Publications, (2016), 1228-1234.
Wernette, et al., "Incorporation of a DNAzyme into Au-coated nanocapillary array membranes with an internal standard for Pb(II) sensing", The Analyst, The Royal Society of Chemistry, Issue 131, (Nov. 24, 2005), 7 pgs.
Wu, et al., "Comparison of Hydroxylated Print Additives on Antibody Microarray Performance", Journal of Proteome Research, vol. 5, American Chemical Society, (Oct. 19, 2006), 2956-2965.
Xu, et al., "Giant magnetoresistive biochip for DNA detection and HPV genotyping", Biosensors and Bioelectronics, vol. 24, Elsevier Science BV, (Apr. 8, 2008), 13 pgs.
Zellander, et al., "Characterization of Pore Structure in Biologically Functional Poly(2- Hydroxyethyl Methacrylate) - Poly(Ethylene Glycol) Diacrylate (Phema-Pegda)", Plos One, vol. 9, Issue 5, Chicago, Illinois, (May 9, 2014), 1-8.
Zhu, et al., "Functional Nucleic Acid-Based Sensors for Heavy Metal ion Assays", The Analyst, The Royal Society of Chemistry, vol. 139, No. 4, (2014), 6326-6342.
"Chinese Application Serial No. 201980032488.7, Office Action mailed Jun. 5, 2024", w English Translation, 7 pgs.
"Chinese Application Serial No. 201980003616.5, Office Action mailed Jun. 4, 2024", w English Translation, 9 pgs.
"European Application Serial No. 22182712.4, Response filed Aug. 8, 2023 to Extended European Search Report mailed Dec. 5, 2022", 27 pgs.
"Chinese Application Serial No. 201980003616.5, Response filed Jul. 31, 2024 to Office Action mailed Jun. 4, 2024", w current English claims, 18 pgs.
"Chinese Application Serial No. 201980032488.7, Response Filed Jul. 31, 2024 to Office Action mailed Jun. 5, 2024", w English Claims, 20 pgs.
"Application Serial No. 18,061,231, Notice of Allowance mailed Aug. 7, 2024", 10 pgs.
"Chinese Application Serial No. 201980003616.5, Response to Examiner Telephone Interview Filed Aug. 15, 2024", w English Claims, 16 pgs.
"Chinese Application Serial No. 201980003611.2, Office Action mailed Jul. 27, 2023", w English Translation, 19 pgs.
"Chinese Application Serial No. 201980032488.7, Response to Examiner Telephone Interview Filed Aug. 15, 2024", w English Claims, 19 pgs.

\* cited by examiner

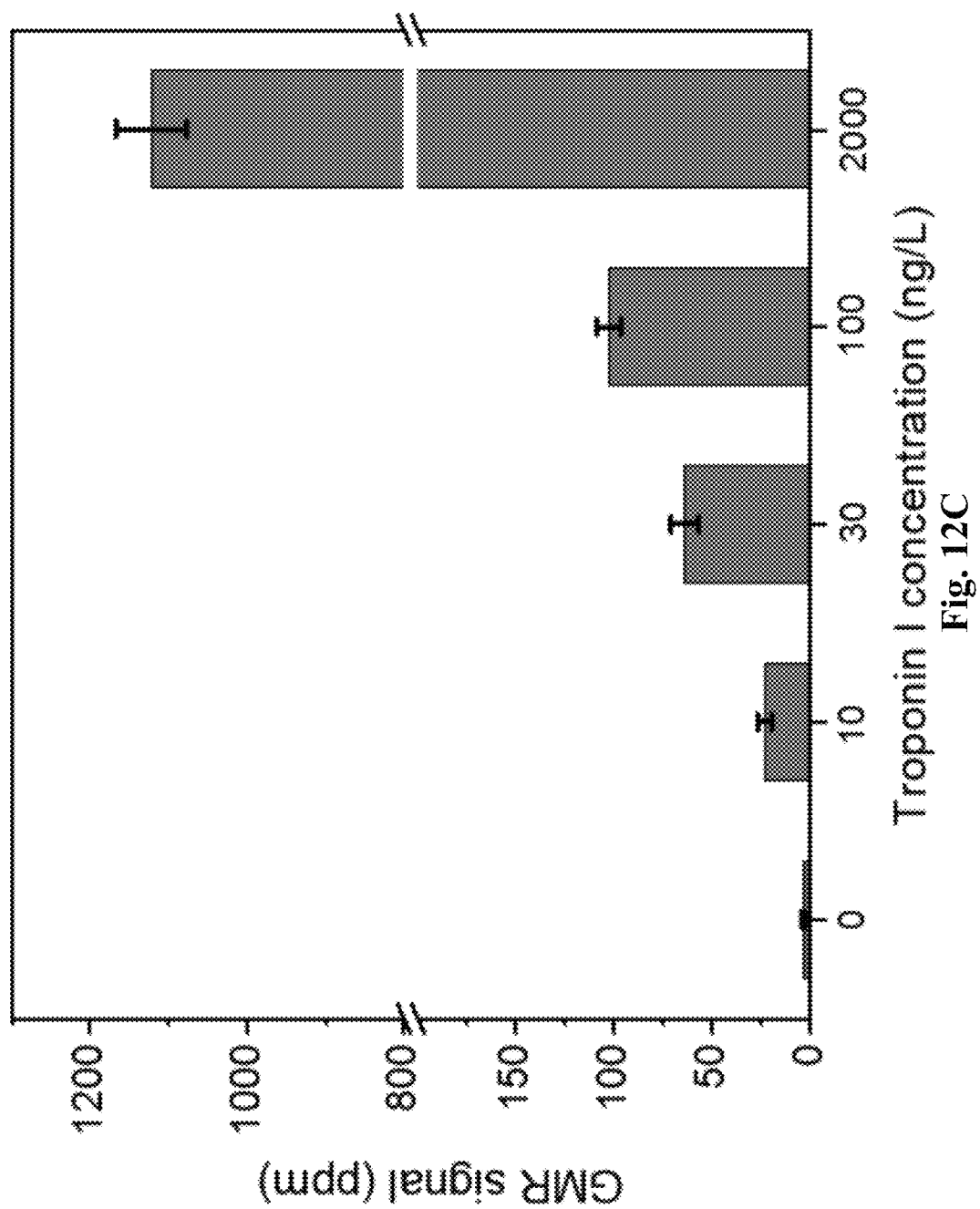

(Cartridge reader flowchart)

SYSTEM AND METHOD FOR PROCESSING ANALYTE SIGNALS IN GMR-BASED DETECTION OF BIOMARKERS

CROSS REFERENCE TO RELATED APPLICATIONS

This application a national stage application, filed under 35 U.S.C. § 371, of International Application No. PCT/US2019/043791, filed on Jul. 26, 2019, which claims priority to U.S. Provisional Patent Application No. 62/711,396, filed Jul. 27, 2018, both of which are incorporated herein by reference in their entireties.

BACKGROUND

Field

The present disclosure is generally related to systems and methods for processing measurement signals obtained from analyte detection based on Giant Magneto-Resistive (GMR) sensors. Specifically, the present disclosure relates to phase-sensitive detection systems and methods for processing the measurement signals in GMR-based analyte detection.

Description of Related Art

GMR sensors enable development of multiplex assays with high sensitivity and low cost in a compact system, and therefore have the potential to provide a platform suitable for a wide variety of applications. Prior art has already demonstrated the advantage of amplitude modulation of GMR sensor signals to improve signal-to-noise ratio (SNR) of the measurement, but the relationship between voltage amplitude, phase, and underlying magnetoresistance can be quite complex depending on the measurement circuits. As a result, some prior techniques may just ignore the phase information, while others may choose to perform DC measurement.

Thus, there is a need for improvement over the conventional approaches to derive a phase-sensitive measurement of GMR sensing signals while retaining the use of AC measurement.

SUMMARY

Embodiments herein relate to systems and methods for achieving phase-sensitive measurements and calculation of resistance of magnetoresistance (GMR) sensors used in analyte detection.

It is an aspect of this disclosure to provide a signal processing system used for GMR-based detection of a target analyte in a sample under test, comprising:
- a measurement circuit configuration unit configured to build a GMR sensor measurement circuit by routing in at least one GMR sensor, and to build a reference resistor measurement circuit by routing in at least one reference resistor;
- a magnetic field excitation unit configured to apply an AC magnetic field of frequency $\omega_2$ to the at least one GMR sensor;
- a carrier signal applying unit configured to apply a carrier signal of frequency $\omega_1$ to the GMR sensor measurement circuit, and apply carrier signals of frequency $\omega_1+\omega_2$, and $\omega_1-\omega_2$ to the reference resistor measurement circuit;
- a measurement signal pick-up unit coupled to the measurement circuits, configured to collect reference resistor measurement signals from the reference resistor measurement circuit and GMR sensor measurement signals from the GMR sensor measurement circuit; and
- a phase sensitive solution unit coupled to the measurement signal pick-up unit, configured to analytically solve for resistance change of the at least one GMR sensor based on both the reference resistor measurement signals from the reference resistor measurement circuit and the GMR sensor measurement signals from the GMR sensor measurement circuit.

Another aspect provides a signal processing method used for GMR-based detection of a target analyte in a sample under test, comprising:
- obtaining GMR sensor measurement signals, which comprises
  - building a GMR sensor measurement circuit by routing in at least one GMR sensor,
  - applying a carrier signal of frequency $\omega_1$ to the GMR sensor measurement circuit;
  - applying an AC magnetic field of frequency $\omega_2$ to the at least one GMR sensor; and
  - collecting the GMR sensor measurement signals from the GMR sensor measurement circuit;
- obtaining reference resistor measurement signals, which comprises:
  - building a reference resistor measurement circuit by routing in at least one reference resistor;
  - applying carrier signals of frequency $\omega_1$, $\omega_1+\omega_2$, and $\omega_1-\omega_2$ to the reference resistor measurement circuit; and
  - collecting the reference resistor measurement signals from the reference resistor measurement circuit; and
- analytically solving for resistance change of the at least one GMR sensor based on both the reference resistor measurement signals from the reference resistor measurement circuit and the GMR sensor measurement signals from the GMR sensor measurement circuit.

Other aspects, features, and advantages of the present disclosure will become apparent from the following detailed description, the accompanying drawings, and the appended claims.

BRIEF DESCRIPTION OF THE DRAWINGS

Various embodiments of the present disclosure will be described herein below with reference to the Figures wherein:

FIG. 12C shows a graph of data generated with a GMR sensor for detecting troponin cardiac biomarker.

DETAILED DESCRIPTION OF THE PREFERRED EMBODIMENT(S)

The present disclosure is related to systems and methods for processing measurement signals obtained from analyte detection using magnetoresistive sensor technologies. For explanatory purposes, in accordance with embodiments, the devices, systems, and features are described with respect to utilizing GMR sensors.

As evident by the drawings FIGS. 1-4 and the accompanying description, the signal processing technique in this disclosure may be used in a sample handling system (or "system" as noted throughout this disclosure) which may be used for detecting presence of an analyte (or analytes) such as metal, biomarkers, and the like, in a sample. In an embodiment, this system, depicted as system 300 in FIG. 3, may include (1) a sample handling system or "cartridge assembly" that includes sample preparation microfluidic channel(s) and at least one sensing device (or sensor) for sensing biomarkers in a test sample, and (2) a data processing and display device or "cartridge reader unit" that includes a processor or controller for processing any sensed data of the sensing device of the cartridge assembly and a display for displaying a detection event. Together these two components make up the system. In an embodiment, these components may include variable features including, without limitation, one or more reagent cartridges, a cartridge for waste, and a flow control system which may be, for example, a pneumatic flow controller.

Generally, the process for preparing a sample in the cartridge assembly, in order for detection of analytes, biomarkers, etc. to happen by the assembly and output via the cartridge reader unit, is as-follows: A raw patient sample is loaded onto a card, optionally filtered via a filter membrane, after which a negative pressure generated by off-card pneumatics filters the sample into a separated test sample (e.g., plasma). This separated test sample is quantitated on-card through channel geometry. The sample is prepared on card by interaction with mixing materials (e.g., reagent(s) (which may be dry or wet), buffer and/or wash buffer, beads and/or beads solution, etc.) from a mixing material source (e.g., blister pack, storage chamber, cartridge, well, etc.) prior to flow over the sensor/sensing device. The sample preparation channels may be designed so that any number of channels may be stacked vertically in a card, allowing multiple patient samples to be used. The same goes for sensing microfluidic devices, which may also be stacked vertically. A sample preparation card, which is part of the cartridge assembly, includes one or more structures providing functionalities selected from filtering, heating, cooling, mixing, diluting, adding reagent, chromatographic separation and combinations thereof; and a means for moving a sample throughout the sample preparation card. Further description regarding these features is provided later below.

Figure 1:
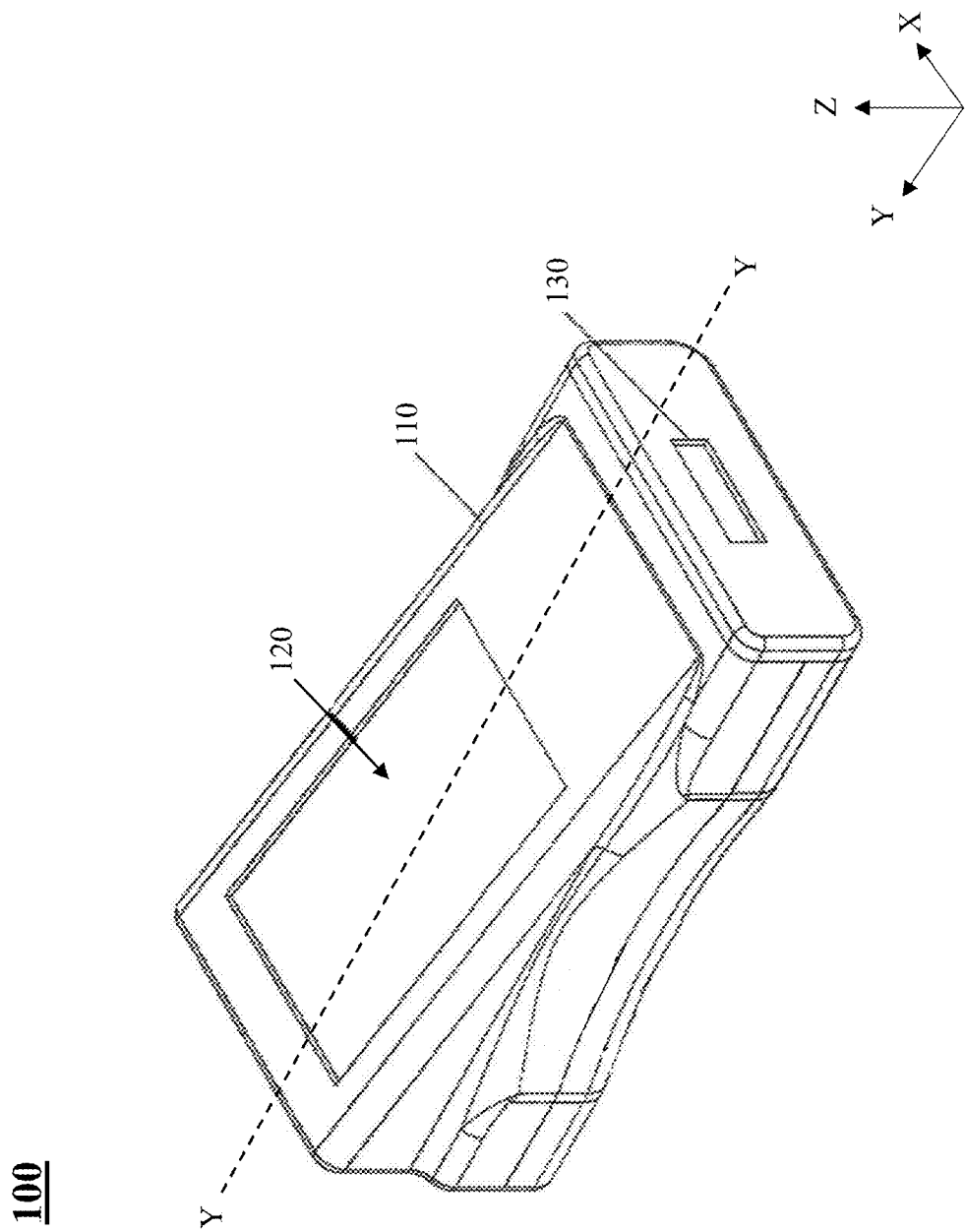
FIG. 1 is a perspective view of an exemplary cartridge reader unit used in a system in accordance with an embodiment of the present disclosure.

FIG. 1 shows an example of a cartridge reader unit 100, used in system 300 (see FIG. 3) in accordance with an embodiment. The cartridge reader unit 100 may be configured to be compact and/or small enough to be a hand-held, mobile instrument, for example. The cartridge reader unit 100 includes a body or housing 110 that has a display 120 and a cartridge receiver 130 for receiving a cartridge assembly. The housing 110 may have an ergonomic design to allow greater comfort if the reader unit 100 is held in an operator's hand. The shape and design of the housing 110 is not intended to be limited, however.

The cartridge reader unit 100 may include an interface 140 and a display 120 for prompting a user to input and/or connect the cartridge assembly 200 with the unit and/or sample, for example. In accordance with an embodiment, in combination with the disclosed cartridge assembly 200, the system 300 may process, detect, analyze, and generate a report of the results, e.g., regarding multiple detected biomarkers in a test sample, e.g., five cardiac biomarkers, using sensor (magnetoresistive) technology, and further display the biomarker results, as part of one process.

The display 120 may be configured to display information to an operator or a user, for example. The display 120 may be provided in the form of an integrated display screen or touch screen (e.g., with haptics or tactile feedback), e.g., an LCD screen or LED screen or any other flat panel display, provided on the housing 110, and (optionally) provides an input surface that may be designed for acting as end user interface (UI) 140 that an operator may use to input commands and/or settings to the unit 100, e.g., via touching a finger to the display 120 itself. The size of the display 120 may vary. More specifically, in one embodiment, the display 120 may be configured to display a control panel with keys, buttons, menus, and/or keyboard functions thereon for inputting commands and/or settings for the system 300 as part of the end user interface. In an embodiment, the control panel includes function keys, start and stop buttons, return or enter buttons, and settings buttons. Additionally and/or alternatively, although not shown in FIG. 1, the cartridge reader 100 may include, in an embodiment, any number of physical input devices, including, but not limited to, buttons and a keyboard. In another embodiment, the cartridge reader 100 may be configured to receive input via another device, e.g., via a direct or wired connection (e.g., using a plug and cord to connect to a computer (PC or CPU) or a processor) or via wireless connection. In yet another embodiment, display 120 may be to an integrated screen, or may be to an external display system, or may be to both. Via the display control unit 120, the test results (e.g., from a cartridge reader 310, described with reference to FIG. 3, for example) may be displayed on the integrated or external display. In still yet another embodiment, the user interface 140 may be provided separate from the display 120. For example, if a touch screen UI is not used for display 120, other input devices may be utilized as user interface 140 (e.g., remote, keyboard, mouse, buttons, joystick, etc.) and may be associated with the cartridge reader 100 and/or system 300. Accordingly, it should be understood that the devices and/or methods used for input into the cartridge reader 100 are not intended to be limiting. All functions of the cartridge reader 100 and/or system 300 may, in one embodiment, be managed via the display 120 and/or input device(s), including, but not limited to: starting a method of processing (e.g., via a start button), selecting and/or altering settings for an assay and/or cartridge assembly 200, selecting and/or settings related to pneumatics, confirming any prompts for input, viewing steps in a method of processing a test sample, and/or viewing (e.g., via display 120 and/or user interface 140) test results and values calculated by the GMR sensor and control unit/cartridge reader. The display 120 may visually show information related to analyte detection in a sample. The display 120 may be configured to display generated test results from the control unit/cartridge reader. In an embodiment, real-time feedback regarding test results that have been determined/processed by the cartridge reader unit/controller (by receiving measurements from the sensing device, the measurements being determined as a result of the detected analytes or biomarkers), may be displayed on the display 120.

Optionally, a speaker (not shown) may also be provided as part of the cartridge reader unit 100 for providing an audio output. Any number of sounds may be output, including, but not limited to speech and/or alarms. The cartridge reader unit 100 may also or alternatively optionally include any number of connectors, e.g., a LAN connector and USB connector, and/or other input/output devices associated therewith. The LAN connector and/or USB connector may be used to connect input devices and/or output devices to the cartridge reader unit 100, including removable storage or a drive or another system.

In accordance with an embodiment, the cartridge receiver 130 may be an opening (such as shown in FIG. 1) within the housing 110 in which a cartridge assembly (e.g., cartridge assembly 200 of FIG. 2) may be inserted. In another embodiment, the cartridge receiver 130 may include a tray that is configured to receive a cartridge assembly therein. Such a tray may move relative to the housing 110, e.g., out of and into an opening therein, and to thereby receive the cartridge assembly 200 and move the cartridge assembly into (and out of) the housing 110. In one embodiment, the tray may be a spring-loaded tray that is configured to releasably lock with respect to the housing 110. Additional details associated with the cartridge reader unit 100 are described later with respect to FIG. 3.

Figure 2A:
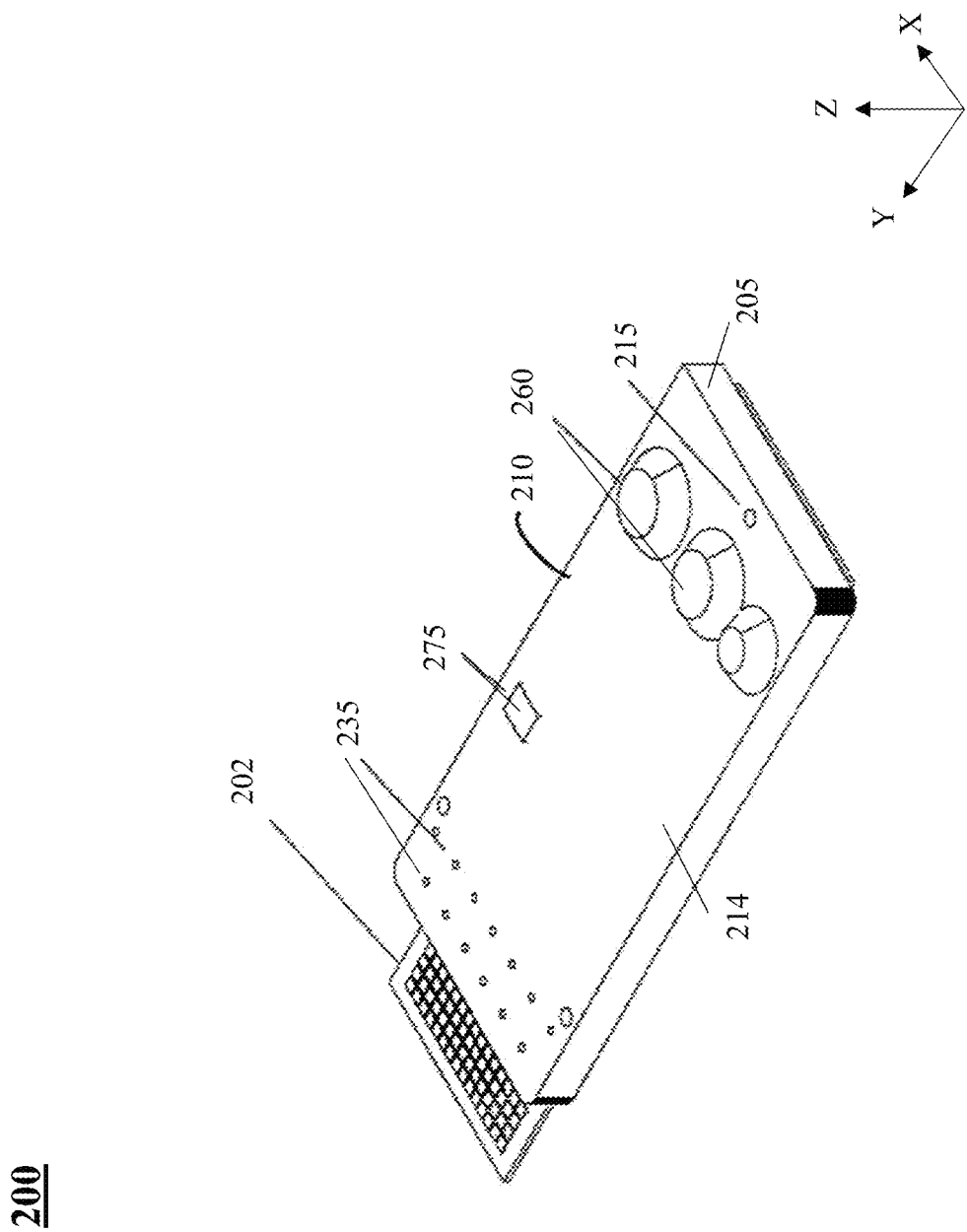
FIG. 2A is a perspective view of an exemplary cartridge assembly used in the system, in accordance with an embodiment of the present disclosure.
Figure 2B:
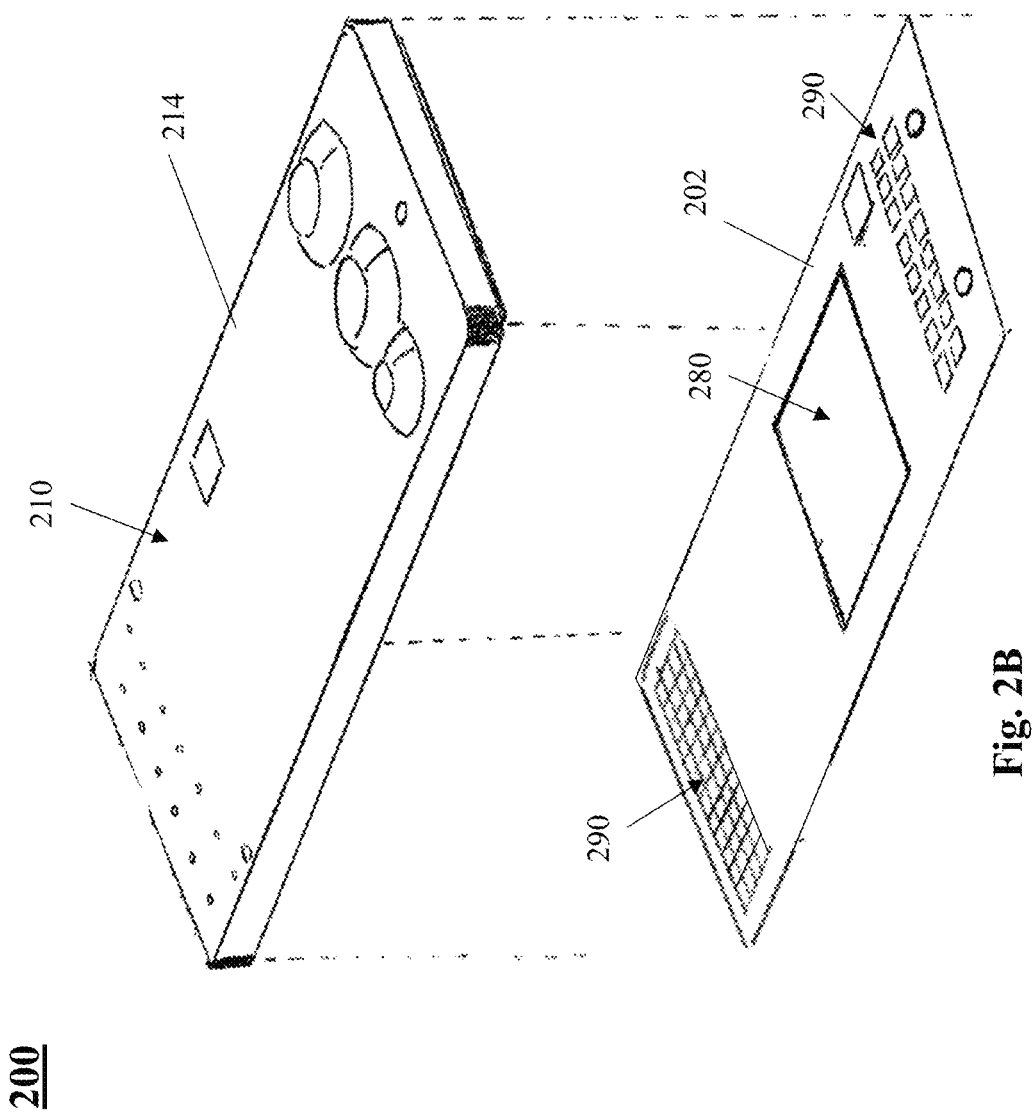
FIG. 2B is an exploded view of the cartridge assembly of FIG. 2A, in accordance with an embodiment herein.
Figure 2C:
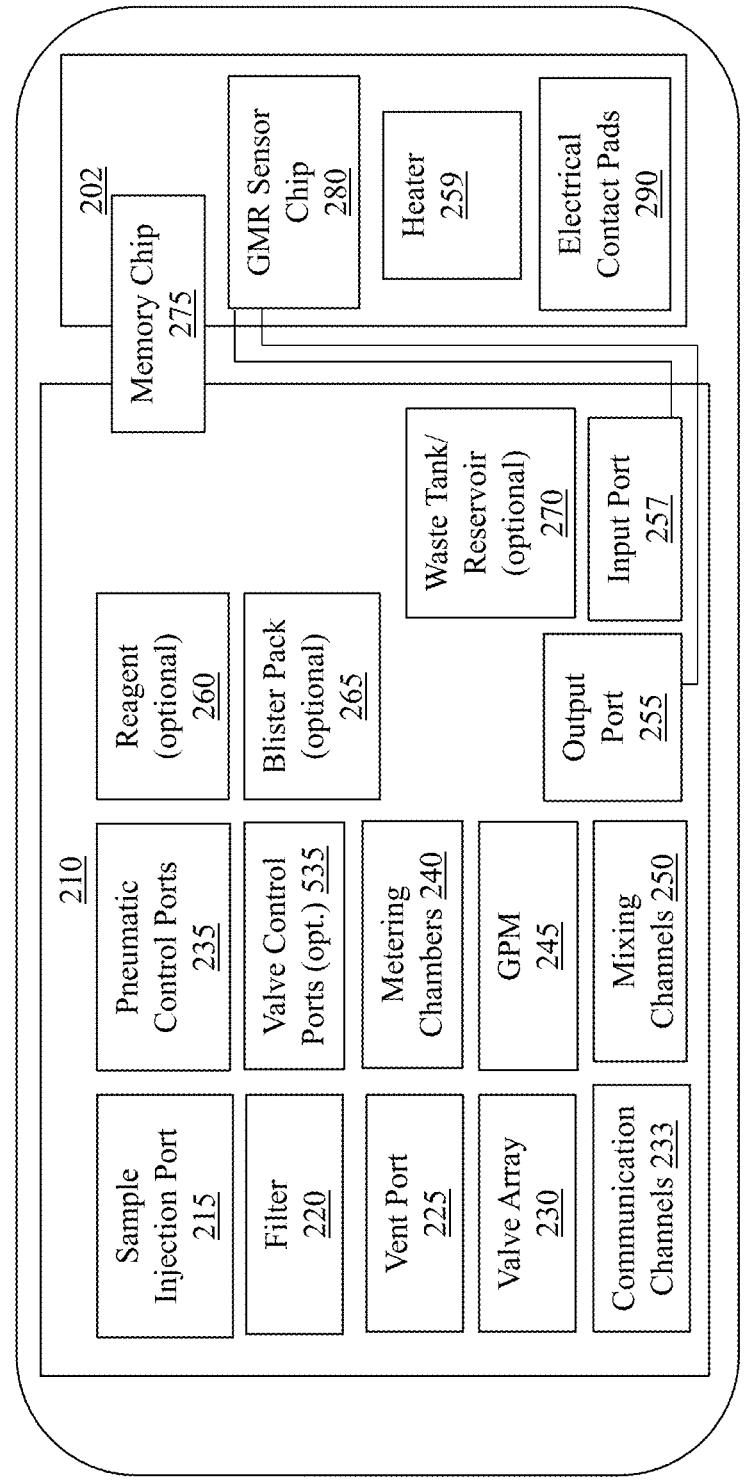
FIG. 2C is a schematic drawing of the cartridge assembly of FIG. 2A, in accordance with an embodiment herein.

As previously noted, cartridge assembly 200 may be designed for insertion into the cartridge reader unit 100, such that a sample (e.g., blood, urine) may be prepared, processed, and analyzed. FIGS. 2A-2C illustrate an exemplary embodiment of a cartridge assembly 200 in accordance with embodiments herein. Some general features associated with the disclosed cartridge assembly 200 are described with reference to these figures. However, as described in greater detail later, several different types of cartridge cards and thus cartridge assemblies may be utilized with the cartridge reader unit 100 and thus provided as part of system 300. In embodiments, the sampling handling system or cartridge assembly 200 may take the form of disposable assemblies for conducting individual tests. That is, as will be further understood by the description herein, depending on a type of sample and/or analytes being tested, a different cartridge card configuration(s) and/or cartridge assembly(ies) may be utilized. FIG. 2A shows a top, angled view of a cartridge assembly 200, in accordance with an embodiment herein. The cartridge assembly 200 includes a sample processing card 210 and a sensing and communication substrate 202 (see also FIG. 2B). Generally, the sample processing card 210 is configured to receive the sample (e.g., via a sample port such as injection port, also described below) and, once inserted into the cartridge reader unit 100, process the sample and direct flow of the sample to produce a prepared sample. Card 210 may also store waste from a sample and/or fluids used for preparing the test sample in an internal waste chamber(s) (not shown in FIG. 2A, but further described below). Memory chip 275 may be read and/or written to and is used to store information relative to the cartridge application, sensor calibration, and sample processing required, for example. In an embodiment, the memory chip 275 is configured to store a pneumatic system protocol that includes steps and settings for selectively applying pressure to the card 210 of the cartridge assembly 200, and thus implementing a method for preparation of sample for delivery to a magnetoresistive or magnetoresistance sensor (e.g., GMR sensor chip 280). The memory chip may be used to mistake-proof each cartridge assembly 200 inserted into the unit 100, as it includes the automation recipe for each assay. The memory chip 275 also contain traceability to the manufacturing of each card 210 and/or cartridge assembly 200. The sensing and communication substrate 202 may be configured to establish and maintain communication with the cartridge reader unit 100, as well as receive, process, and sense features of the prepared sample. The substrate 202 establishes communication with a controller in the cartridge reader unit 100 such that analyte(s) may be detected in a prepared sample. The sample processing card 210 and the sensing and communication substrate 202 (see, e.g., FIG. 2B) are assembled or combined together to form the cartridge assembly 200. In an embodiment, adhesive material (see, e.g., FIG. 2D) may optionally be used to adhere the card 210 and substrate 202 to one another. In an embodiment, the substrate 202 may be a laminated layer applied to the sample processing card 210. In one embodiment, the substrate 202 may be designed as a flexible circuit that is laminated to sample processing card 210. In another embodiment, the sample processing card 210 may be fabricated from a ceramic material, with the circuit, sensor (sensor chip 280) and fluid channels integrated thereon. Alternatively, the card 210 and substrate 202 may be mechanically aligned and connected together. In one embodiment, a portion of the substrate 202 may extend from an edge or an end of the card 210, such as shown in FIG. 2A. In another embodiment, such as shown in FIG. 2B, the substrate 202 may be aligned and/or sized such that it has similar or smaller edges than the card 210.

Figure 3:
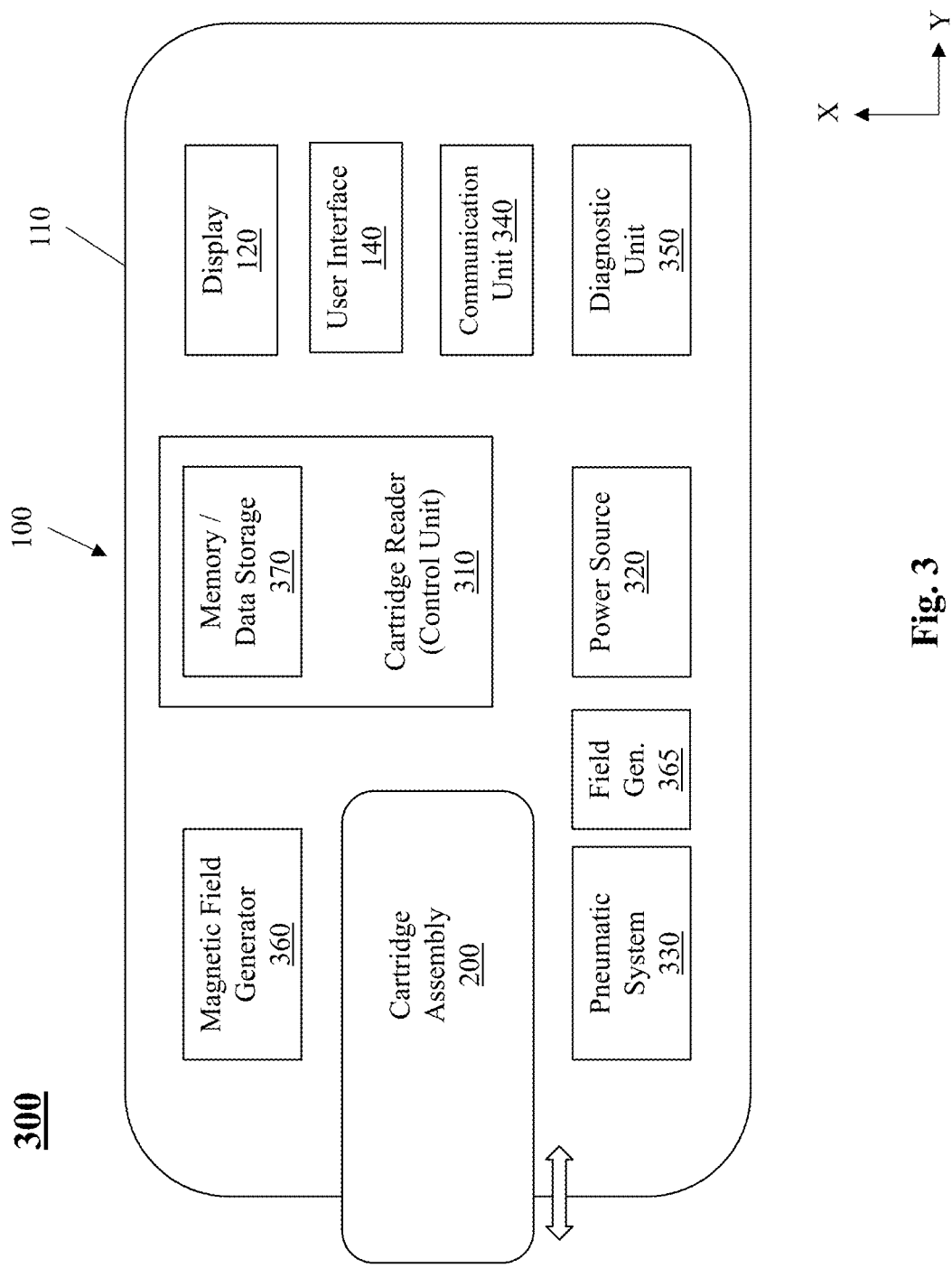
FIG. 3 is a schematic diagram of the system in accordance with an embodiment of the present disclosure.

FIG. 2C schematically illustrates features of the cartridge assembly 200, in accordance with an embodiment. As shown, some of the features may be provided on the sample processing card 210, while other may be associated with the substrate 202. Generally, to receive a test sample (e.g., blood, urine) (within a body of the card), the cartridge assembly 200 includes a sample injection port 215, which may be provided on a top of the card 210. Also optionally provided as part of the card 210 are filter 220 (also referred to herein as a filtration membrane), vent port 225, valve array 230 (or valve array zone 230), and pneumatic control ports 235. Communication channels 233 are provided within the card 210 to fluidly connect such features of the card 210. Pneumatic control ports 235 are part of a pneumatic interface on the cartridge assembly 200 for selectively applying pressurized fluid (air) to the communication channels 233 of the card, for directing flow of fluids (air, liquids, test sample, etc.) therein and/or valve array 230. Optionally, the card 210 may include distinct valve control ports 535 connected to designated communication channels 233 for controlling the valves in the valve array 230. The card 210 may also have one or more metering chambers 240, gas permeable membranes 245, and mixing channels 250 that are fluidly connected via communication channels 233. Metering chamber (s) are designed to receive at least the test sample (either directly or filtered) therein via communication channels 233. Generally, a sample may be injected into the cartridge assembly 200 through port 215 and processed by means of filtering with filter (e.g., filter 220), metering in metering chamber(s) 240, mixing in mixing channel(s) 250, heating and/or cooling (optional), and directing and changing the flow rate via communication channels 233, pneumatic control ports 235, and valve array 230. For example, flow of the fluid may be controlled using internal micro fluidic channels (also generally referred to as communication channels 233 throughout this disclosure) and valves via a connection of a pneumatic system (e.g., system 330 in the cartridge reader unit 100, as shown in FIG. 3) and a pneumatic interface e.g., on the card 210 that has pneumatic control ports 235 or a similar connection section. Optional heating of the test sample and/or mixing materials/fluids within the card 210 may be implemented, in accordance with an embodiment, via a heater 259 which may be in the form of a wire trace provided on a top side of a PCB/substrate 202 with a thermistor. Optional cooling of the test sample and/or mixing materials/fluids within the card 210 may be implemented, in accordance with an embodiment, via a TEC module integrated in the cartridge assembly 200 (e.g., on the substrate 202), or, in another embodiment, via a module integrated inside of the cartridge reader unit 100. For example, if the cooling module is provided in the unit 100, it may be pressed against the cartridge assembly 200 should cooling be required. Processing may also optionally include introduction of reagents via optional reagent sections 260 (and/or blister packs) on the card 210 and/or via reagent cartridges in the housing 110 the cartridge reader unit 100. Reagents may be released or mixed as required by the process for that sample and the cartridge assembly 200 being analyzed. Further, optional blister packs 265 may be provided on the card 210 to introduce materials such as reagents, eluants, wash buffers, magnetic nano particles, bead solution, or other buffers to the sample via communication channels 233 during processing. One or more internal waste chambers (also referred to herein as waste tanks for waste reservoirs) 270 may also be optionally provided on the card 210 to store waste from the sample and reagents. An output port 255—also referred to as a sensor delivery port, or input port to the sensor—is provided to output a prepared sample from the card 210 to a GMR sensor chip 280, as discussed below, for detecting analytes in the test sample. The output port 255 may be fluidly connected to a metering chamber for delivering the test sample and one or more mixing materials to the sensor. Accordingly, the sensor may be configured to receive the test sample and the one or more mixing materials via the at least one output port 255. In embodiments, an input port 257—also referred to as a waste delivery port, or output port from the sensor—is provided to output any fluid or sample from the GMR sensor chip 280 to a waste chamber 270. Waste chamber(s) 270 may be fluidly connected to other features of the card 210 (including, for example, metering chamber(s) 240, an input port 257, or both) via communication channels 233.

The cartridge assembly 200 has the ability to store, read, and/or write data on a memory chip 275, which may be associated with the card 210 or the substrate 202. As noted previously, the memory chip 275 may be used to store information related and/or relative to the cartridge application, sensor calibration, and required sample processing (within the sample processing card), as well as receive additional information based on a prepared and processed sample. The memory chip 275 may be positioned on the sample processing card 210 or on the substrate 200.

As previously noted, a magnetoresistive sensor may be utilized, in accordance with embodiments herein, to determine analytes (such as biomarkers) within a test sample using the herein disclosed system. While the description and Figures note use of a particular type of magnetoresistance sensor, i.e., a giant magnetoresistance (GMR) sensor, it should be understood that this disclosure is not limited to a GMR sensor platform. In accordance with some embodiments, the sensor may be an anisotropic magnetoresistive (AMR) sensor and/or magnetic tunnel junction (MTJ) sensors, for example. In embodiments, other types of magnetoresistive sensor technologies may be utilized. Nonetheless, for explanatory purposes only, the description and Figures reference use of a GMR sensor as a magnetoresistive sensor.

The substrate 202 of cartridge assembly 200 may be or include an electronic interface and/or a circuit interface such as a PCB (printed circuit board) that may have a giant magnetoresistance (GMR) sensor chip 280 and electrical contact pads 290 (or electrical contact portions) associated therewith. Other components may also be provided on the substrate 202. The GMR sensor chip 280 is attached at least to the substrate 202, in accordance with an embodiment. The GMR sensor chip 280 may be placed on and attached to the substrate 202 using adhesive, for example. In an embodiment, a liquid adhesive or a tape adhesive may be used between the GMR sensor 280 and the PCB substrate 202. Such a design may require a bond to the PCB at the bottom and a bond to the processing card at the top, for example. Alternatively, other approaches for attaching the GMR sensor chip 280 to the substrate 202 include, but are not limited to: friction fitting the GMR sensor to the PCB, and connecting a top of the GMR sensor chip 280 directly to the sample processing card 210 (e.g., in particular when the substrate 202 is provided in the form of a flexible circuit that is laminated (to the back) of sample processing card 210. The GMR sensor chip 280 may be designed to receive a prepared sample from the output port 255 of the sample processing card 210. Accordingly, placement of the GMR sensor chip 280 on the substrate may be changed or altered based on a position of the output port 255 on card 210 (thus, the illustration shown in FIG. 2B is not intended to be limiting)—or vice versa. In an embodiment, the GMR sensor chip 280 is positioned on a first side of the substrate 202 (e.g., a top side that faces an underside of the card 210, as shown in FIG. 2B), e.g., so as to receive the prepared sample from an output port that outputs on an underside of the card 210, and the contact pads 290 are positioned on an opposite, second side of the substrate (e.g., on a bottom side or underside of the substrate 202, such that the contact pads 290 are exposed on a bottom side of the cartridge assembly 200 when fully assembled for insertion into the cartridge reader unit 100). The GMR sensor chip 280 may include its own associated contact pads (e.g., metal strips or pins) that are electrically connected via electronic connections on the PCB/substrate 202 to the electrical contact pads 290 provided on the underside thereof. Accordingly, when the cartridge assembly 200 is inserted into the cartridge reader 100, the electrical contact pads 290 are configured to act as an electronic interface and establish an electrical connection and thus electrically connect with electronics (e.g., cartridge reader 310) in the cartridge reader unit 100. Thus, any sensors in the sensor chip 280 are connected to the electronics in the cartridge reader unit 100 through the electrical contact pads 290 and contact pads of the GMR sensor chip 280.

Figure 2D:
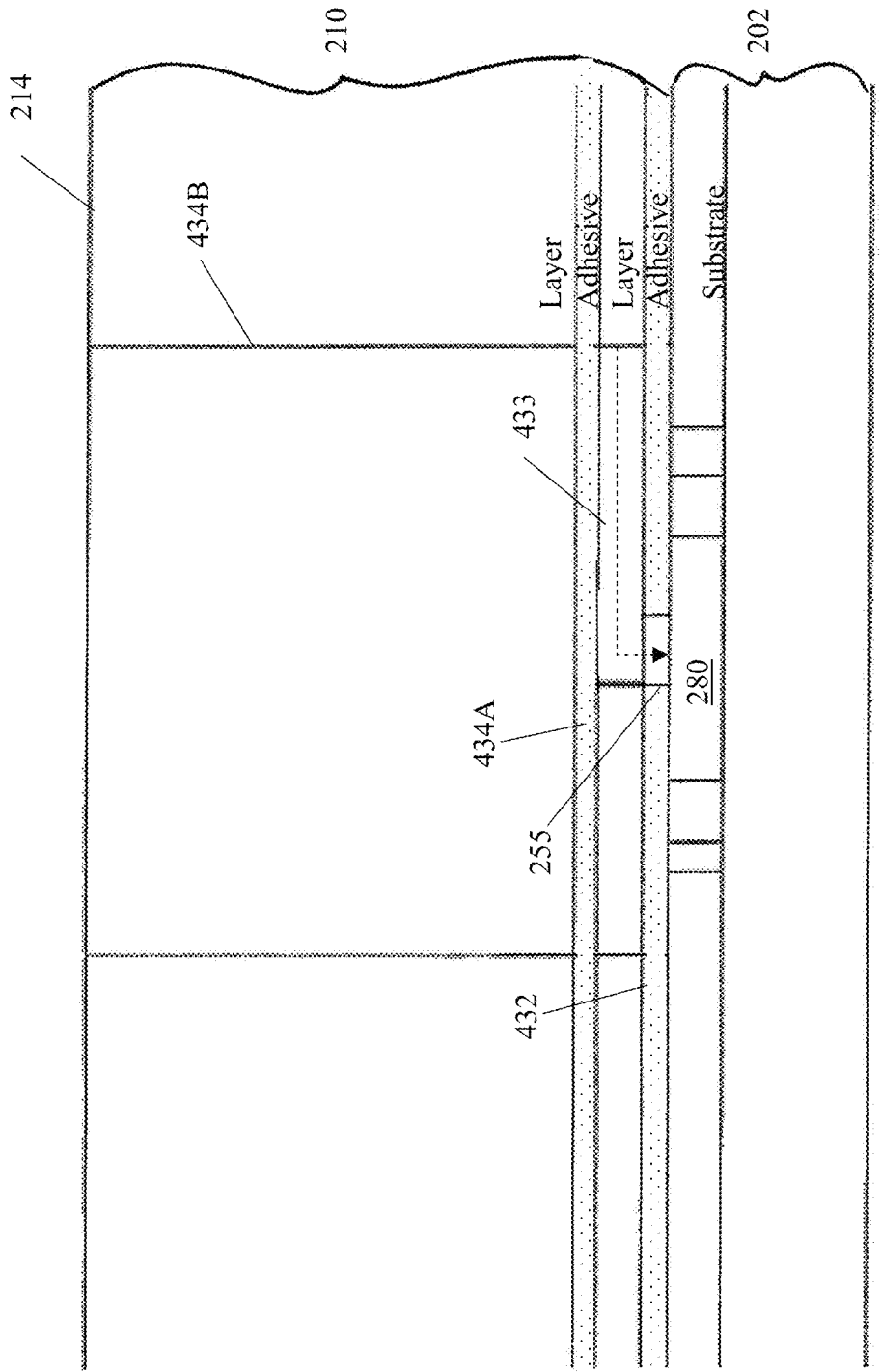
FIG. 2D shows a cross section of the cartridge assembly of FIG. 2A, illustrating a connection interface between a sample processing card and a sensing and communication substrate thereof.

FIG. 2D shows a view of an exemplary cross section of a mating or connection interface of card 210 and substrate 202. More specifically, FIG. 2D illustrates an interface, in accordance with one embodiment, between an output port 255 on the card 210 and GMR sensor chip 280 of the substrate 202. For example, shown is a PCB substrate 202 positioned below and adjacent to a card 210 according to any of the herein disclosed embodiments. The substrate 202 may be attached to bottom surface of the card 210. The card 210 has a channel feature, labeled here as microfluidic channel 433 (which is one of many communication channels within the card 210), in at least one layer thereof, designed to direct a test sample that is processed within the card 210 to an output port 255 directed to GMR sensor 280. Optionally, adhesive material may be provided between layers of the card 210, e.g., adhesive 434A may be provided between a layer in the card that has reagent ports 434B and a layer with the channel 433. The substrate 202 includes a GMR sensor chip 280 that is positioned adjacent to the channel 433 and output port 255 of the card 210.

Magnetic field (from a magnetic field generator 365 that is different than magnetic field generator 360, described below with reference to FIG. 3) may be used to excite the nano magnetic particles located near sensors.

Referring now to FIG. 3, additional features of the cartridge reader unit 100 are schematically shown to further describe how the cartridge reader unit 100 and cartridge assembly 200 are configured to work together to provide the system 300 for detecting analyte(s) in a sample. As depicted, the cartridge assembly 200 may be inserted into the housing 110 of the cartridge reader unit 100. Generally, the housing 110 of the cartridge reader unit 100 may further include or contain a processor or control unit 310, also called a "controller" and/or a "cartridge reader" 310 here throughout, a power source 320, a pneumatic system 330, a communications unit 340, a (optional) diagnostic unit 350, a magnetic field generator 360, and a memory 370 (or data storage), along with its user interface 140 and/or display 120. Optionally, a reagent opener (not shown in FIG. 3), e.g., for opening a reagent source on an inserted cartridge assembly or for introducing reagent into the cartridge assembly (e.g., if the reagent is not contained in the assembly in a particular reagent section), may also be provided as part of the cartridge reader unit 100. Once a cartridge assembly 200 is inserted into the housing 110 of the cartridge reader unit 100, and the electrical and pneumatics system(s) are connected, and the cartridge memory chip 275 may be read from the cartridge assembly 200 (e.g., read by cartridge reader 310/control unit, or PCB assembly, in the unit 100) to determine the pneumatic system protocol that includes steps and settings for selectively applying pressure to the card 210 of the cartridge assembly 200, and thus implementing a method for preparation of sample for delivery to a sensor (e.g., GMR sensor chip 280), and thus the sample placed in the assembly 200 may be prepped, processed, and analyzed. The control unit or cartridge reader 310 may control inputs and outputs required for automation of the process for detecting the analyte(s) in a sample. The cartridge reader 310 may be a real-time controller that is configured to control, among other things, the giant magnetic resistance (GMR) sensor chip 280 and/or memory chip 275 associated with the cartridge assembly 200 and the pneumatic system 330 within the housing 110, as well as the controls from user interface, driving the magnetic field generator 360, and receiving and/or sending signals from/to sensor chip and/or memory associated with the cartridge assembly 200, for example. In an embodiment, the cartridge reader 310 is provided in the form of a PCB (printed circuit board) which may include additional chips, memory, devices, therein. The cartridge reader 310 may be configured to communicate with and/or control an internal memory unit, a system operation initializer, a signal preparing unit, a signal preparing unit, a signal processing unit, and/or data storage (none of which are shown in the Figures), for example. The cartridge reader 310 may also be configured to send and receive signals with respect to the communications unit 340 such that network connectivity and telemetry (e.g., with a cloud server) may be established, and non-volatile recipes may be implemented, for example. Generally, the communications unit 340 allows the cartridge reader unit 100 to transmit and receive data using wireless or wired technology. Power can be supplied to the cartridge reader unit 100 via power source 320 in the form of an internal battery or in the form of a connector that receives power via an external source that is connected thereto (e.g., via a cord and a plug). Power source 320 is configured to supply power to parts of the cartridge reader unit 100, when activated and/or when a cartridge assembly 200 is mated with the unit 100. For example, power source 320 may supply power to the control unit and PCB assembly 560 of cartridge reader 310, magnetic field generator 360, display 120 and/or user interface 140, and pneumatic system 330 (including, for example, any motors, valves, and/or pumps associated therewith). Power source 320 may be at least one internally mounted battery pack 320, in accordance with an embodiment herein. The pneumatic system 330 is used to process and prepare a sample (e.g., blood, urine) placed into the cartridge assembly 200 by means of moving and directing fluids inside and along the sample processing card 210 (e.g., via pneumatic connection 235, through its channels and connecting to direct elastomeric valves). The pneumatic system 330 may be a system and/or device for moving fluid, which could use, for example, plungers and/or pistons in contact with fluids. The magnetic field generator 360 may be an external magnetic coil or other field generating device that is mounted in the unit 100 or integrated in some fashion with one or more of the chips (e.g., sensor chip 280) provided on the cartridge assembly 200 or provided on the circuit board of the cartridge reader unit 100. The magnetic field generator 360 is used to stimulate magnetic nanoparticles near the GMR sensor chip 280 while reading the signal. In accordance with embodiments, a second magnetic field generator 365, which may be a coil or other field generating device, may be provided as part of the cartridge reader unit 100 and in the housing 110. For example, in accordance with an embodiment, the second magnetic field generator 365 may be separate and distinct from magnetic field generator 360. This second magnetic field generator 365 may be configured to generate a non uniform magnetic field such that it may apply such a magnetic field to a part (e.g., top, bottom, sides) of the sample processing card 210 of an assembly 200 during preparation and processing of a sample, e.g., when moving mixing material(s), such as a buffer and/or magnetic beads from a mixing material source, and test sample within the card. In an embodiment, the second magnetic field generator 365 is provided on an opposite end or side of the cartridge reader unit (e.g., located in a top of the housing 110 of unit 100), i.e. away from the magnetic field generator 360, which is used for GMR sensing. In one embodiment, the second magnetic field generator 365 is provided on an opposite end of the cartridge reader unit as compared to the magnetic field generator 360 (e.g., second magnetic field generator is located in a top of the housing 110 of unit 100 and magnetic field generator 360 is provided at a bottom end of the unit 100 (e.g., near cartridge receiver 130)). In an embodiment, the total magnetic field for sensing biomarkers includes an applied field from magnetic field generator 360 (either external or integrated with the sensor chip) along with any disturbance from magnetic nanoparticles near the GMR sensor chip 280. The reagent opener is optionally used to introduce reagents during the sample processing and reading of the GMR sensor chip 280 (e.g., if the reagent is not contained in the card in a particular reagent section). As described previously, the user interface/display 120 allows an operator to input information, control the process, provide system feedback, and display (via an output display screen, which may be a touch screen) the test results.

Figure 4:
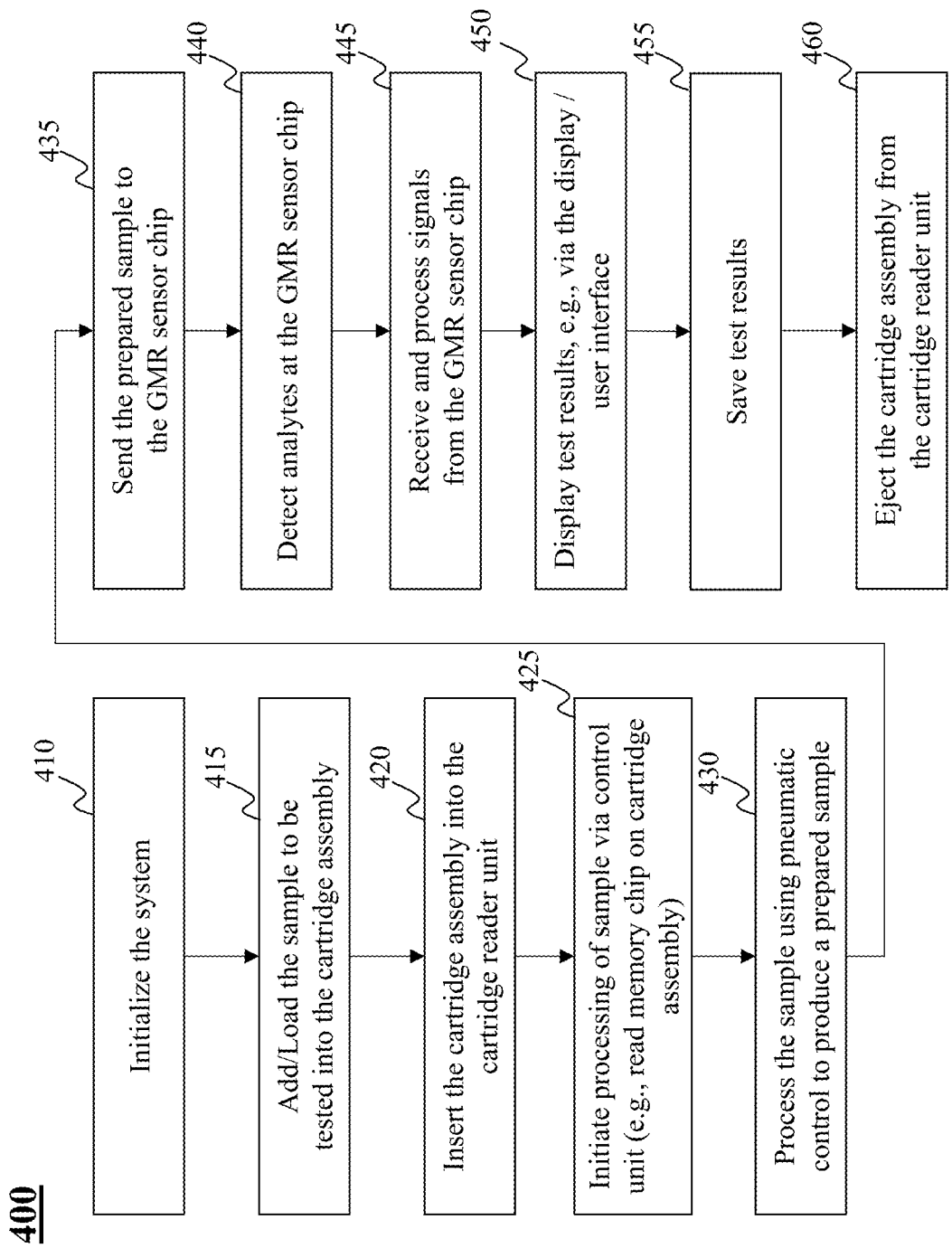
FIG. 4 shows steps of a method for performing analyte detection in a sample when using features of the herein disclosed system of FIG. 3, in accordance with an embodiment.

FIG. 4 shows general steps of a method 400 for performing analyte detection in a sample using the herein disclosed system 300. At step 410, the system is initialized. For example, initialization of the system may include: applying power to the system 300 (including cartridge reader unit 100), determining configuration information for the system, reading computations, determining that features (e.g., magnetic field generator and carrier signals) are online and ready, etc. At step 415, a whole test sample is added or loaded into the cartridge assembly 200 (e.g., sample is injected into the injection port 215, as shown in FIG. 2C). The order of steps 410 and 415 may be changed; i.e., the addition of the whole test sample to the assembly 200 may be before or after the system is initialized. At step 420, the cartridge assembly 200 is inserted into the cartridge reader unit 100. Optionally, as part of method 400, user instruction may be input to the cartridge reader unit 100 and/or system 300 via the user interface/display 120. Then, at step 425, the processing of sample is initiated via the control unit 310. This initiation may include, for example, receiving input via an operator or user through the user interface/display 120 and/or a system that is connected to the reader unit 100. In another embodiment, processing may be initiated automatically via insertion of the cartridge assembly 200 into the cartridge reader unit 100 and detecting presence of the cartridge assembly 200 therein (e.g., via electrical connection between electrical contact pads 290 on the assembly 200 with the control unit 310, and automatically reading instructions from memory chip 275). The sample is processed at step 425 using pneumatic control instructions (e.g., obtained from memory chip 275) in order to produce a prepared sample. As generally described above (and further later below), the processing of the sample may be dependent upon the type of sample and/or the type of cartridge assembly 200 inserted into the reader unit 100. In some cases, the processing may include a number of steps, including mixing, introduction of buffers or reagents, etc., before the sample is prepared. Once the sample is prepared, the prepared sample is sent (e.g., through channels in the card 210 and to output port 255, via pneumatic control through pneumatic system 330 and control unit 310) to the GMR sensor chip 280. At step 440, analytes in the prepared sample are detected at the GMR sensor chip 280. Then, at step 445, signals from the GMR sensor chip 280 are received and processed, e.g., via cartridge reader 310 (control unit; which may include one or more processors, for example). Once the signals are processed, test results may be displayed at 450, e.g., via the display 120/user interface. At 455, test results are saved. For example, test results may be saved in a cloud server and/or memory chip 275 on board the cartridge assembly 200. In embodiments, any fluids or sample may be directed from the GMR sensor chip 280 through an input port 257 to waste chamber 270. Thereafter, once all tests are preformed and read by the sensing device/GMR sensor chip 280, the cartridge assembly 200 may be ejected from the cartridge reader unit 100. In accordance with an embodiment, this may be automatically performed, e.g., mechanics within the housing 110 of the cartridge reader unit 100 may push the assembly 200 out of the housing 110, or performed manually (by way of a button or force) by the operator, for example.

In an embodiment, the system 300 described herein may utilize a pneumatic control system as disclosed in International Patent App. No. PCT/US2019/043720, entitled "SYSTEM AND METHOD FOR GMR-BASED DETECTION OF BIOMARKERS" filed Jul. 26, 2019, which is hereby incorporated by reference herein in its entirety.

In an embodiment, the system 300 described herein may utilize a cartridge assembly (e.g., for sample preparation and delivery to the sensor(s)) as disclosed in International Patent App. No. PCT/US2019/043753, entitled "SYSTEM AND METHOD FOR SAMPLE PREPARATION IN GMR-BASED DETECTION OF BIOMARKERS" filed Jul. 26, 2019, which is hereby incorporated by reference herein in its entirety.

In an embodiment, the system 300 described herein may sense analytes as disclosed in International Patent App. No. PCT/US2019/043766, entitled "SYSTEM AND METHOD FOR SENSING ANALYTES IN GMR-BASED DETECTION OF BIOMARKERS" filed Jul. 26, 2019, which is hereby incorporated by reference herein in its entirety. For example, in an embodiment, the sensing device, or GMR sensor chip 280, may include one or more microfluidic channels and a plurality of sensor pads disposed within the one or more microfluidic channels as disclosed in the -0504848 application. In an embodiment, such a channel may optionally include a plurality of GMR sensors disposed within a channel. GMR sensors may be all identically configured to detect a single analyte, the redundancy allowing for enhanced detection. GMR sensors may also be all configured differently to detect a myriad of analytes or a combination of differently configured sensors with some redundancies. The configuration of the channel is not limiting. Collectively, the GMR sensors in the channel may be designed to provide the output (test results) from the GMR sensor chip 280.

It should be understood that, with regards to FIGS. 1 and 2A-2D, the features shown are representative schematics of a cartridge reader unit 100 and cartridge assembly 200 that are part of the herein disclosed system 300 for detecting the analyte(s) in a sample. Accordingly, the illustrations are explanatory only and not intended to be limiting.

Figure 5A:
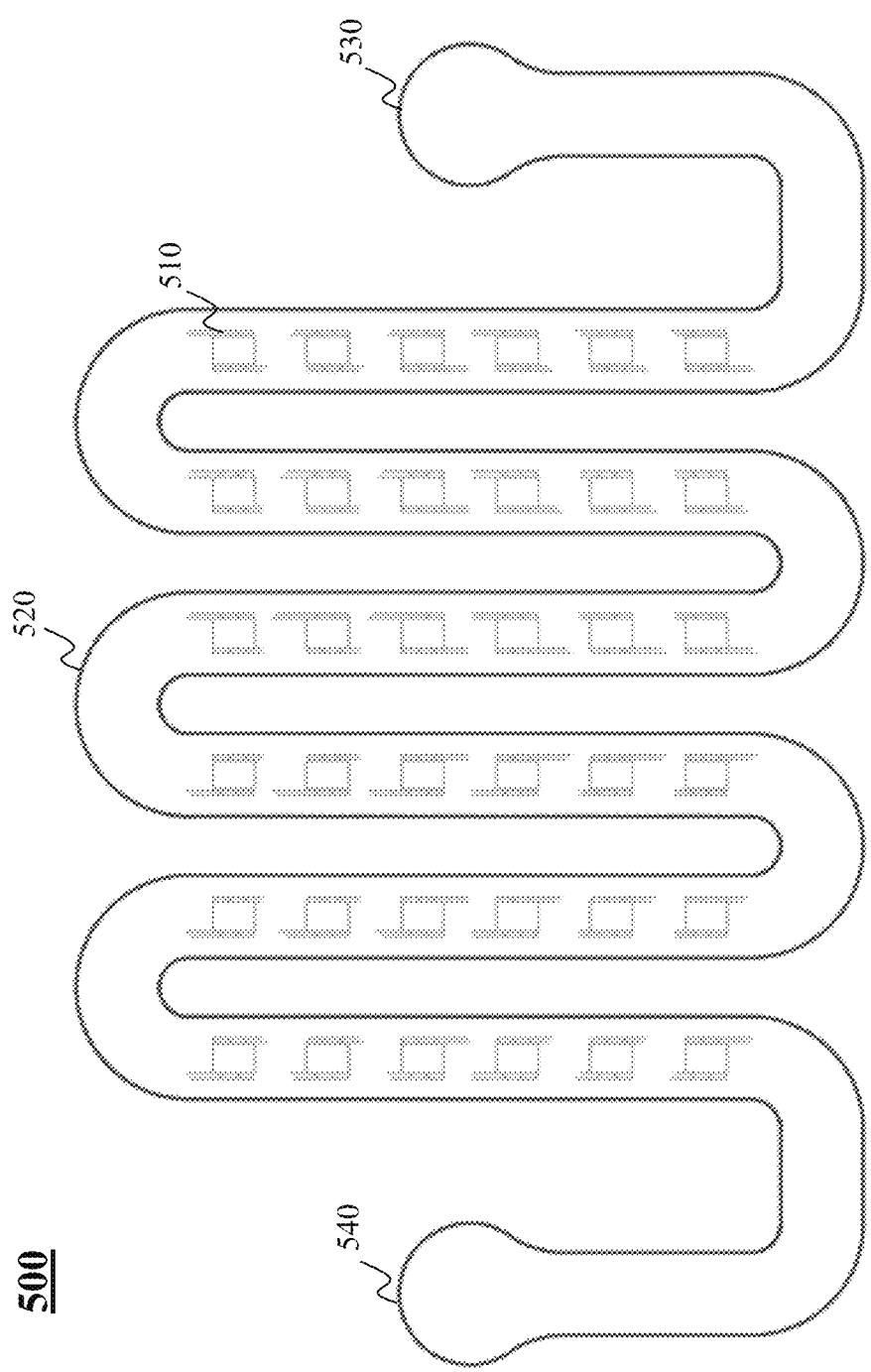
FIG. 5A shows an exemplary channel in accordance with some embodiments.

Referring now to FIG. 5A there is shown an exemplary channel 500 in accordance with some embodiments. Channel 500 is shown as serpentine in structure, but it need not be so limited in geometry. Channel 500 comprises a plurality of GMR sensors 510 disposed within the channel body 520. GMR sensors 510 may be all identically configured to detect a single analyte, the redundancy allowing for enhanced detection. GMR sensors 510 may also be all configured differently to detect a myriad of analytes or a combination of differently configured sensors with some redundancies. Channel 500 further comprises a channel entrance 530 where any samples, reagents, bead suspensions, or the like enter channel body 520. Flow through channel body 520 may be mediated under positive pressure at channel entrance 530 or under vacuum applied at channel exit 540.

Figure 5B:
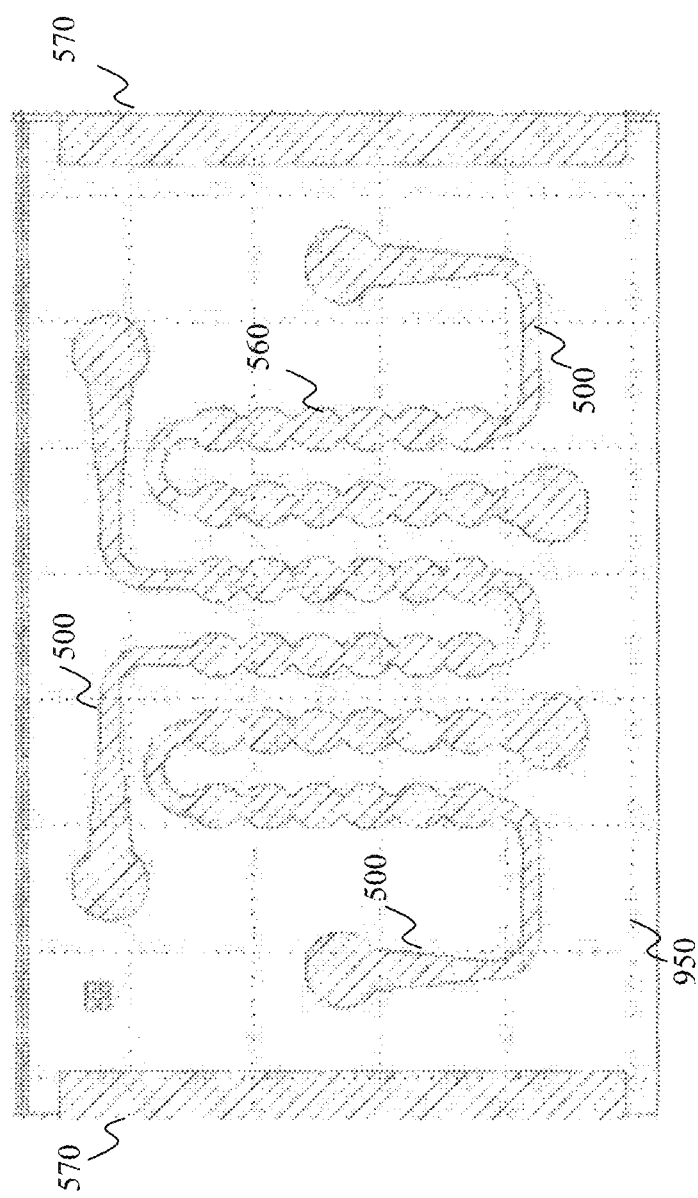
FIG. 5B shows a plurality of channels disposed within a base.

FIG. 5B shows a plurality of channels 500 disposed within base 550. Each channel 500 features channel expansions 560 which is an expanded area surrounding each GMR sensor 510 (FIG. 5A; not shown in FIG. 5B for clarity). Without being bound by theory, it is postulated that channel expansions 560 provide a means for better mixing of materials as they pass over the GMR sensors. At the periphery of base 550 are disposed a pair of contact pads 570 which serve as an electrical conduit between the GMR sensors located in channel expansions 560 and the rest of the circuitry. GMR sensors 510 are electronically linked via wiring (not shown) to contact pads 570.

Figure 6A:
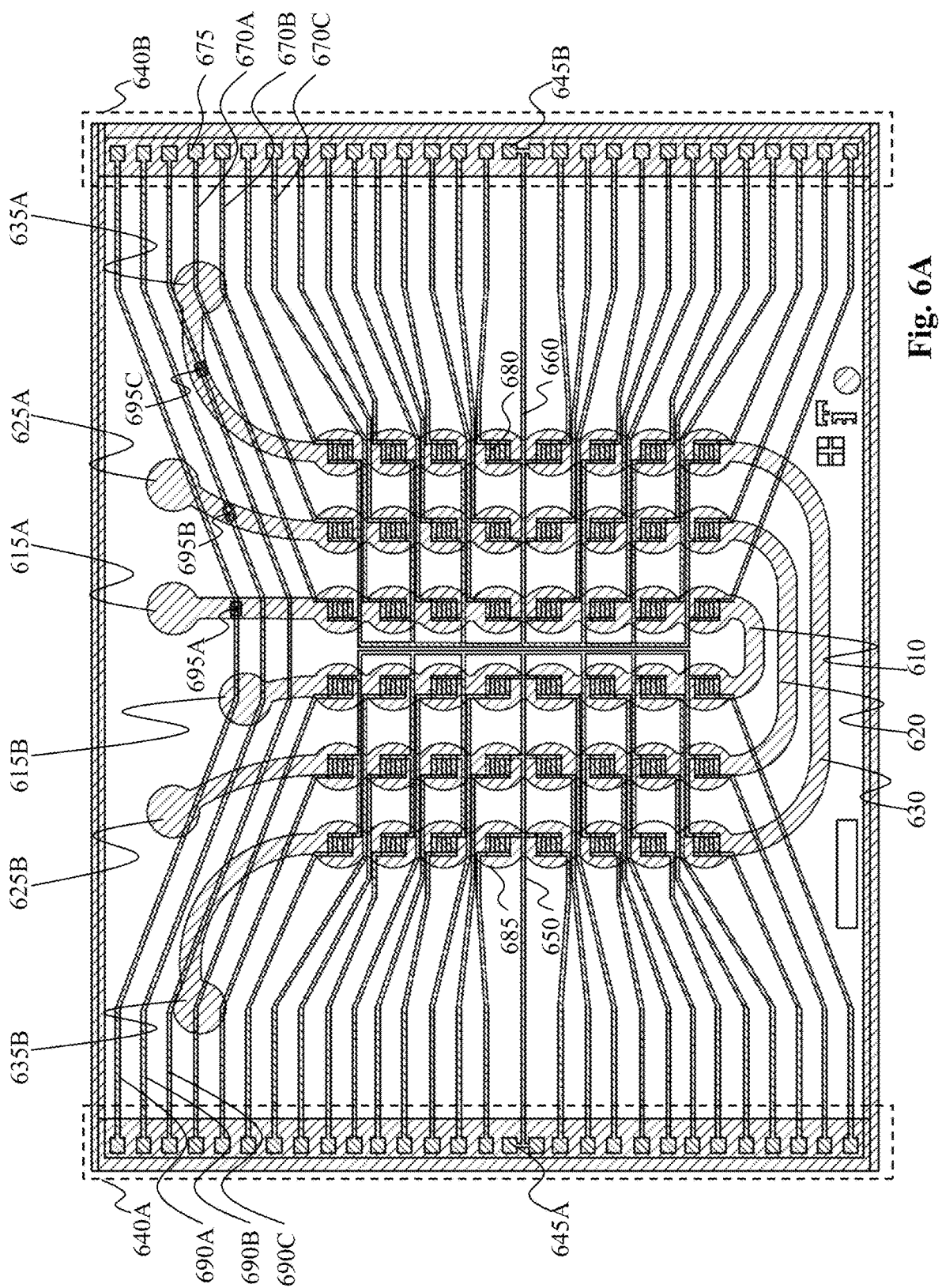
FIGS. 6A-6C schematically illustrate the structure of a GMR sensor chip which can be mounted on the cartridge assembly according to an embodiment of the present disclosure.
Figure 6B:
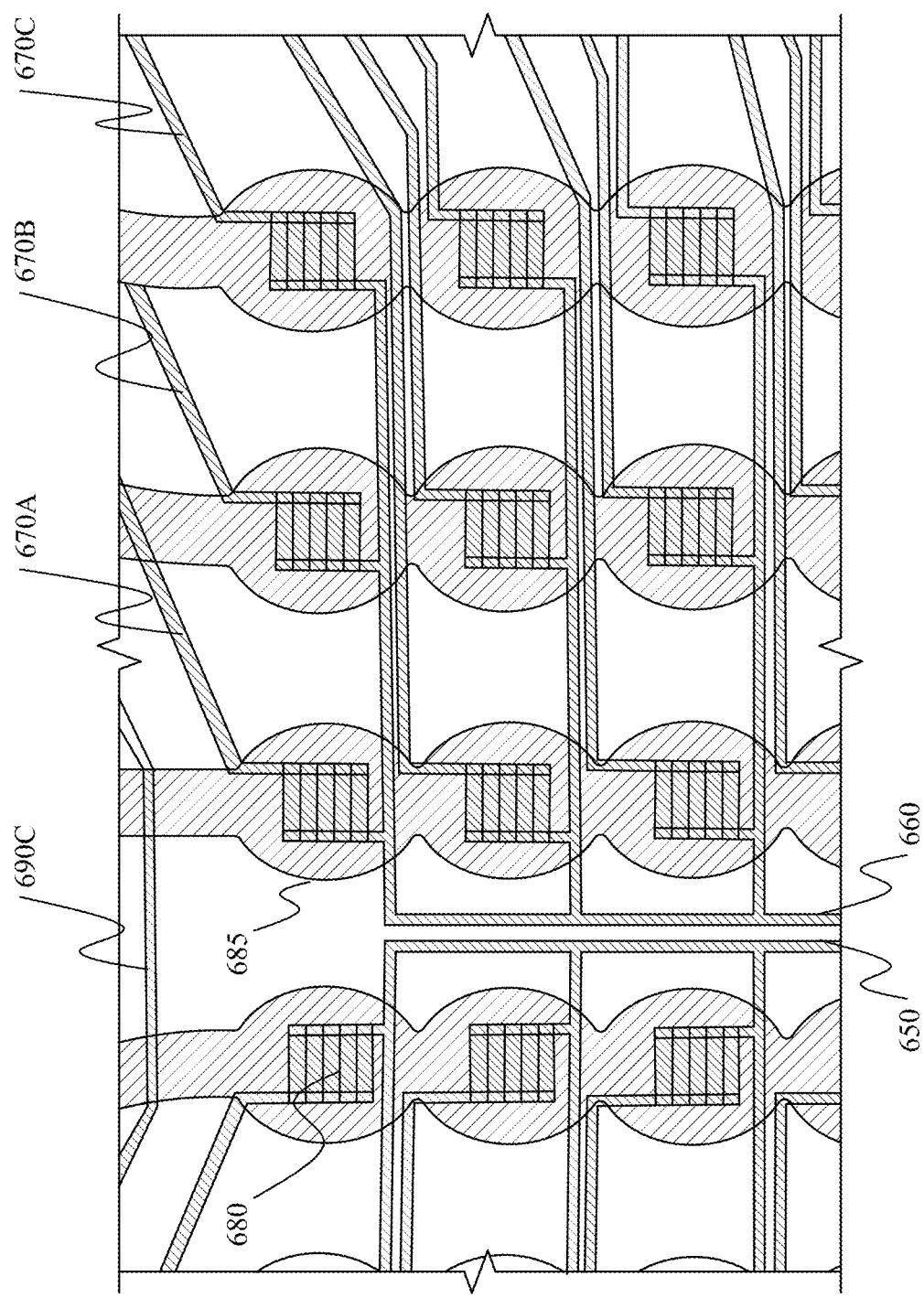
Figure 6C:
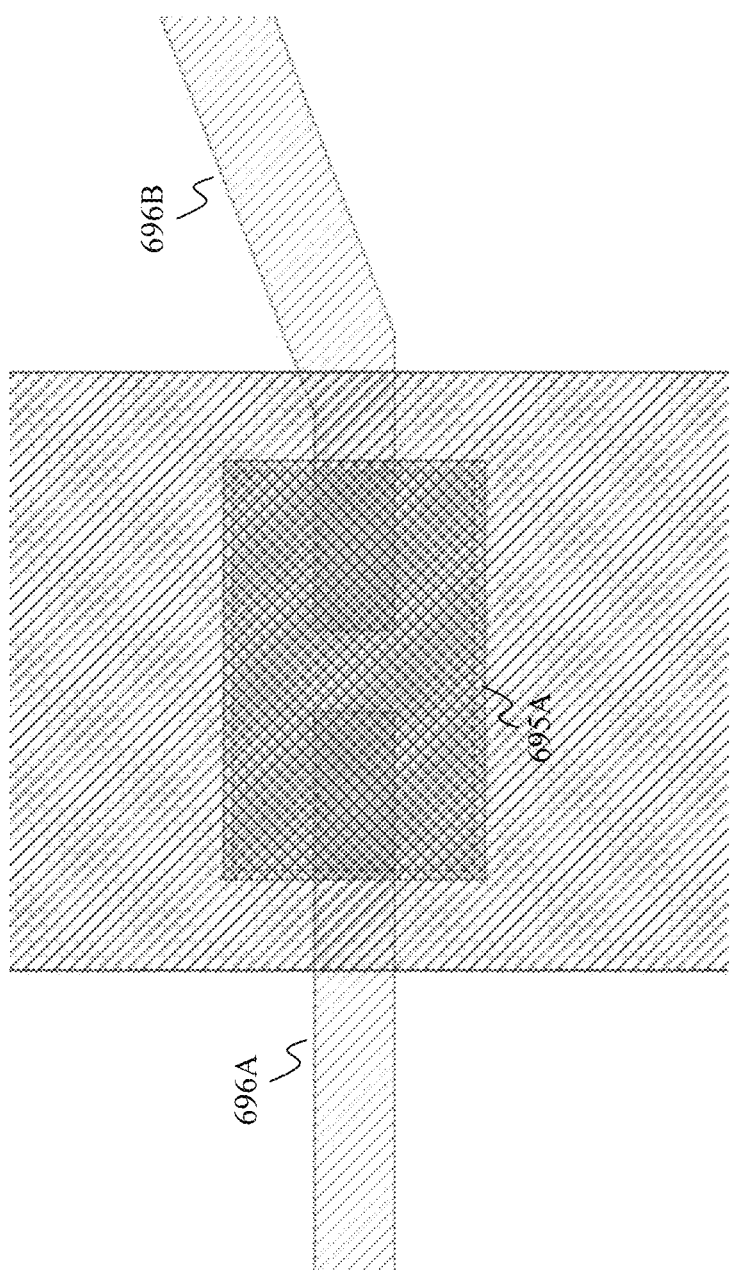

FIGS. 6A, 6B and 6C schematically illustrate the structure of a GMR sensor chip 280 which can be mounted on the cartridge assembly 200 according to an embodiment of the present disclosure. As shown in FIG. 6A, the GMR sensor chip 280 includes: at least one channels 610, 620 and 630 arranged approximately in the center of the chip; a plurality of GMR sensors 680 disposed within the channels; electric contact pads 640A, 640B arranged on two opposing ends of the GMR sensor chip; and metal wires 650, 660, 670A, 670B, 670C, 690A, 690B, 690C coupled to the electric contact pads 640A, 640B.

The channels 610, 620 and 630 each can have a serpentine shape to allow for more sensors to be packed inside. A plurality of channel expansions 685 can be arranged along the channels to receive the plurality of GMR sensors. Fluid to be tested flows into and out of the channels 610, 620, 630 via channel entrances 615A, 625A, 635A and channel exits 615B, 625B, 635B, respectively. Although FIG. 6A shows that the GMR sensors 680 are arranged in an 8×6 sensor array, with 16 sensors received in each of three channels 610, 620, 630, other combinations can be used to satisfy the specific needs of the analyte to be sensed.

The electric contact pads 640A, 640B comprise a plurality of electric contact pins. The metal wires 650, 660, 670A, 670B, 670C connect the GMR sensors to corresponding electric contact pins 645A, 645B, 675. The electric contact pads 640A, 640B are in turn connected to the electrical contact pads 290 provided on the cartridge assembly 200. When the cartridge assembly 200 is inserted to the cartridge reader 310, electric connection is formed between the GMR sensor chip 280 and the cartridge reader 310 to enable sending of measurement signals from the GMR sensors to the cartridge reader 310.

FIG. 6B shows more details of the GMR sensors. For example, each GMR sensor can be comprised of five GMR strips which are connected in parallel. At one end, each GMR sensor is connected by one of two main metal wires (i.e., either wire 650 or 660) to one of two common pins (i.e., either pin 645A or 645B). The other ends of the GMR sensors are connected by separate metal wires 670A, 670B, 670C to distinct pins 675 on the electric contact pads 640A or 640B.

FIG. 6A also shows fluid detection metal wires 690A, 690B, 690C which are arranged in the proximity of the channel entrances and/or exits, each corresponding to one of the channels. The fluid detection function is carried out by switches 695A, 695B, 695C arranged in the respective fluid detection metal wires. FIG. 6C shows the structure of the switch 695A in detail. In response to recognition that conductive fluid (for example, plasma) flows over it, the switch 695A can couple the wire 696A on one side to the wire 696B on the other side, generating a fluid detection signal.

Figure 7:
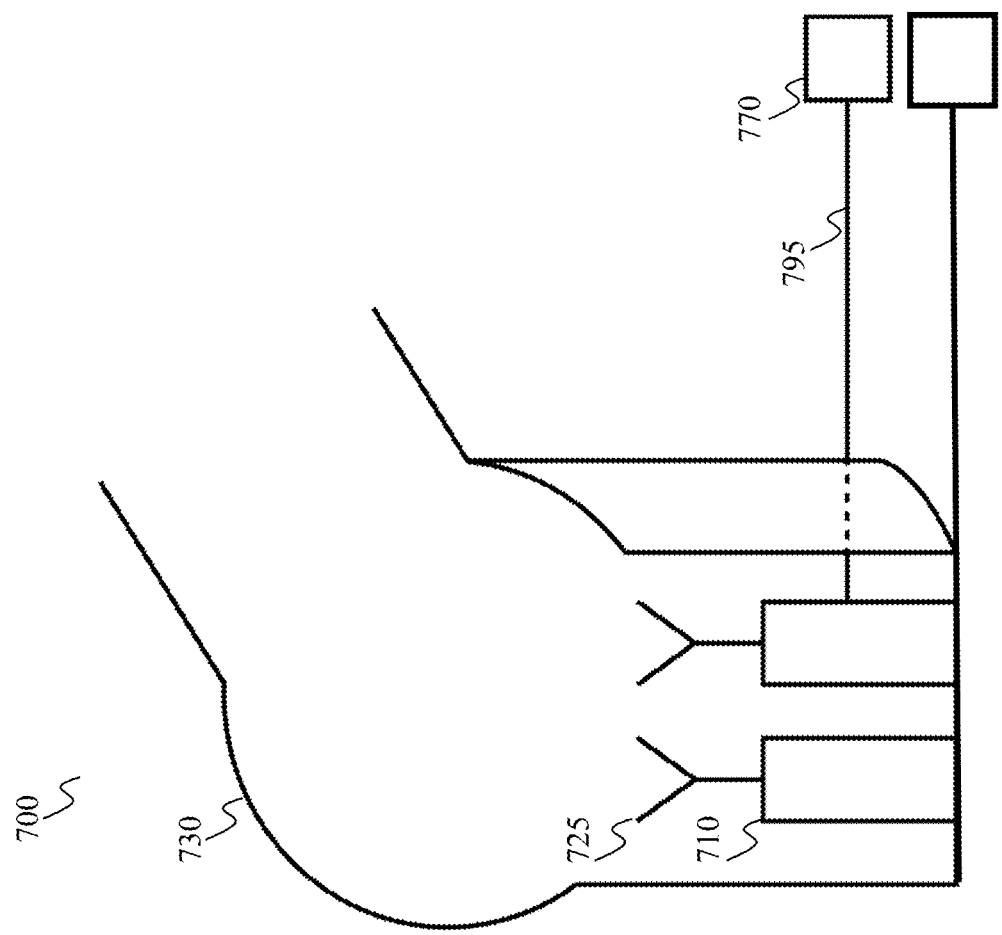
FIG. 7 shows a cross-sectional view of a channel at a channel expansion.

The structure and wiring of the GMR sensor chip shown in FIGS. 6A-C are only exemplary in nature, it will be apparent to those skilled in the art that other structures and wirings are feasible to achieve the same or similar functions. Referring now to FIG. 7, there is shown a cross-sectional view of channel 700 at a channel expansion 730. Disposed within channel expansion 730 is GMR sensor 710 on which is immobilized one or more biomolecules 725. Immobilization of biomolecule 725 to GMR sensor 710 is via conventional surface chemistry (shown in some further detail in FIG. 8). Biomolecule 725 may be a peptide or protein, DNA, RNA, oligosaccharide, hormone, antibody, glycoprotein or the like, depending on the nature of the specific assay being conducted. Each GMR sensor 710 is connected by wire 795 to a contact pad 770 located outside of channel 700. In some embodiments, wire 795 is connect to GMR sensor 710 at the bottom of the sensor.

Figure 8A:
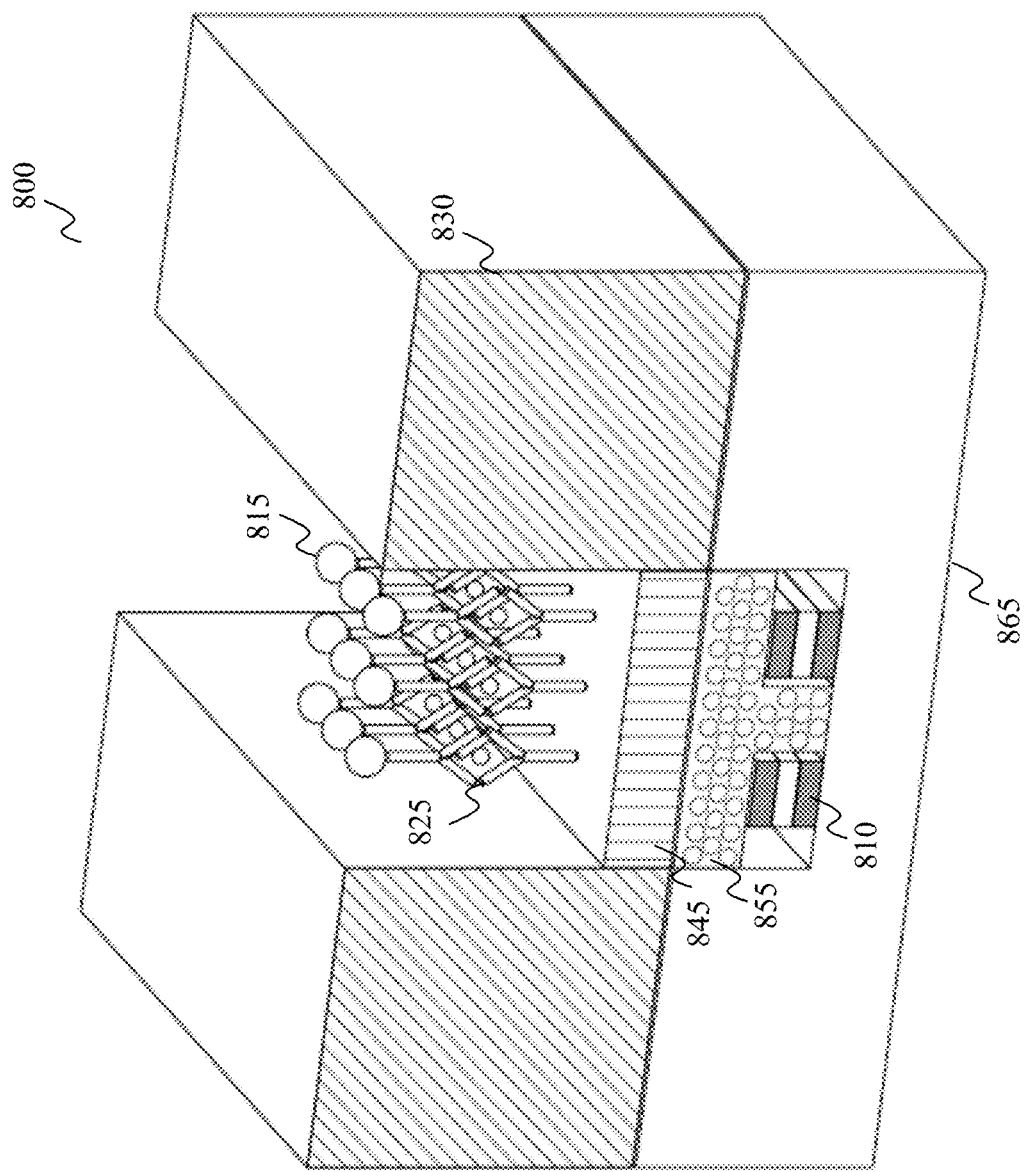
FIG. 8A shows a more detailed cross-sectional view of a channel having a channel body lacking a channel expansion at the location of a GMR sensor.

Referring now to FIG. 8A, there is shown a more detailed cross-sectional view of a channel 800 having a channel body 830 lacking a channel expansion at the location of a GMR sensor 810. Biomolecule 825 is immobilized with respect to the sensor via attachment to a biosurface 845. Such biosurface immobilization chemistry is known in the art. See, for example, Cha et al. "Immobilization of oriented protein molecules on poly(ethylene glycol)-coated Si(111)," *Proteomics* 4:1965-1976, (2004); Zellander et al. "Characterization of Pore Structure in Biologically Functional Poly(2-hydroxyethyl methacrylate)-Poly(ethylene glycol) Diacrylate (PHEMA-PEGDA)," *PLOS ONE* 9(5):e96709, (2014). In some embodiments, biosurface 845 comprises a PEG polymer crosslinked with PHEMA. In some embodiments, the crosslinking group is represented by Formula (I):

PA-LG-PA  (I)

wherein each PA is a photo- or metal-activated or activated group, and LG is a linking group. In some embodiments, each PA is the same and in other embodiments each PA is different. In some embodiments PA is photo- or metal-activated to form a nitrene intermediate capable of C—H and/or O—H insertion. See, for example, "Photogenerated reactive intermediates and their properties," Chapter 2 in *Laboratory Techniques in Biochemistry and Molecular Biology*, Elsevier Press, 12:8-24 (1983). In some embodiments, PA is metal activated to form a carbene or carbenoid intermediate capable of C—H and/or O—H insertion. See, for example, Doyle et al. "Catalytic Carbene Insertion into C—H Bonds," *Chem. Rev.* 2:704-724 (2010).

In some embodiments, each PA is an azide ($—N_3$) moiety and photoactivation generates nitrene intermediates capable of C—H and/or O—H insertion thereby mediating crosslinking of PEG and PHEMA polymers. In some embodiments, each PA is a diazo ($—N_2$) and metal catalyzed decomposition reaction forms a carbene or carbenoid intermediate capable of C—H and/or O—H insertion thereby mediating crosslinking of PEG and PHEMA polymers. Both azide and diazo preparations are well known in the art, and in the case of azide are readily prepared by $S_N^2$ displacement reaction of azide anion, $N_3^-$ with an appropriate organic moiety possessing a leaving group.

LG in Formula (I) can be any organic fragment that will support the presence of each PA moiety. It can be a simple $C_2$-$C_{20}$ hydrocarbon chain that is straight chained or branched. Such hydrocarbons can include fluorinated variants with any degree of fluorine substitution. In some embodiments, LG can include aromatic hydrocarbons including, without limitation, benzene, naphthalene, biphenyl, binaphthyl, or combinations of aromatic structures with $C_2$-$C_{20}$ hydrocarbon chains. Thus, in some embodiments, LG can be alkyl, aryl, or aralkyl in structure. In some embodiments, alkyl linking groups may have one or more carbons in their chains substituted with oxygen (O), or an amine (NR), where R is H or $C_1$-$C_6$ alkyl.

In accordance with the foregoing embodiments, a crosslinked PEG-PHEMA structure may be given by Formula (II):

PEG-A-LG-A-PHEMA

Wherein PEG is the polyethylene glycol moiety, each A is an attachment atom from the catalytic reaction of azide or diazo, i.e., $CH_2$ or NH, and LG is the linking group as described above.

In FIG. 8A, a magnetic bead-bound entity 815 is configured to interact with biomolecule 825 or an analyte of interest, such as in a sandwich complex of antibody-analyte-magnetic bead-bound antibody. Below biosurface 845 is a further insulating layer 855. Insulating layer 855 may be in direct contact with GMR sensors 810 and may comprise, for example, a metal oxide layer. Biosurface layer 845 is in direct contact with insulating layer 845. A base 865 serves as the scaffold for each component above it, the GMR sensors 810, insulating layer 855, and biosurface layer 845. In some embodiments, base 865 is made from silicon wafer.

Figure 8B:
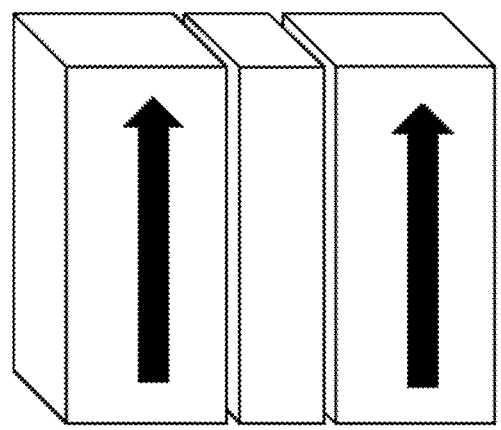
FIG. 8B schematically illustrates the basic structure and principle of GMR sensors.
Figure 8B:
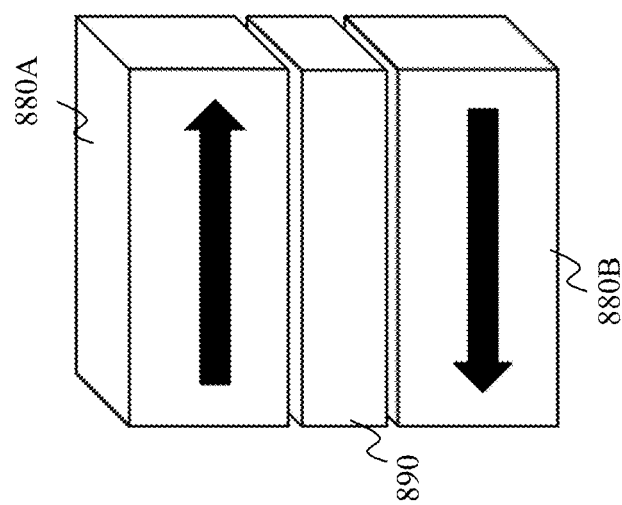

FIG. 8B schematically illustrates the basic structure and principle of GMR sensors. A typical GMR sensor consists of a metallic multi-layered structure with a non-magnetic conductive interlayer 890 sandwiched between two magnetic layers 880A and 880B. The non-magnetic conductive interlayer 890 is often a thin copper film. The magnetic layers 880A and 880B can be made of ferromagnetic alloy material.

The electrical resistance of the metallic multi-layered structure changes depending on the relative magnetization direction of the magnetic layers 880A and 880B. Parallel magnetization (as shown in the right half of FIG. 8B) results in lower resistance, while anti-parallel magnetization (as shown in the left half of FIG. 8B) results in higher resistance. The magnetization direction can be controlled by a magnetic field applied externally. As a result, the metallic multi-layered structure displays a change in its electrical resistance as a function of the external magnetic field.

GMR sensors have sensitivities that exceed those of anisotropic magnetoresistance (AMR) or Hall sensors. This characteristic enables detection of stray fields from magnetic materials at nanometer scales. For example, stray fields from magnetic nanoparticles that bound on sensor surface will alter the magnetization in the magnetic layers, and thus change the resistance of the GMR sensor. Accordingly, changes in the number of magnetic nanoparticles bound to the GMR sensor per unit area can be reflected in changes of the resistance value of the GMR sensor.

Figure 9A:
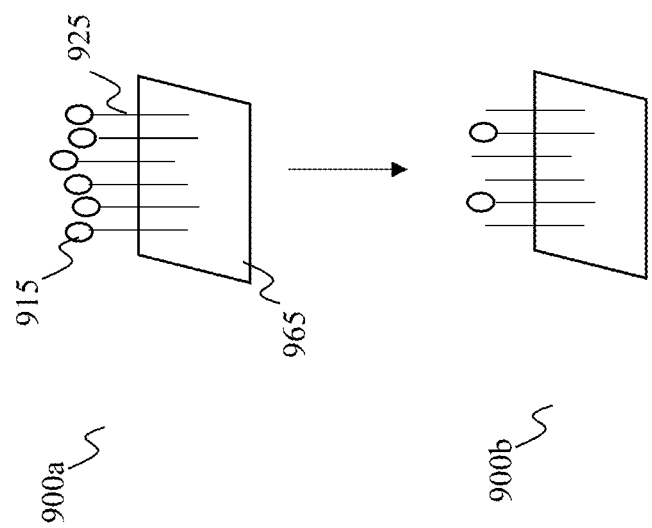
FIG. 9A shows an exemplary basic mode by which GMR sensors operate in accordance with various assay applications described herein.
Figure 10A:
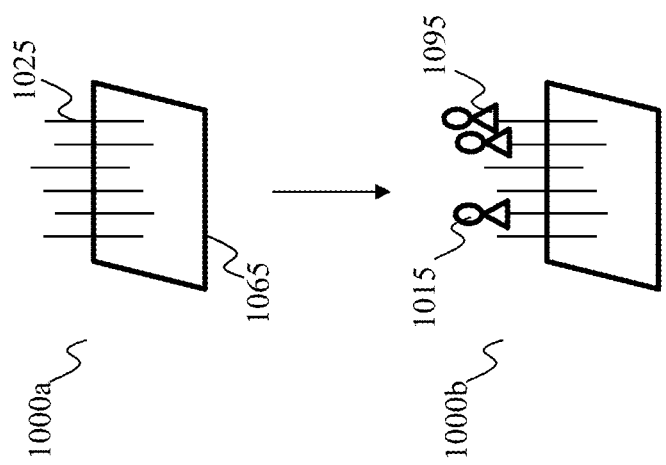
FIG. 10A shows another exemplary basic mode by which GMR sensors operate in accordance with various assay applications described herein.

Referring now to FIGS. 9A and 10A, there are shown two exemplary basic modes by which GMR sensors operate in accordance with various assay applications described herein. In the first mode, exemplified in FIG. 9A, magnetic beads 915 are loaded proximal to a GMR sensor (see FIG. 8A, 810) via biosurface 965 at the start of the assay. During the assay the presence of a query analyte results in magnetic beads 915 being displaced from biosurface 965 (and thus, displaced away from the GMR sensor); this mode is the so-called subtractive mode because magnetic beads are being taken away from the proximity of the sensor surface. The second main mode operation, typified in FIG. 10A, is the additive mode. In such assays, there is a net addition of magnetic beads 1015 in the vicinity of the GMR sensor (see FIG. 8A, 810) when a query analyte is present. Either mode, subtractive or additive, relies on the changed state in the number of beads (915, 1015) proximal to the sensor surface thereby altering the resistance in the GMR sensor system. The change in resistance is measured and query analyte concentrations can be determined quantitatively.

Referring back to FIG. 9A, there is shown a sensor structure diagram illustrating the sensor structures throughout an exemplary subtractive process. At the start of the process the system is in state 900a in which the GMR sensor has disposed on its biosurface 965 a plurality of molecules (typically biomolecules) 925 with associated magnetic beads 915. The volume above biosurface 965 may begin dry or with a solvent present. When dry, the detection process may include a solvent priming step with, for example, a buffer solution. After introduction of analyte, the system takes the form of state 900b in which some of magnetic beads 915 have been removed from the molecules 925 in proportion to the concentration of analyte. The change in states 900a and 900b provide a measurable change in resistance that allows quantitation of the analyte of interest. In some embodiments, the analyte may simply displace beads directly from molecules 925. In other embodiments, the analyte may chemically react with molecules 925 to cleave a portion of the molecule attached to beads 915, thereby releasing beads 915 along with the cleaved portion of molecule 925.

In embodiments, biosurface 965 comprises a polymer. The specific polymer may be chosen to facilitate covalent attachment of molecules 925 to biosurface 965. In other embodiments, molecules 925 may be associated with biosurface 965 via electrostatic interactions. Polymer coatings may be selected for or modified to use conventional linking chemistries for covalently anchoring biomolecules, for example. Linking chemistries include any chemical moieties comprising an organic functional group handle including, without limitation, amines, alcohols, carboxylic acids, and thiol groups. Covalent attachment chemistry includes, without limitation, the formation of esters, amides, thioesters, and imines (which can be subsequently subjected to reduction, i.e., reductive amination). Biosurface 965 may include surface modifiers, such as surfactants, including without limitation, anionic surfactants, cationic surfactants, and zwitterionic surfactants.

In embodiments, magnetic beads 915 may be nanoparticulate, including spheroidal nanoparticles. Such nanoparticles may have effective diameters in a range from about 2 to about 50 nanometers (nm), or about 5 to about 20 nm, or about 5 to about 10 nm. In embodiments, magnetic beads 915 may be coated to facilitate covalent attachment to molecules 925. In other embodiments magnetic beads 915 may be coated to facilitate electrostatic association with molecules 925. Magnetic beads 915 may be differentially tagged and/or coated to facilitate multiplex detection schemes. In such embodiments, the differential tagging and/or coating is configured such that the different beads interact with different molecules disposed on different GMR sensors or on a single sensor in which different molecules are spatially organized to create addressable signals.

Figure 9B:
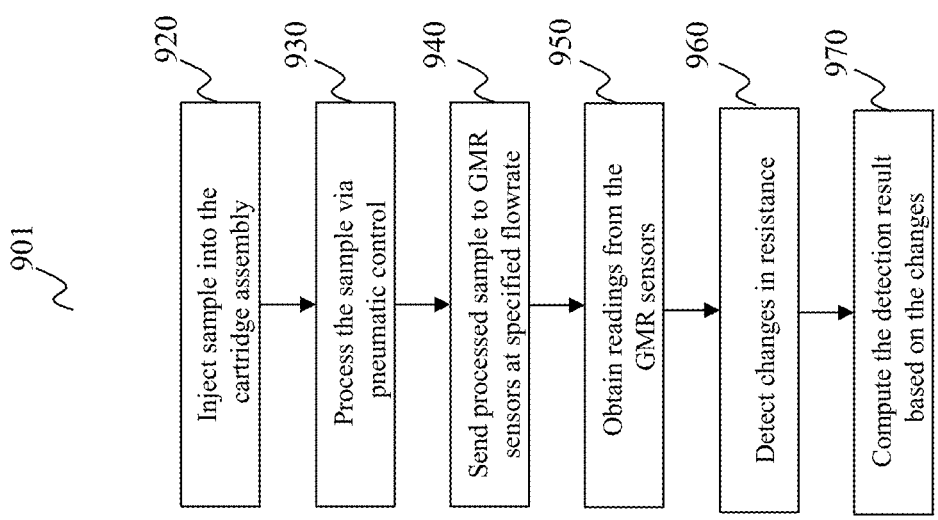
FIG. 9B shows a process flow associated with the sensor structure scheme of FIG. 9A.

FIG. 9B shows a process flow 901 associated with the sensor structure scheme of FIG. 9A. The process commences at 920 by injecting a sample into a cartridge assembly. The sample may then undergo processing at step 930 through any necessary steps such as filtration, dilution, and/or chemical modification. The sequencing of these pre-process steps will depend on the nature of the sample and query analyte to be detected. Movement through the system may be controlled pneumatically. Step 940 involves sending the processed sample to the GMR sensor at a target specified flow rate. Such flow rate may be selected to reflect the kinetics of the chemistry on the GMR sensor surface. Step 950 provides obtaining readings from the GMR sensors that reflect changes in the concentration of magnetic beads at the surface of the GMR sensor. These readings allow detecting changes in resistance at step 960. Finally, step 970 provides computing the detect result based on the changes in resistance.

Referring now to FIG. 10A, there is shown a sensor structure diagram illustrating the sensor structures throughout an exemplary additive process. At the start of the process the system is in state 1000a in which the GMR sensor has disposed on its biosurface 1065 a plurality of molecules (typically biomolecules) 1025. The plurality of molecules 1025 is selected to bind a query analyte 1090, as indicated in second state 1000b. Query analyte 1095 is configured to bind magnetic beads 1015. In some embodiments, query analyte 1095 is associated with the bead prior to passing over biosurface 1065. For example, this may take place during pre-processing of the sample being tested. (In other embodiments, query analyte 1095 may pass over the biosurface first, then query analyte 1095 may be modified with magnetic beads 1015 after the analyte is bound to biosurface 1065, as described below with reference to FIG. 17A). In some embodiments, a given query analyte 1095 may require chemical modification prior to binding magnetic particles 1015. In some embodiments, magnetic beads 1015 may be modified to interact with query analyte 1095. The ability to quantitate analyte is provided by changes in measured resistance from state 1000a, where no magnetic beads 1015 are present, to state 1000b, where magnetic beads 1015 are associated with biosurface 1065.

Figure 10B:
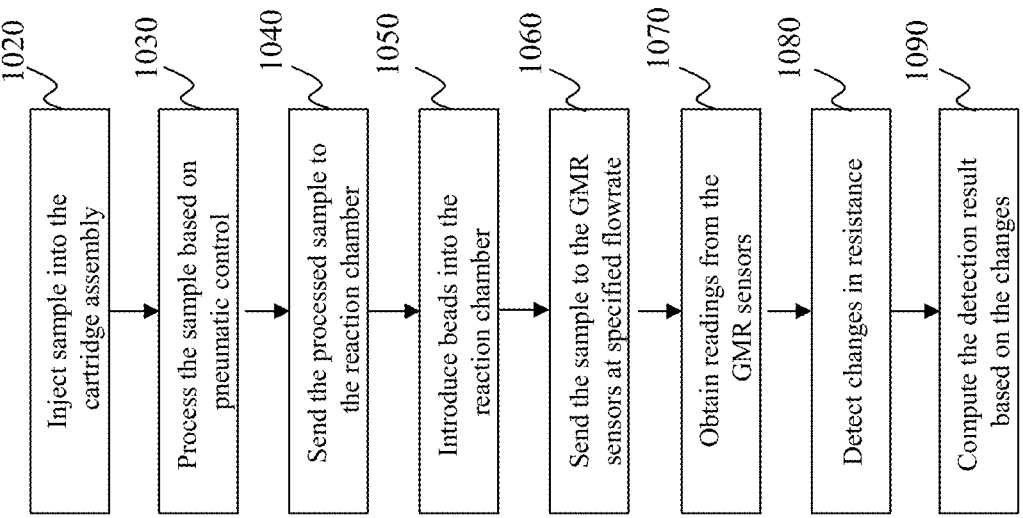
FIG. 10B shows a process flow associated with the sensor structure scheme of FIG. 10A.

FIG. 10B shows an exemplary process flow 1001 associated with the sensor structure scheme of FIG. 10A. The process commences at 1020 by injecting a sample into a cartridge assembly. The sample may then undergo processing at step 1030 through any necessary steps such as filtration, dilution, and/or chemical modification. The sequencing of these pre-process steps will depend on the nature of the sample and query analyte to be detected. Movement through the system may be controlled pneumatically. Step 1040 involves sending the processed sample to a reaction chamber and then at step 1050 beads are introduced into the reaction chamber to modify the query analyte. As described above, such modification may be performed directly on the sensor surface rather than in the reaction chamber. At step 1060, the modified sample is sent to the GMR sensors at a target flow rate. Such flow rate may be selected to reflect the kinetics of the chemistry on the GMR sensor surface. Step 1070 provides obtaining readings from the GMR sensors that reflect changes in the concentration of magnetic beads at the surface of the GMR sensor. These readings allow detecting changes in resistance at step 1080. Finally, step 1090 provides computing the detect result based on the changes in resistance.

Figure 11A:
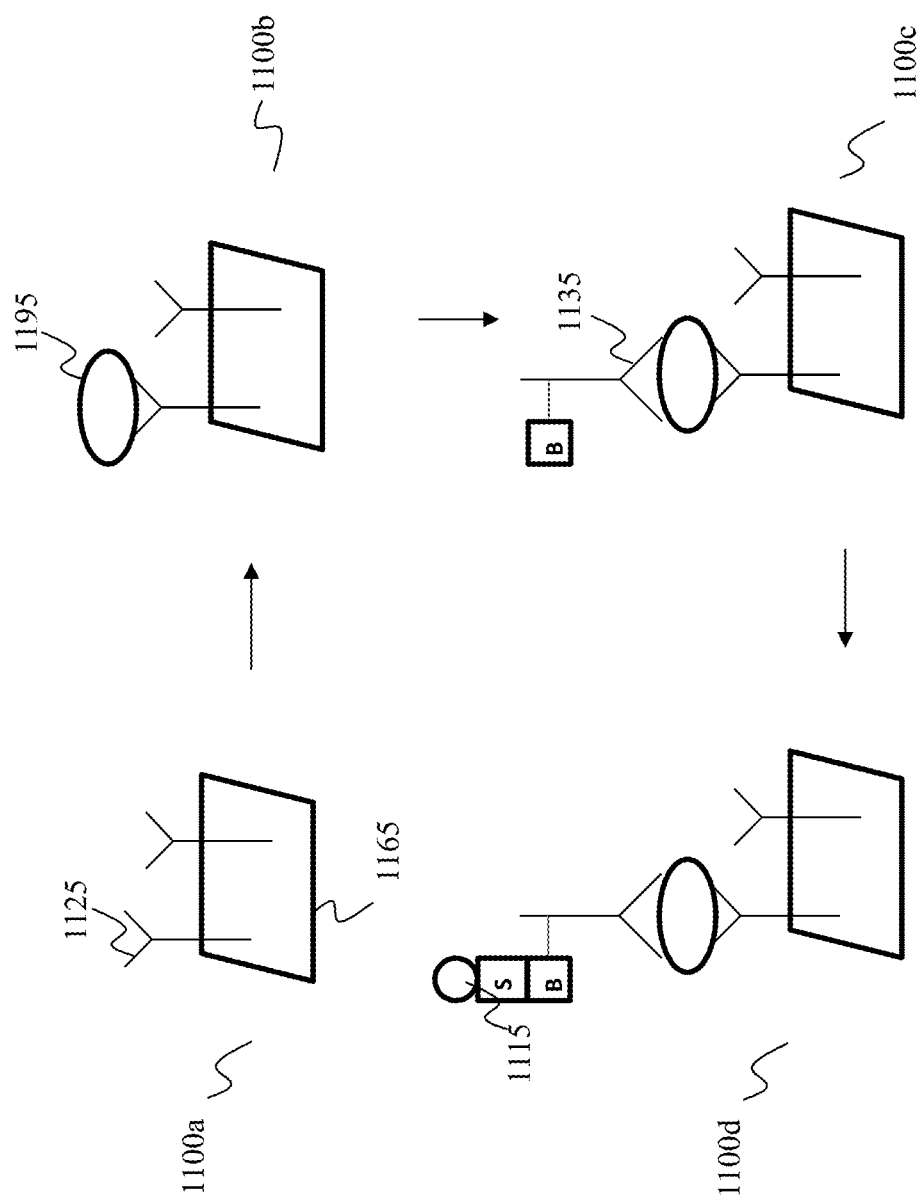
FIG. 11A shows a sensor structure diagram illustrating the sensor structure states throughout an exemplary additive process that employs a sandwich antibody strategy for analyte detection.

Referring now to FIG. 11A, there is shown a sensor structure diagram illustrating the sensor structure states 1100a-d throughout an exemplary additive process that employs a sandwich antibody strategy for detection of analyte 1195 (state 1100b). At the start of the process the system is in state 1100a in which the GMR sensor has disposed on its biosurface 1165 a plurality of antibodies 1125. Analyte 1195 is then passed over biosurface 1165, allowing binding of analyte 1195 to antibody 1125, as indicated in state 1100b. Analyte 1195 is then modified by binding to a second antibody 1135 to which a covalently linked biotin moiety (B) is provided, as indicated in state 1100c. Magnetic beads 1115 modified with streptavidin (S) are then added, thereby allowing the strong biotin-streptavidin association to provide state 1100d. In some embodiments, streptavidin is provided as a coating on magnetic beads 1115.

Figure 11B:
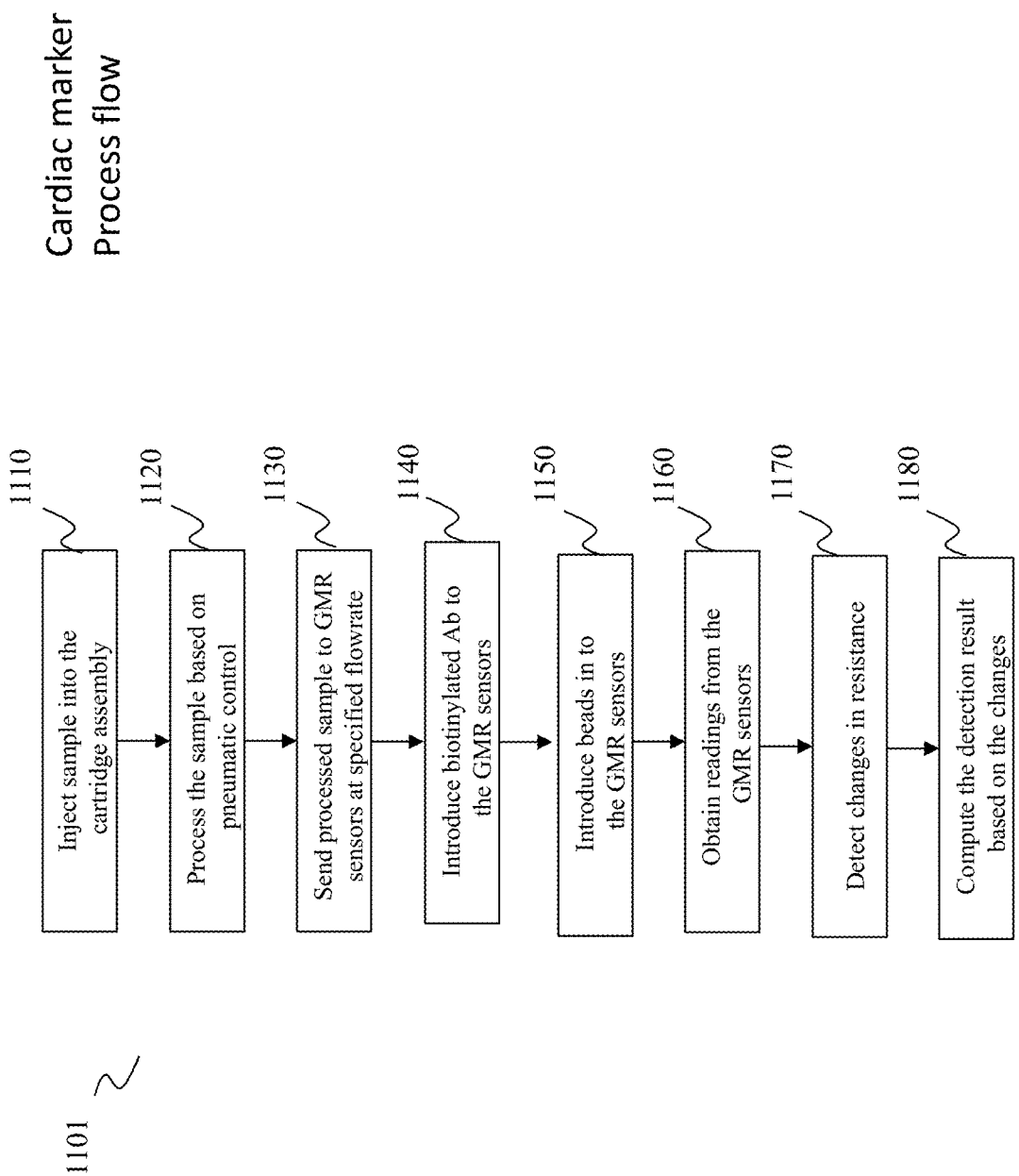
FIG. 11B shows an exemplary process flow associated with the sensor structure scheme of FIG. 11A.

FIG. 11B shows an exemplary process flow 1101 associated with the sensor structure scheme of FIG. 11A. The process commences at 1110 by injecting a sample into a cartridge assembly. The sample may then undergo processing at step 1120 through any necessary steps such as filtration, dilution, and/or the like. The sequencing of these pre-process steps will depend on the nature of the sample and query analyte to be detected. Movement through the system may be controlled pneumatically. At step 1130, the processed sample is sent to GMR sensors at a specified flowrate. Such flow rate may be selected to reflect the kinetics of the chemistry on the GMR sensor surface between biosurface-bound antibody and the analyte. Next, step 1140 introduces biotinylated antibody (Ab) to the GMR sensors. This creates the "sandwich" structure of the analyte between two antibodies. At step 1150 streptavidin coated beads are introduced into the GMR sensors, which can now interact with the biotin-bound antibody. Step 1160 provides obtaining readings from the GMR sensors that reflect changes in the concentration of magnetic beads at the surface of the GMR sensor. These readings allow detecting changes in resistance at step 1170. Finally, step 1180 provides computing the detect result based on the changes in resistance.

Figure 12A:
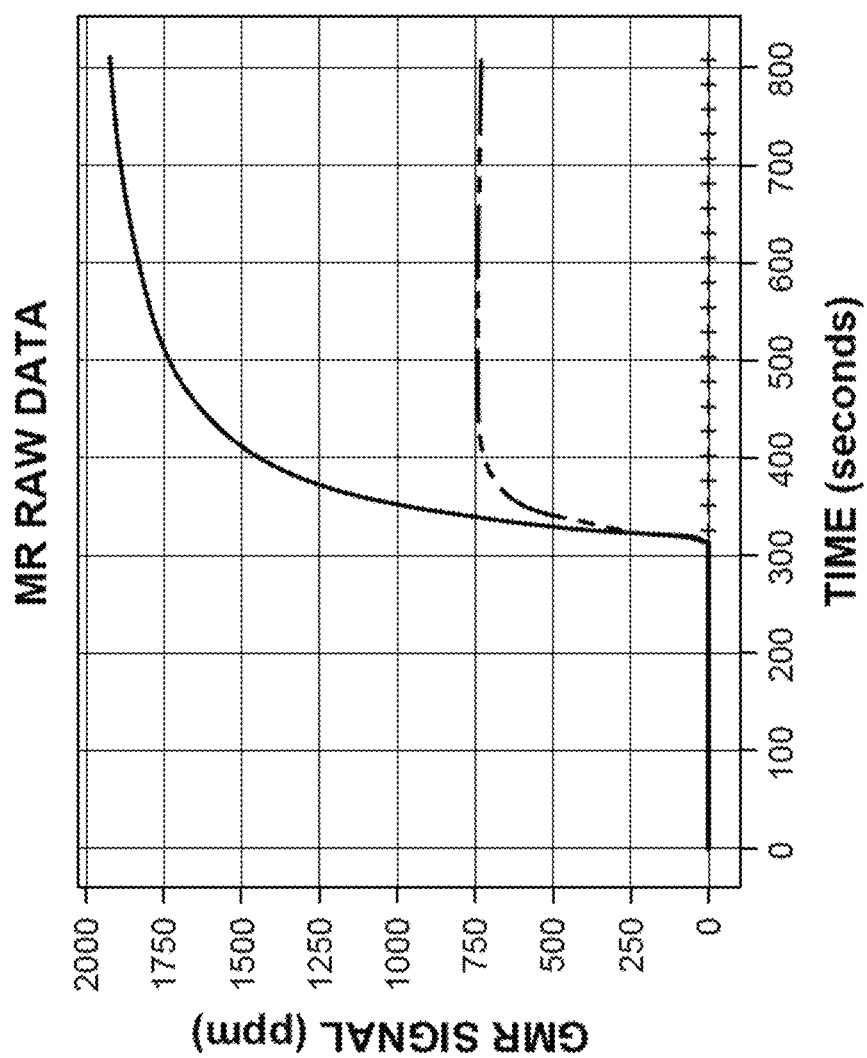
FIG. 12A shows a plot of GMR signal (in ppm) over time (in seconds) in a test run designed to detect cardiac biomarker D-dimer.
Figure 12B:
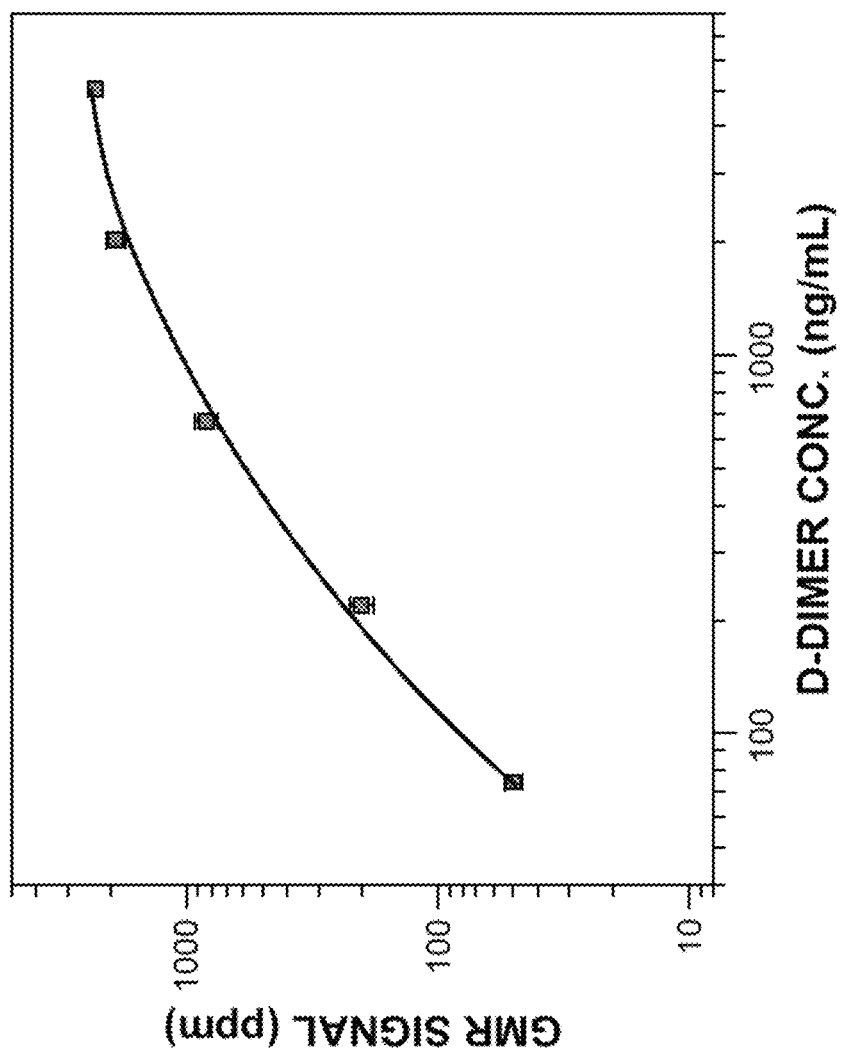
FIG. 12B shows a calibration curve (GMR signal in ppm vs. D-dimer concentration) for D-dimer by running samples with varied, fixed concentrations of D-dimer.

The schemes of FIGS. 11A and 11B were put into practice with cardiac biomarkers and proof of concept results are shown in FIGS. 12A-C. FIG. 12A shows a plot of GMR signal (in ppm) over time (in seconds) in a test run designed to detect cardiac biomarker D-dimer. To generate this data, a biosurface was prepared by printing a D-dimer capture antibody using 2 nL of a 1 mg/mL of D-dimer antibody in PBS buffer with 0.05% sodium azide. For testing potential cross reactivity, the biosurface was also functionalized with troponin I capture antibody by printing two combined capture antibodies using 2 nL of a solution of 1 mg/mL troponin I antibody in PBS buffer with 0.05% sodium azide. Additionally, two other controls were printed on the biosurface. The first is a negative control prepared by printing 2 nL of a solution of 0.5% BSA in PBS buffer with 0.05% sodium azide and the second is a positive control prepared by pringint 2 nL of 1 mg/mL of biotin conjugated to mouse IgG in PBS buffer with 0.05% sodium azide. The printed sensors were incorporated into a cardiac test cartridge and is configured to use the "sandwich" assay described above in FIGS. 11A and 11B.

In the sample test 120 microliters of plasma or whole blood was loaded into a sample well in the cartridge. A membrane filter serves to remove blood cells as the sample is pulled into the flow channel from the sample well. 40 microliters of plasma (or plasma portion of whole blood) is flowed into a metering channel and deposited powder including antibody/biotin conjugates, blockers, and mouse IgG in the channel dissolve into the sample solution. While flowing over the sensor area, the analytes, antibody/biotin conjugates and antibodies immobilized on the sensor surface form a sandwich of antibody-analyte-biotinylated antibody. Flow rates are modulated depending on the test. For troponin I, the sample is flowed over the sensor for 20 minutes at a flow rate of 1 microliter/minute. For D-dimer, the sample is flowed for 5 minutes at a flow rate of 4 microliters/minute. Following flow of the sample streptavidin-coated magnetic beads were introduced which allow binding to the sensor surface wherever there is a biotinylated antibody bound. The GMR sensor measure bound magnetic beads, which is proportional to the concentration of analytes with the sample. The bead solution is flowed over the sensor for 5 minutes at a flow rate of 4 to 10 microliters/minute. The signals were read from the peak value within 300 seconds after beads started to bind.

As indicated in the plot of FIG. 12A, a negative control with just printed BSA did not bind D-Dimer and thus, the signal remained near baseline as expected. The positive control with biotinylated mouse showed competent bead binding, as expected. A plot of the actual sample of 666.6 ng/mL of human D-dimer appears with a peak detection signal of about 750 ppm indicating successful detection of the D-dimer in an actual sample. There was no virtually no cross reactivity with the two bound troponin I capture antibodies (not shown for clarity because these lines were very close to the line with the negative control).

FIG. 12B shows a calibration curve (GMR signal in ppm vs. D-dimer concentration) for D-dimer by running samples with varied, fixed concentrations of D-dimer. The calibration curve allows concentrations to be computed for a future unknown sample containing the D-dimer as the query analyte. A similar plot in FIG. 12C is provided for the cardiac biomarker troponin I. Together, these results establish the viability of detecting D-dimer and troponin I in, blood or plasma samples of a subject.

Figure 13:
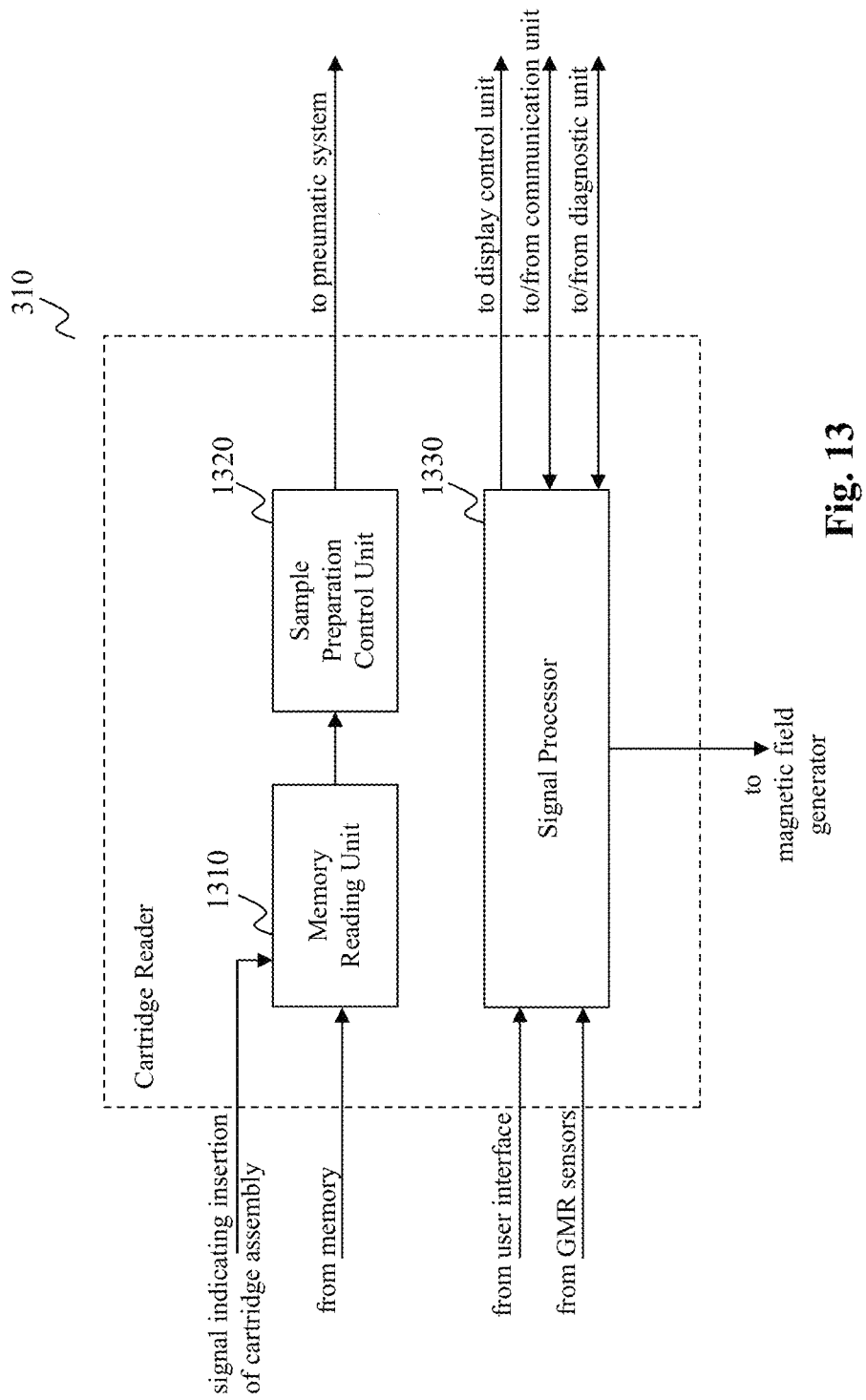
FIG. 13 schematically shows functional blocks of the cartridge reader in accordance with an embodiment of the present disclosure.

FIG. 13 schematically shows functional blocks of the cartridge reader 310 in accordance with an embodiment of the present disclosure. As shown in FIG. 13, the cartridge reader 310 can be divided roughly into a sample preparation control part and a signal processing part. A memory reading unit 1310 and a sample preparation control unit 1320 form the sample preparation control part. The memory reading unit 1310 is adapted to, upon receipt of a signal indicating that a cartridge assembly 200 has been inserted into the cartridge reader 310, read information stored in the memory chip 275 on the cartridge assembly 200. The sample preparation control unit 1320 is configured to, based on the information read from the memory chip 275, generate pneumatic control signals and send them to the pneumatic system 330. In some embodiments, when insertion of the cartridge assembly 200 into the cartridge reader 310 is recognized, an indication signal may be created by the cartridge assembly 200 and sent to the memory reading unit 1310 to inform of the insertion event. Alternatively, in other embodiments, such an indication signal may be created by other components at the cartridge reader 310 and sent to the memory reading unit 1310.

The signal processing function of the cartridge reader 310 is mainly performed by a signal processor 1330. The signal processor 1330 is adapted to control electrical elements, prepare and collect signals, and process, display, store, and/or relay detection results to external systems. For example, the signal processor 1330 operates to generate a control signal for controlling the magnetic field generator 360, resulting in magnetic field excitation applied onto the GMR sensors in the cartridge assembly 200. After receiving measurement signals from the GMR sensors in the cartridge assembly 200 and from at least one reference resistor disposed in the cartridge assembly 200 and/or the signal processor 1330, the signal processor 1330 processes the measurements signals to obtain test results of the analyte detection. Via the display control unit 120, the test results are displayed on an integrated or external display. Moreover, the signal processor 1330 is coupled to the user interface 140 for receiving instructions from the user. Additionally, in some embodiments, the signal processor 1330 is coupled to the communication unit 340 and/or with the diagnostic unit 350, enabling evaluation and diagnosis from the test results alone or in combination with other externally available data.

Figure 14:
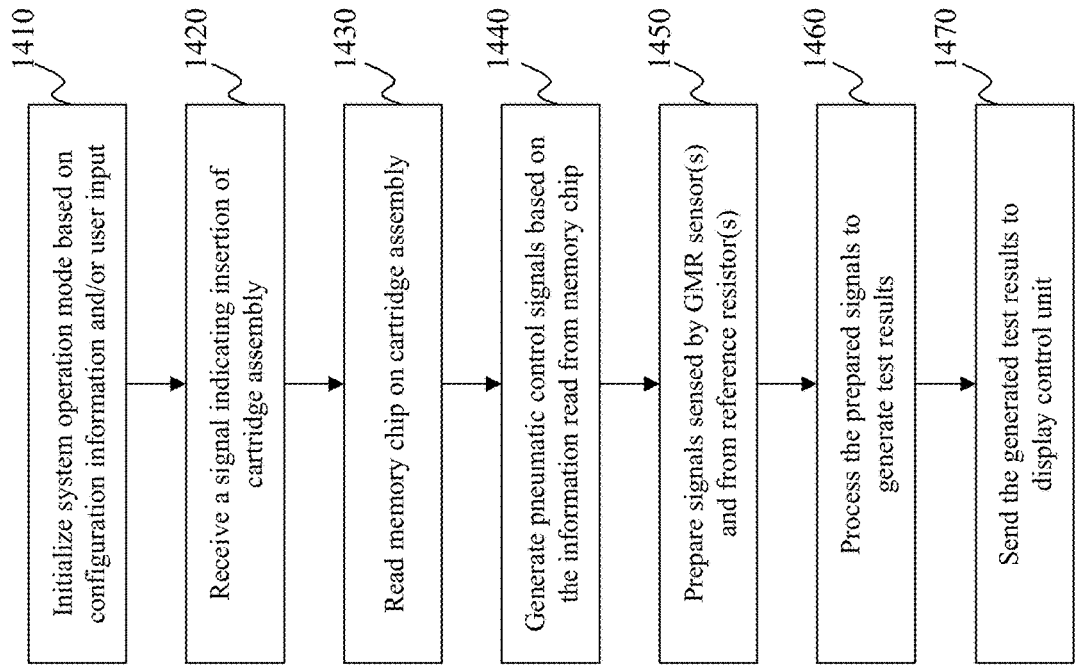
FIG. 14 is a flowchart of the process of the cartridge reader in accordance with an embodiment of the present disclosure.

FIG. 14 is a flowchart of the process of the cartridge reader 310 in accordance with an embodiment of the present disclosure. As shown in FIG. 14, the cartridge reader 310 starts its operation at step 1410 by initializing the operation mode based on system configuration profile and/or instructions inputted by the user via the user interface 140. Then, the process waits at step 1420 for a signal indicating that a cartridge assembly 200 has been inserted into the cartridge reader 310. This signal can be created by either the cartridge assembly 200 or the cartridge reader 310 upon recognition of the insertion. In response to receiving such a signal, at step 1430, the cartridge reader 310 reads the memory chip 275 on the cartridge assembly 200. Then, at step 1440, the cartridge reader 310 generates control signals based on the read information, and sending them to the pneumatic system 330 for pneumatic control used in preparation of the sample to be tested. At step 1450, the cartridge reader 310 prepares measurement signals at the GMR sensors and at the at least one reference resistor and receives the signals. Then, at step 1460, the cartridge reader 310 processes the received measurement signals to generate test results. Finally, at step 1470, the cartridge reader 310 sends the generated test results to the display control unit 120 for display to the user.

Figure 15:
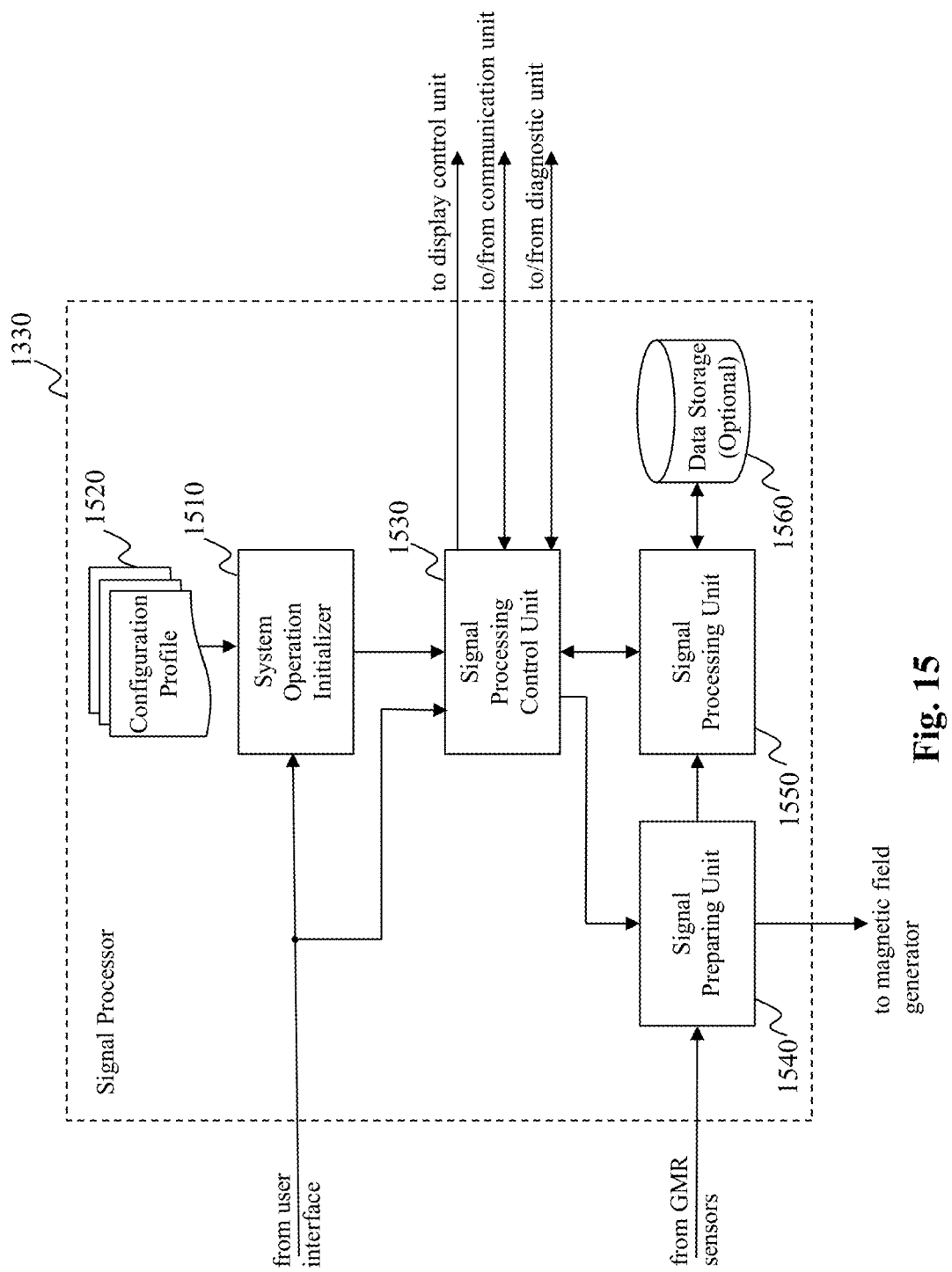
FIG. 15 schematically shows the functional blocks of the signal processor in accordance with an embodiment of the present disclosure.

FIG. 15 schematically shows the functional blocks of the signal processor 1330 in accordance with an embodiment of the present disclosure. As shown in FIG. 15, the signal processor 1330 includes a system operation initializer 1510, a configuration profile 1520, a signal processing control unit 1530, a signal preparing unit 1540, a signal processing unit 1550 and an optional data storage 1560. The system operation initializer 1510 is configured to, based on system configuration information read from the configuration profile 1520 and/or instructions received via the user interface 140, set up a system operation environment and initialize the functions of the signal processor 1330, in particular those of the signal processing control unit 1530. The signal processing control unit 1530 operates to generate control signals for controlling the signal preparing unit 1540 and the signal processing unit 1550. It also operates to control display of the detection results via the display control unit 120 on a display, and to control communication of data between the signal processing control unit 1550 and the communication unit 340 and/or the diagnostic unit 350. The signal preparing unit 1540 is configured to, under the control of the signal processing control unit 1530, prepare measurement circuits, excite an AC magnetic field applied to the GMR sensors and create carrier signal applied to the measurement circuits, collect measurement signals from the measurement circuits, and feed the measurement signals after amplification and analog-to-digital-conversion to the signal processing unit 1550. The signal processing unit 1550 is configured to process the received measurement signals by analytically solving for detection results, and send the detection results to the signal processing control unit 1530. Additionally, in some embodiments, the result data may be stored in the optional data storage 1560.

Figure 16:
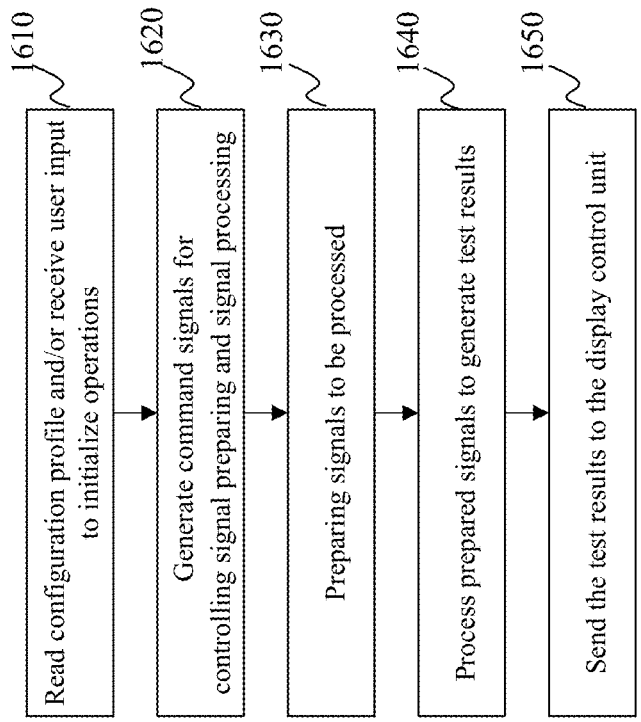
FIG. 16 is a flowchart of the process for the signal processor in accordance with an embodiment of the present disclosure.

FIG. 16 is a flowchart of the process for the signal processor 1330 in accordance with an embodiment of the present disclosure. As shown in FIG. 16, the process starts at step 1610 by reading system configuration information from the configuration profile and/or receiving user instructions via the user interface 140 to initialize the system operation environment. Then, at step 1620, a series of control signals are generated by the signal processing control unit 1530 for administrating the operations of the signal preparing unit 1540 and the signal processing unit 1550. At step 1630, measurement circuits are built up by the signal preparing unit 1540 based on the control signals from the signal processing control unit 1530, so as to prepare measurement signals from the GMR sensors and the at least one reference resistor. Then, at step 1640, the prepared measurement signals are processed by the signal processing unit 1550 to solve for test results of the analyte detection. Finally, at step 1650, the generated test results are sent from the signal processing unit 1550 to the display control unit 120 for display to the user.

Figure 17:
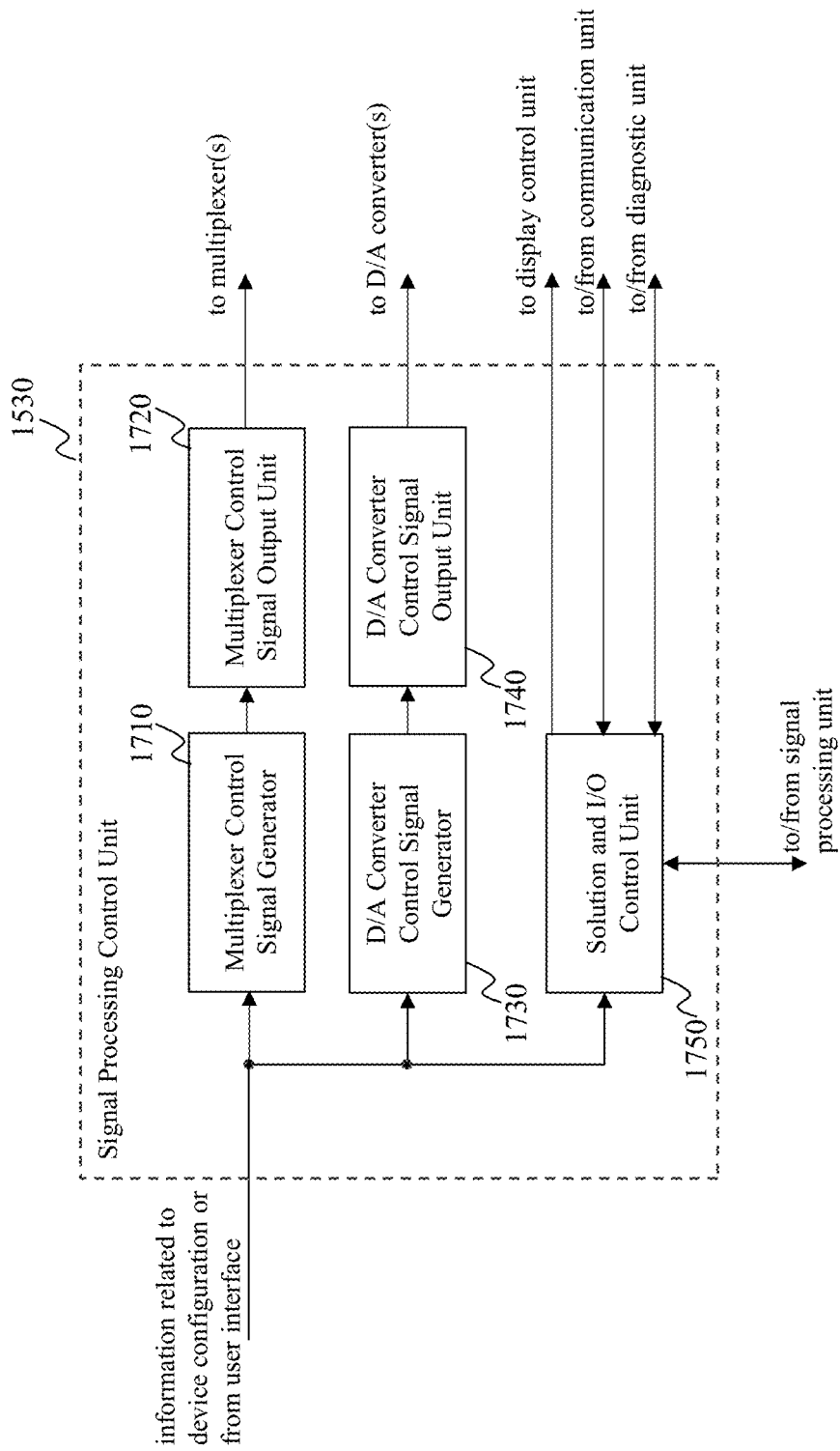
FIG. 17 schematically shows the functional blocks of the signal processing control unit in accordance with an embodiment of the present disclosure.

FIG. 17 schematically shows the functional blocks of the signal processing control unit 1530 in accordance with an embodiment of the present disclosure. As shown in FIG. 17, the signal processing control unit 1530 includes a multiplexer control signal generator 1710, a multiplexer control signal output unit 1720, a D/A converter control signal generator 1730, a D/A converter control signal output unit 1740, and a solution and I/O control unit 1750. Based on information related to system configuration and/or inputted via the user interface 140, the multiplexer control signal generator 1710 generates control signals for one or more multiplexers in the signal preparing unit 1540, and sends them to the multiplexers through the multiplexer control signal output unit 1720. The D/A converter control signal generator 1730 and the D/A converter control signal output unit 1740 are responsible for the generation and sending of the control signal to one or more D/A converters in the signal preparing unit 1540. The solution and I/O control unit 1750 administrates the processing of the measurement signals by the signal processing unit 1550, receives the processing results, and sends them to the display control unit 120. Optionally, the solution and I/O control unit 1750 also serves as an interface with the communication unit 340 and with the diagnostic unit 350.

Figure 18:
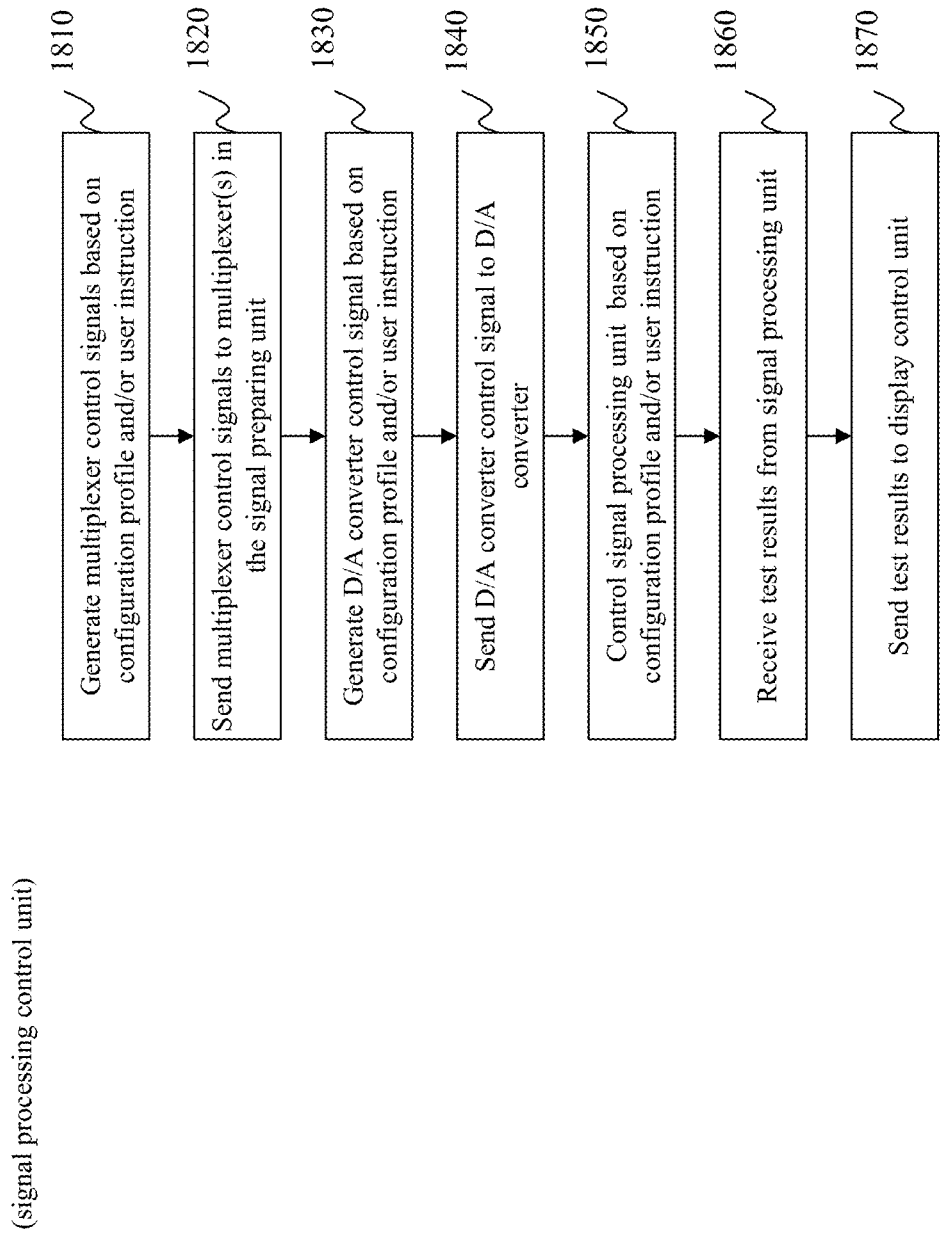
FIG. 18 is a flowchart of the process for the signal processing control unit in accordance with an embodiment of the present disclosure.

FIG. 18 is a flowchart of the process for the signal processing control unit 1530 in accordance with an embodiment of the present disclosure. The process starts at step 1810 by generating multiplexer control signals in the multiplexer control signal generator 1710 based on information read from configuration profile and/or user instructions received from the user interface 140. At step 1820, the generated control signals are sent to the at least one multiplexer in the signal preparing unit 1540 to configure the structure of measurement circuits. At step 1830, D/A converter control signal is generated by the D/A converter control signal generator 1730 based on configuration information and or user instructions, and is sent at step 1840 to the at least one D/A converter in the signal preparing unit 1540. Then, at step 1850, based on the configuration information and/or user instruction, the solution and I/O control unit 1750 controls the signal processing of the measurement signals by the signal processing unit 1550. After the signal processing is completed, at step 1860, the solution and I/O control unit 1750 receives test results from the signal processing unit 1550. Then, at step 1870, the solution and I/O control unit 1750 sends the received test results to the display control unit 120 for display on an integrated or external display. The order of steps 1810-1820 and 1830-1840 may be changed; i.e., the control of the multiplexer(s) may be before or after the control of D/A converter(s); or they can be performed at the same time.

Figure 19:
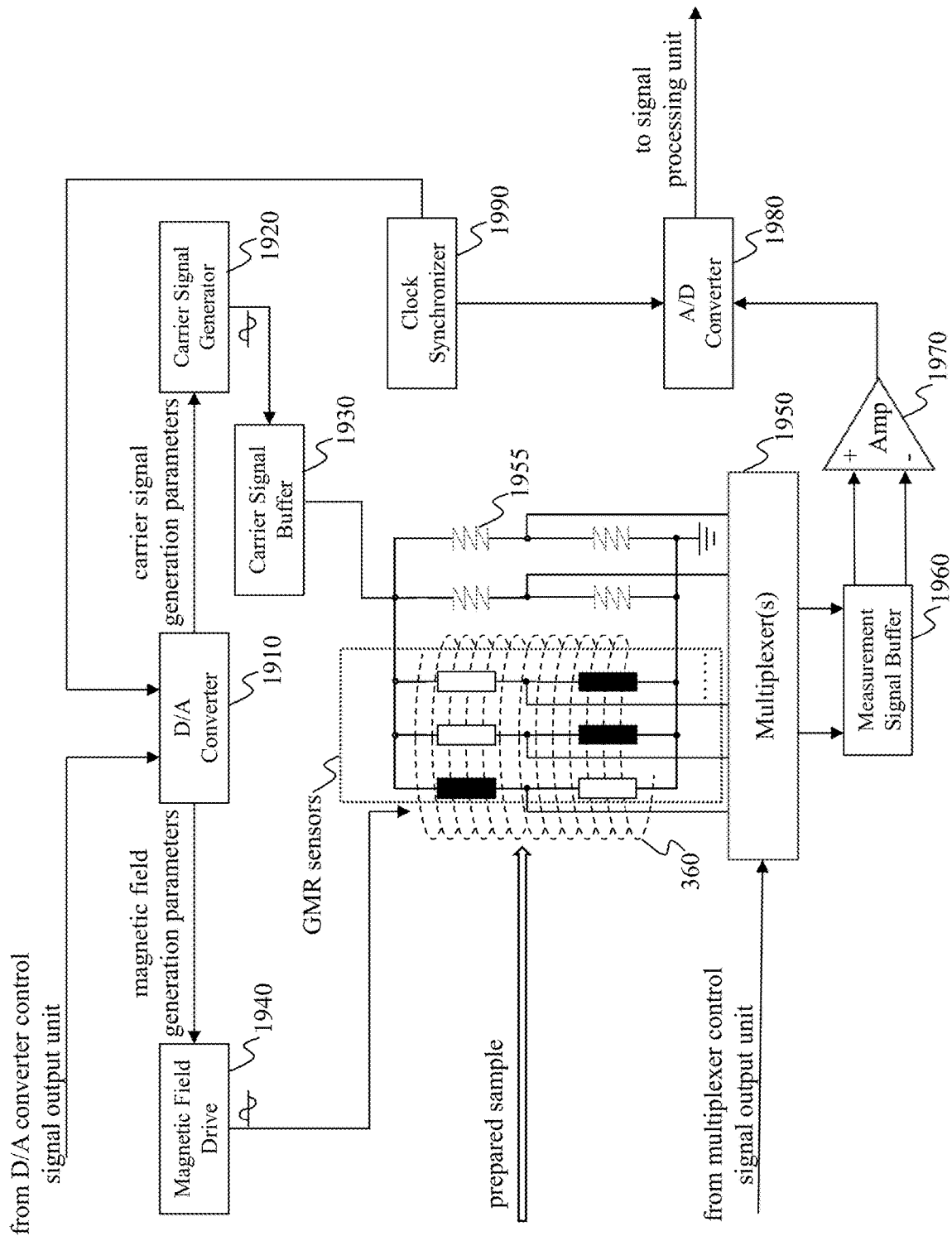
FIG. 19 schematically shows the functional blocks of the signal preparing unit in accordance with an embodiment of the present disclosure.

FIG. 19 schematically shows the functional blocks of the signal preparing unit 1540 in accordance with an embodiment of the present disclosure. As shown in FIG. 19, the signal preparing unit 1540 comprises a carrier signal generation part, a magnetic field excitation part, a circuit configuration part, a signal pick up part, and a clock synchronization part. For ease of illustration, FIG. 19 also shows the magnetic field generator 360 and the GMR sensors in the cartridge assembly 200, though they are not components of the signal preparing unit 1540.

A D/A converter 1910, a carrier signal generator 1920 and a carrier signal buffer 1930 form the carrier signal generation part. The D/A converter 1910 is configured to receive control signal from the D/A converter control signal output unit 1740 of the signal processing control unit 1530, and generate carrier signal generation parameters based on the received control signal. The carrier signal generator 1920 is configured to, based on the carrier signal generation parameters from the D/A converter 1910, generate AC carrier signal used in the measurement circuits. A carrier signal buffer 1930 is coupled between the carrier signal generator 1920 and the measurement circuits, making the carrier signal generator 1920 present a very low impedance output relative to the higher impedance of the measurement circuits. Optionally, filters can be disposed at the carrier signal input to the measurement circuits to remove potential harmonics.

Although an AC voltage signal is shown in FIG. 19 as the carrier signal applied to the measurement circuits, depending on the structure of the measurement circuits, the carrier signal can be an AC current signal, DC voltage signal, or DC current signal.

The D/A converter 1910 and a magnetic field drive 1940 form the magnetic field excitation part. Based on the control signal received from the D/A converter control signal output unit 1740 of the signal processing control unit 1530, the D/A converter 1910 generates magnetic field generation parameters. The magnetic field drive 1940 is configured to drive the magnetic field generator 360 based on the magnetic field generation parameters, so as to apply AC magnetic field onto the GMR sensors. Though the carrier signal generation part and the magnetic field excitation part shown in FIG. 19 share a common D/A converter, they can use separate D/A converters to generate carrier signal control parameters and magnetic field excitation control parameters.

The circuit configuration part includes at least one multiplexer 1950 and at least one reference resistors 1955. When the cartridge assembly 200 is inserted into the cartridge reader 310, via the electrical contact pads 290 provided on the cartridge assembly 200, electric connection is formed between the electric contact pads 640A, 640B of the GMR sensor chip 280 on the cartridge assembly 200 and the signal preparing unit 1540 of the cartridge reader 310. Based on the multiplexer control signal received from the signal processing control unit 1530, the at least one multiplexer 1950 routes one or more GMR sensors or one or more reference resistors in to configure appropriate measurement circuits.

In some embodiments, for the sake of cost advantages, multiplexer(s) 1950 and reference resistor(s) 1955 are disposed in the cartridge reader 310. Alternatively, in other embodiments, they can be disposed in the cartridge assembly 200 to achieve many performance advantages like reduced trace length between the multiplexer(s) and the GMR sensors, reduced number of connections from the cartridge assembly 200 to the cartridge reader 310, etc. Or, the multiplexer(s) and the reference resistor(s) can be placed on both the cartridge reader 310 and the cartridge assembly 200.

A measurement signal buffer 1960, a differential amplifier 1970 and an A/D converter form the signal pick up part (also called "differential voltage probe" or "voltage probe"). The measurement signal buffer 1960 is coupled between the multiplexer(s) 1950 and the differential amplifier 1970 and is used to make the measurement circuits present a relatively high impedance at the inputs of the differential amplifier 1970. The differential amplifier 1970 operates to capture time series of the voltage observations from the measurement circuits, and send the amplified measurement signals to the A/D converter 1980. The A/D converter 1980 is configured to send the analog-to-digital-converted measurement signals to the signal processing unit 1550. Optionally, filters can be used at the differential amplifier 1970 and/or at the A/D converter 1980 to remove harmonics.

Preferably, in some embodiments, a clock synchronizer 1990 is used to provide synchronization between the carrier signal generation part, the magnetic field excitation part and the signal pick up part. More specifically, the generation of the carrier signal generation parameters and the magnetic field generation parameters by the D/A converter 1910 is clocked from the same source as the A/D converter 1980, i.e. by the clock synchronizer 1990.

Figure 20:
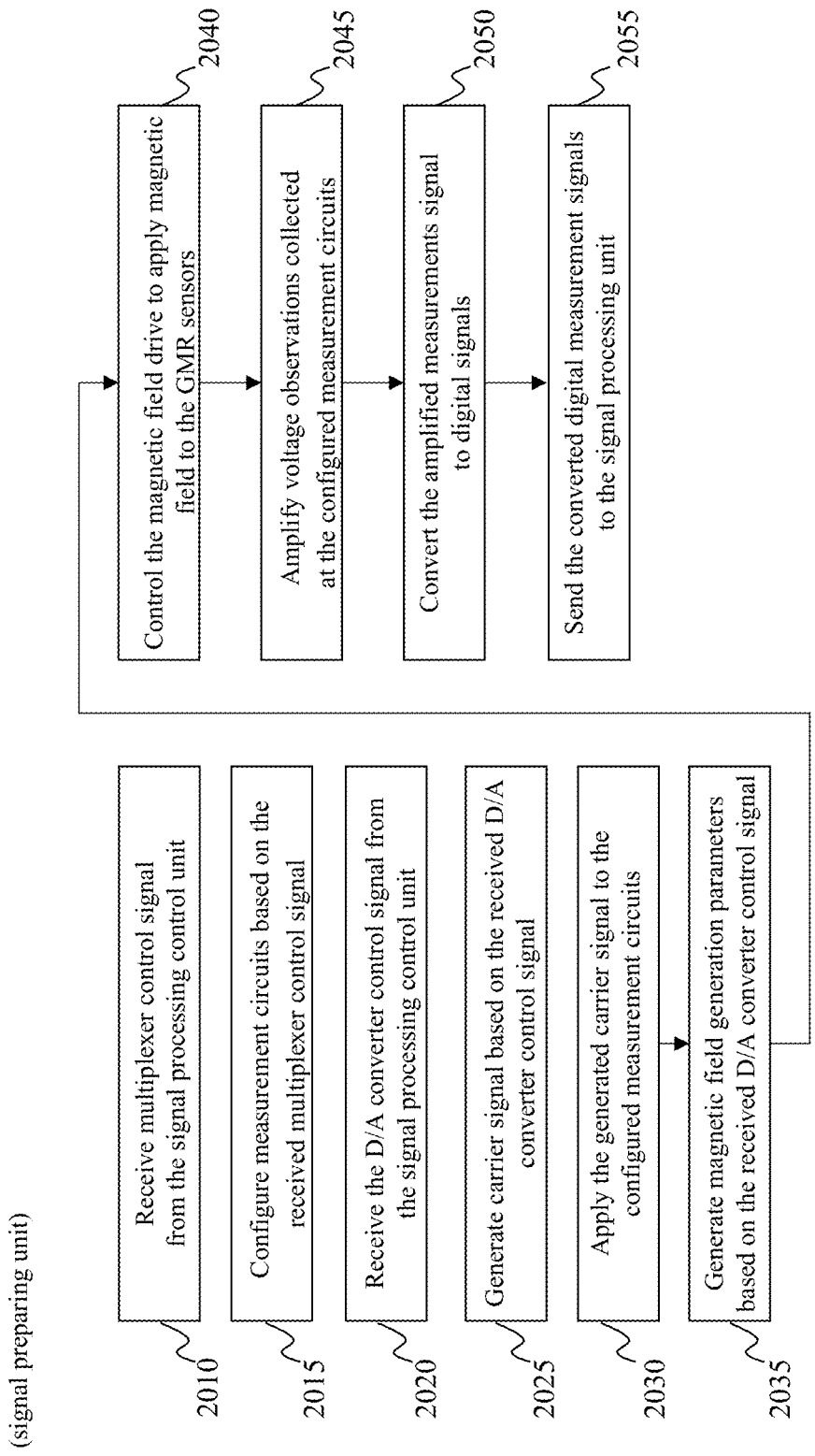
FIG. 20 is a flowchart of the process for the signal preparing unit in accordance with an embodiment of the present disclosure.

FIG. 20 is a flowchart of the process for the signal preparing unit 1540 in accordance with an embodiment of the present disclosure. As shown in FIG. 20, the process start at step 2010 by receiving multiplexer control signal from the signal processing control unit 1530. Then, at step 2015, the multiplexer 1950 in the signal preparing unit 1540 configures the measurement circuits based on the received multiplexer control signal by routing certain GMR sensors and/or reference resistor(s) in. At step 2220, the signal preparing unit 1540 receives the D/A converter control signal from the signal processing control unit 1530. Based on the D/A converter control signal, at step 2025, the D/A converter 1910 in the signal preparing unit 1540 generates carrier signal generation parameters. Then, at step 2230, the carrier signal is generated based on the generated carrier signal generation parameters, buffered and applied to the measurement circuits configured at step 2015. At step 2035, the D/A converter 1910 in the signal preparing unit 1540 generates magnetic field generation parameters based on the D/A converter control signal. Then, at step 2040, magnetic field is excited by the magnetic field generator drive 1940 based on the magnetic field generation parameters, and applied to the GMR sensors via the magnetic field generator 360. At step 2045, the measurement signals collected at the configured measurement circuits are buffered, and then amplified by the differential amplifier 1970 in the signal preparing unit 1540. At step 2050, the amplified measurement signals are converted into digital signals by the A/D converter 1980 in the signal preparing unit 1540. Finally, at step 2055, the converted digital signals are sent to the signal processing unit 1730 for further processing. The order of steps 2025-2030 and 2035-2040 may be changed; i.e., generation of the magnetic field excitation may be before or after generation of the carrier signal; or they can be performed at the same time.

Figure 21:
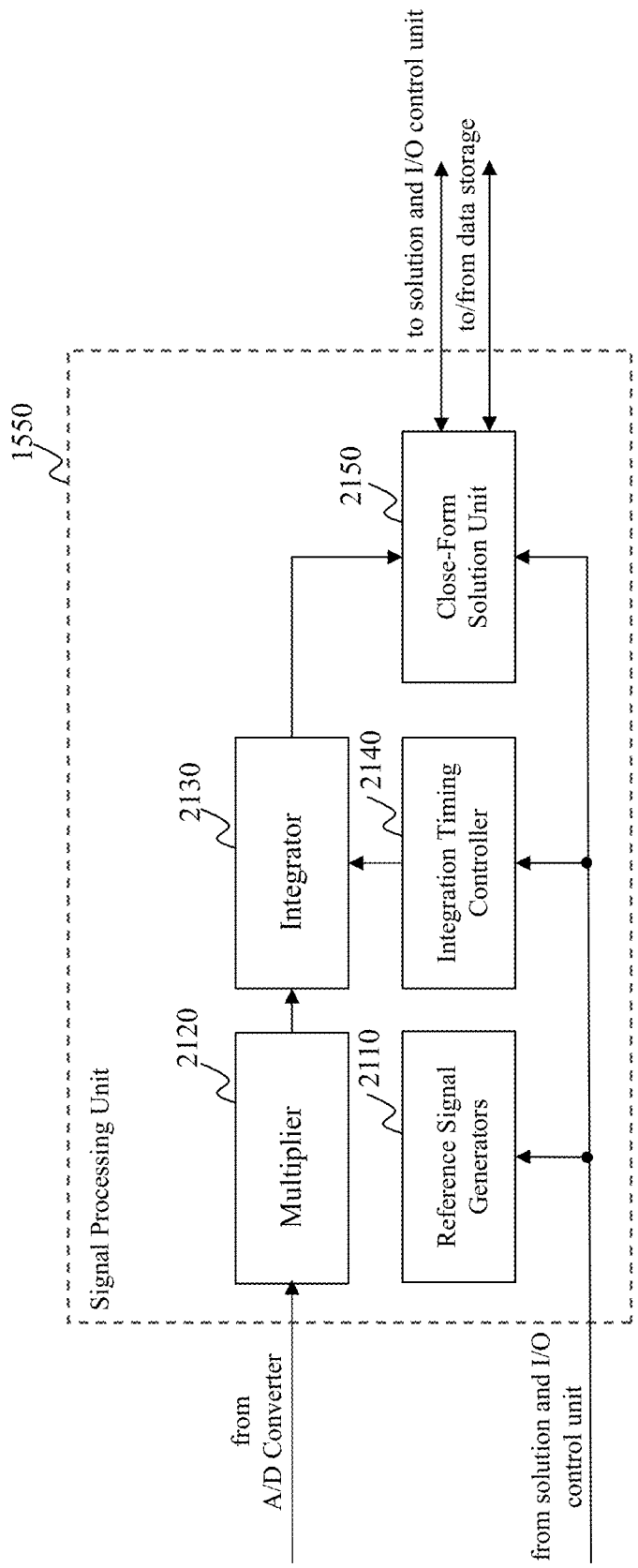
FIG. 21 schematically shows the functional blocks of the signal processing unit in accordance with an embodiment of the present disclosure.

FIG. 21 schematically shows the functional blocks of the signal processing unit 1550 in accordance with an embodiment of the present disclosure. As shown in FIG. 21, the signal processing unit 1550 comprises reference signal generators 2110, a multiplier 2120, an integrator 2130, an integration timing controller 2140, and a close-form solution unit 2150.

The reference signal generators 2110 are configured to receive control signal from the solution and I/O control unit 1750 of the signal processing control unit 1530, generate in-phase and quadrature (rotated 90 degrees) sinusoid reference signals at all frequencies of interest based on the received control signal, and send the generated reference signals to the multiplier 2120. The multiplier 2120 is configured to receive the measurement signals from the A/D converter 1980 of the signal preparing unit 1540, and multiply the measurement signals by the reference signals from the reference signal generators 2110 to produce an in-phase product and a quadrature product at each frequency of interest for each measurement signal. The in-phase products and quadrature products are sent to the integrator 2130. The integrator 2130 is configured to accumulate these products under the control of the integration timing controller 2140 and send the accumulations to the close-form solution unit 2150. The close-form solution unit 2150 is adapted to solve for, from the received accumulations, the phase-accurate GMR sensor resistance and magnetoresistance quantities that are not influenced by the frequency, amplitude or phase of the applied carrier signal, or by the amplitude or phase response of the circuits supplying this.

Figure 22:
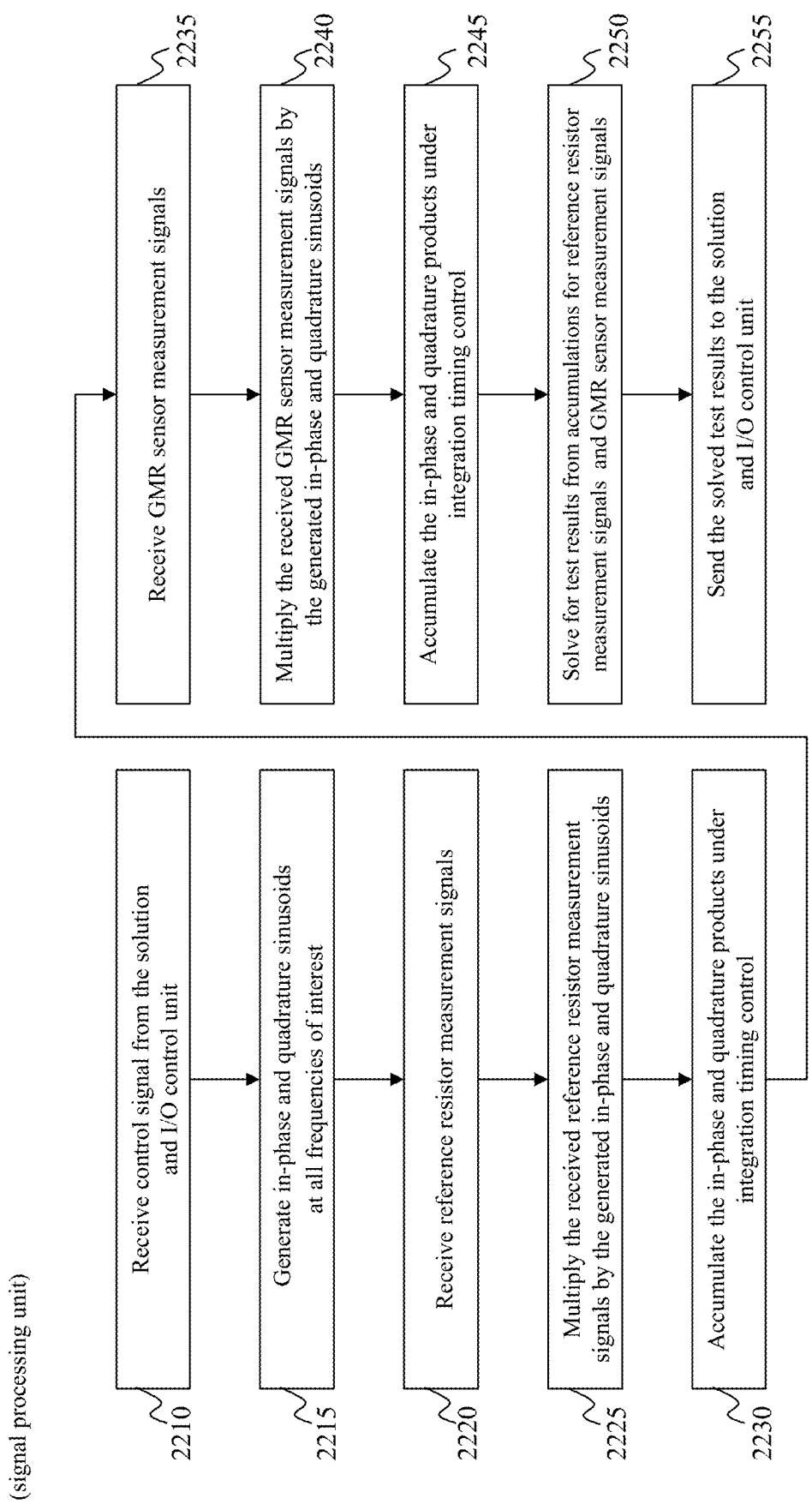
FIG. 22 is a flowchart of the process for the signal processing unit in accordance with an embodiment of the present disclosure.

FIG. 22 is a flowchart of the process for the signal processing unit 1550 in accordance with an embodiment of the present disclosure. As shown in FIG. 22, the process starts at step 2210 by receiving control signal from the solution and I/O control unit 1750 of the signal processing control unit 1530. At step 2215, in-phase and quadrature sinusoid reference signals at all frequencies of interest are generated in the signal processing unit 1550 based on the control signal. Then, at step 2220, the reference resistor measurement signals are received from the signal preparing unit 1540. At step 2225, the reference resistor measurement signals are multiplied by the in-phase and quadrature sinusoid reference signals generated at step 2215 to generate in-phase and quadrature products at all frequencies of interest. At step 2230, the in-phase and quadrature products obtained at step 2225 are accumulated under integration timing control. At steps 2235-2250, similar processing is performed for the received measurement signals for the GMR sensors. At step 2250, test results are solved for in a close-form way from the in-phase and quadrature products of both reference resistor measurement signals and GMR sensor measurement signals. Finally, at step 2255, the solved test results are sent to the solution and I/O control unit 1750 of the signal processing control unit 1530.

The order of steps 2220-2230 and 2235-2245 may be changed; i.e., accumulation for reference resistor measurement signals may be before or after accumulation for GMR sensor measurement signals.

As described above referring to FIG. 8B, electrical resistance of a GMR sensor changes under the influence of a magnetic field. A GMR sensor can be monitored in real time while superparamagnetic nanoparticles bind through the assay to the GMR sensor. A local change in magnetic field is translated to a change in sensor resistance and observed as a change in voltage in a properly configured measurement circuit.

However, by use of traditional differential measurement circuits, for examples, a Wheatstone bridge circuit or an Anderson loop circuit, it is impossible to directly discern increasing magnetoresistance from decreasing magnetoresistance based on voltage at the voltage probe. An example of voltage measurements obtained with one available measurement circuit topology is plotted in FIG. 23. As can be seen in the plot, in the lack of phase sensitivity, it's hard to derive the correct relationship between sensor impedance (Zs) and reference impedance (Zr). All one can tell from increasing voltage is that elements in the measurement circuit are changing with respect to each other. As a result, when using these traditional circuits with AC measurement, less optimal ways have to be taken to deal with this problem.

A common suboptimal option is to bias the measurement circuit away from balance such that the voltage signal at the voltage probe never crosses zero. This approach has negative impacts on signal-to-noise ratio of the measurement circuit. Further, even with a bias, increasing or decreasing magnetoresistance still must be deduced via inference or other indirect knowledge.

Figure 23:
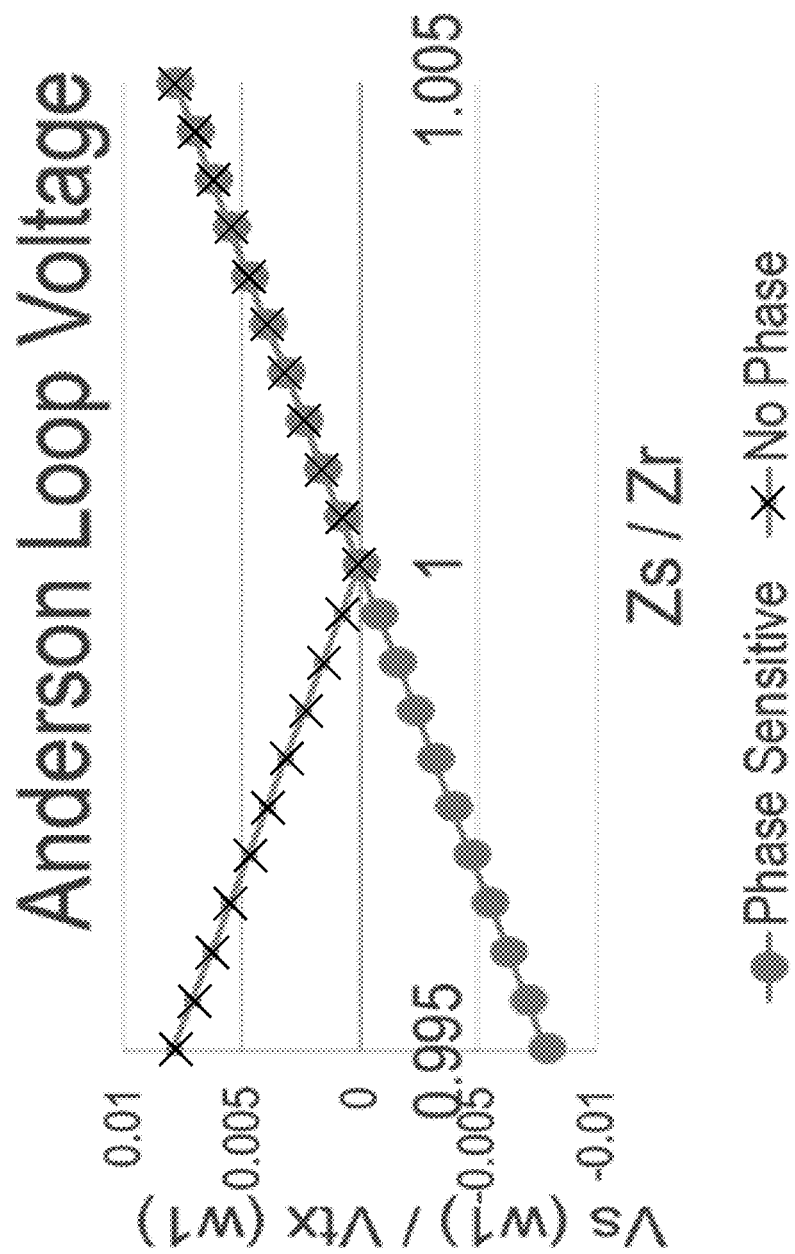
FIG. 23 shows an example of voltage measurements obtained with one available measurement circuit topology.

Otherwise, if a balanced measurement circuit is adopted to achieve a good signal-to-noise ratio level, large artifacts appear in telemetry: magnetoresistance appears to decrease to zero and then increase (a V shape as shown in FIG. 23 which always seems to be positive), while actually it may only be decreasing or be increasing.

The present disclosure introduces phase sensitivity into the context of GMR-based detection to derive correct measurements. The signal processing technique disclosed here has an ability to measure across a perfectly balanced GMR measurement circuit (for example, a balanced Wheatstone bridge) without the issues encountered by the prior art. Moreover, the technique is sufficiently general to apply to any of the available circuit topologies to achieve phase-sensitive measurements and calculation of magneto resistance in GMR sensors. The generality of the approach disclosed here provides an additional competitive advantage because it enables a direct comparison of different circuit topologies while continuing to deliver the same output signal to the end user.

Figure 24A:
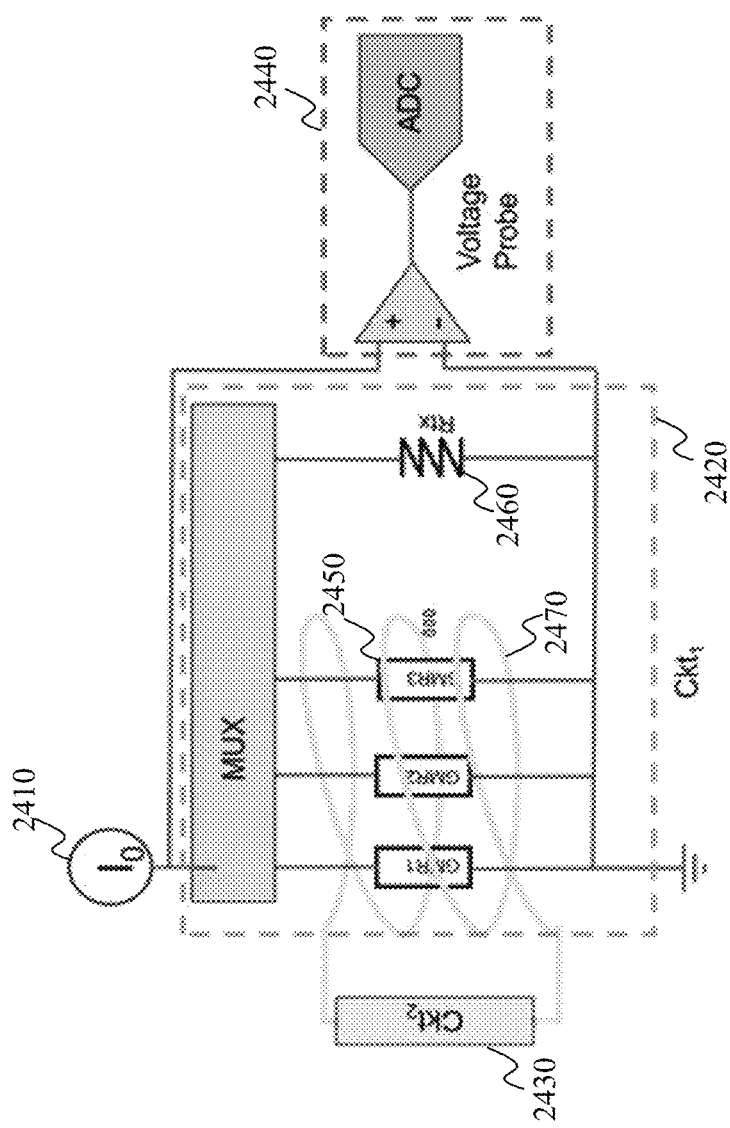
FIGS. 24A-C show several available circuit topologies for embodying the present signal processing technique.
Figure 24B:
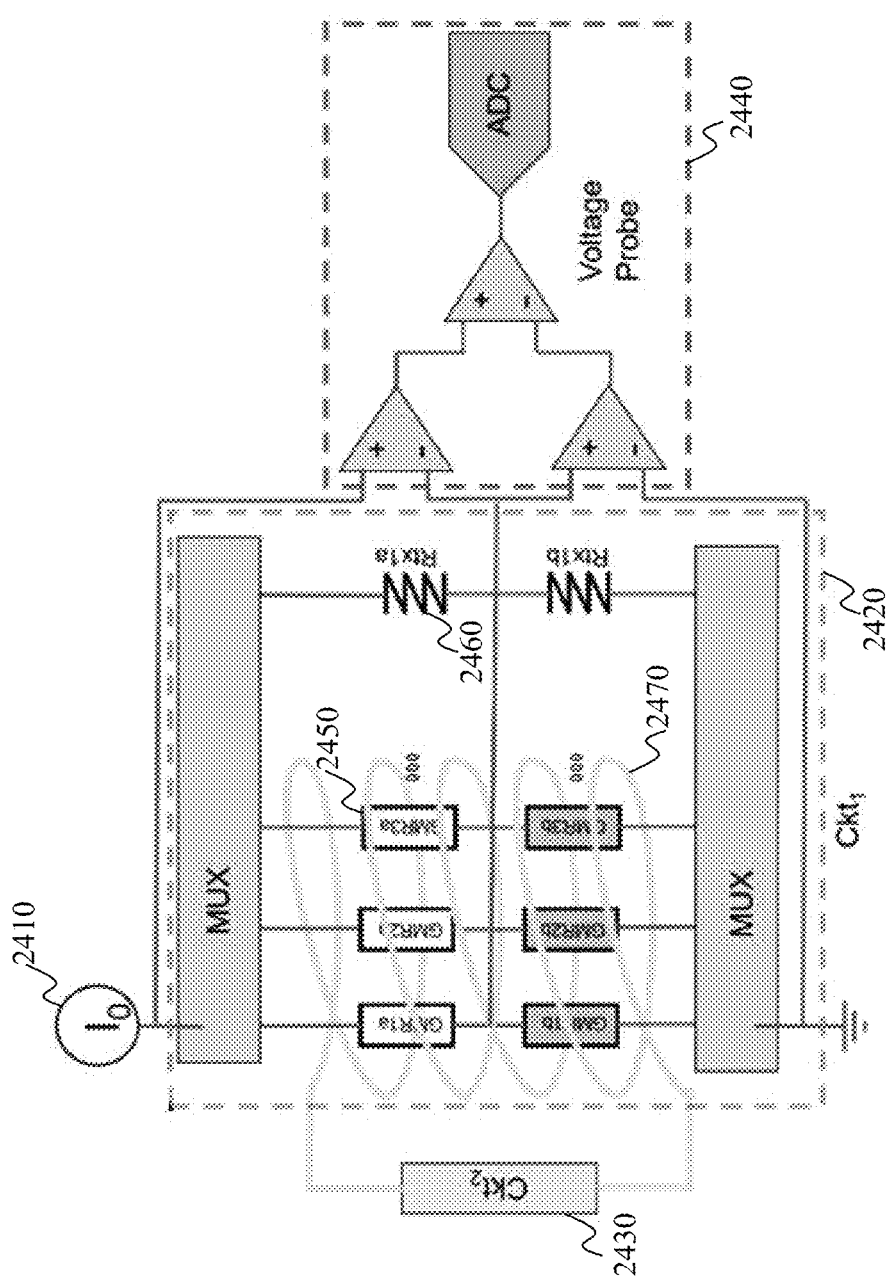
Figure 24C:
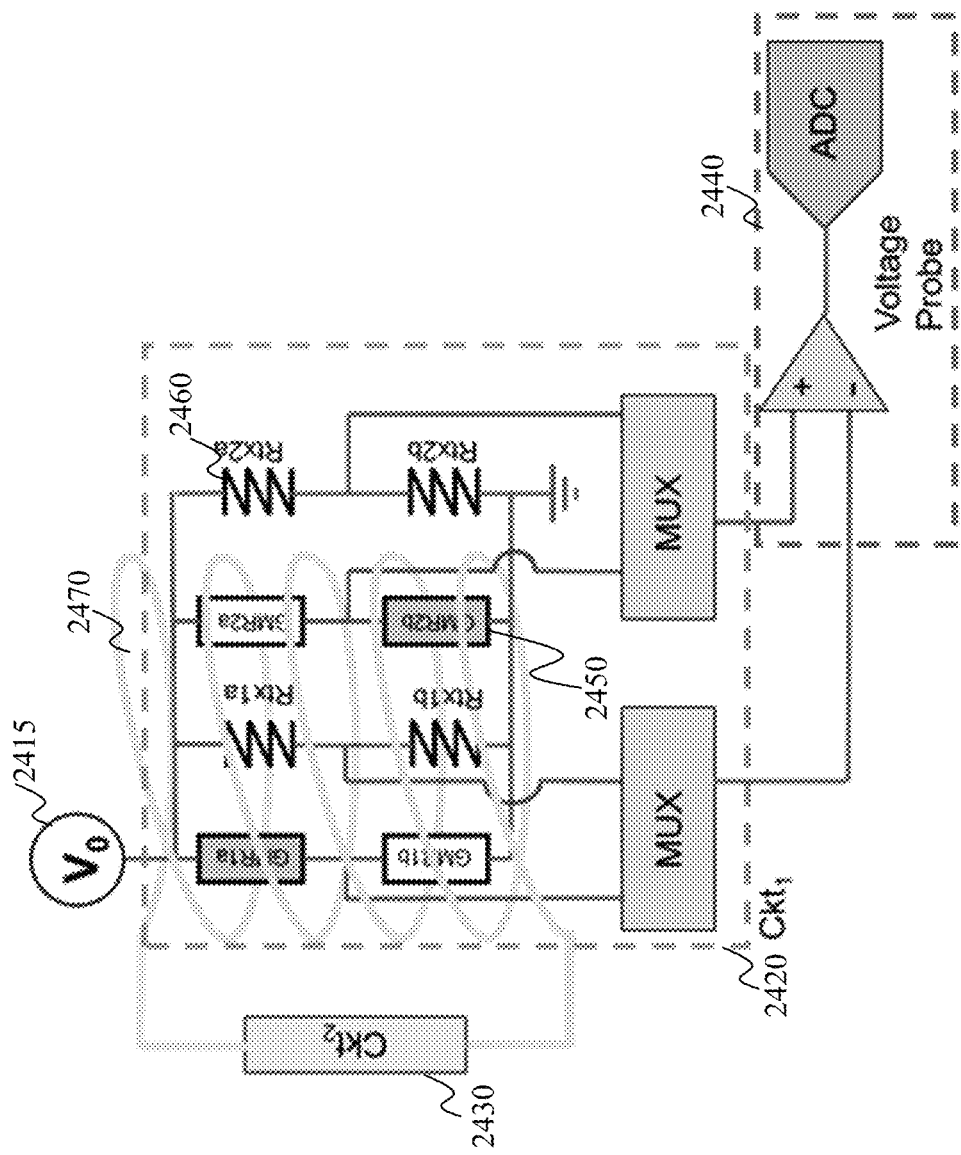

FIG. 24A shows a simple circuit topology for embodying this technique. FIGS. 24B-C show several other available circuit topologies. For example, a circuit topology based on the Anderson loop and an AC current source is exemplarily illustrated in FIG. 24B, while a circuit topology based on the Wheatstone bridge and an AC voltage source is shown in FIG. 24C. The circuit topologies include a carrier source 2410 or 2415, a first control circuit Ckt1 2420, a second control circuit Ckt2 2430, a voltage probe 2440, at least one GMR sensor 2450, at least one high-precision reference resistor 2460, and a magnetic field generator 2470.

As shown in FIG. 24A, the carrier source 2410 is configured to provide a buffered current source for applying an AC carrier signal at frequency $\omega_1$ (for different measurement circuit configurations, a carrier source 2415 may operate to provide a buffered voltage source). In FIG. 24A, the first control circuit Ckt1 2420 allows switching between the GMR sensor 2450 and the similarly arranged high-precision reference resistor 2460 with known characteristics in order to apply the AC carrier signal from the carrier source 2410 to the GMR sensor 2450 or to the high-precision reference resistor 2460. By constructing a sensing path and replicating a reference path in Ckt1, the present technique achieves balanced parasitic elements. In these structures, parasitic elements appear in equivalent locations. Thus, the differential voltage at the voltage probe primarily arises from the differences in the GMR sensor and reference resistor being measured due to common mode rejection in the differential voltage probe. In other embodiments, additionally or alternatively, the parasitic elements are explicitly modeled for decomposition from measurement signals so as to cancel the effects of the parasitic elements.

The second control circuit Ckt2 2430 and the magnetic field generator 2470 are used to apply a sinusoidal magnetic field at frequency $\omega_2$ to the GMR sensor 2450. The applied magnetic field will modulate the GMR sensor's resistance, but will not affect the high-precision reference resistor 2460.

The differential voltage probe 2440 is connected to detect the impedance of the GMR sensor 2450 or of the high-precision reference resistor 2460. The voltage probe 2440 is designed as having sufficiently high impedance, and thus measurements of the GMR sensor and the reference resistor are not perturbed.

As the applied sinusoidal magnetic field modulates the GMR sensor's resistance, application of this sinusoidal magnetic field at frequency $\omega_2$ while also applying the carrier signal at frequency $\omega_1$ will modulate the amplitude of the voltages associated with the GMR sensor 2450, giving rise to sideband voltages. The first set of sideband voltages occur at frequencies $\omega_1-\omega_2$ and $\omega_1+\omega_2$.

However, these sideband voltages will not be induced across the high-precision reference resistor 2460 by application of the sinusoidal magnetic field. Thus, it is necessary to manually induce these sideband voltages across the reference resistor 2460 when the high-precision reference resistor 2460 is switched into the measurement circuit for observation. It can be carried out by mixing the sideband signals into the carrier with amplitudes equal to the amplitude of the carrier. In other words, the sideband signals can be induced by addition to the carrier signal upstream of the buffer for the buffered voltage or current source. More especially, the sideband signals may be added to the carrier signal with equal amplitude to the carrier.

The measurement process for the topology shown in FIG. 24A is as follows. Via the first control circuit Ckt1 2420, the GMR sensor 2450 is switched into the measurement circuit while both the carrier signal and the sinusoidal magnetic field are applied. Using the voltage probe 2440, a time series of voltages are captured for a duration $t_1$ which is chosen based upon noise requirements.

Similarly, the high-precision reference resistor 2460 is switched into the measurement circuit. This time, the carrier signal at frequency $\varphi_1$ and mixed signals at frequencies $\omega_1-\omega_2$ and $\omega_1+\omega_2$ with amplitudes equal to the carrier are applied. Using the voltage probe 2440, again, a time series of voltages are captured for a duration $t_2$ which is also chosen based upon noise requirements.

Then, each sample of the respective time series is multiplied by samples from in-phase sine wave time series at frequencies $\omega_1$, $\omega_1-\omega_2$ and $\omega_1+\omega_2$ and quadrature sine waves at frequencies $\omega_1$, $\omega_1-\omega_2$ and $\omega_1+\omega_2$ offset 90 degrees, respectively. By accumulating at an integrator the in-phase and quadrature products at each frequency for the GMR sensor 2450 and the high-precision reference resistor 2460, six complex quantities are generated which are proportional to the probed voltages at frequencies $\omega_1$, $\omega_1-\omega_2$ and $\omega_1+\omega_2$ during observation of the GMR sensor 2450 and the high-precision reference resistor 2460.

Then, the GMR sensor accumulations are divided by $t_1$, and the reference resistor accumulations by $t_2$. By designating the in-phase accumulations as real components and the quadrature accumulations as imaginary components, complex voltage-proportional terms vs associated with the GMR sensor 2450 are constructed, obtaining $v_s(\omega_1)$, $v_s(\omega_1-\omega_2)$, and $v_s(\omega_1+\omega_2)$. Similarly, complex voltage-proportional terms $v_{fx}$ associated with the high-precision reference resistor 2460 are obtained, i.e., $v_{fx}(\omega_1)$, $v_{fx}(\omega_1-\omega_2)$, and $v_{fx}(\omega_1+\omega_2)$. Then, from the six complex terms $v_s(\omega_1)$, $v_s(\omega_1-\omega_2)$, $v_s(\omega_1+\omega_2)$, $v_{fx}(\omega_1)$, $v_{fx}(\omega_1-\omega_2)$, and $v_{fx}(\omega_1+\omega_2)$, analytically solve for zero-field resistance (R0) of GMR sensor, and solve for dR from the Taylor Series expansion at the side tones. From dR/R0, obtain magneto resistance ratio MR, which is GMR sensor's change in resistance with a sinusoidal magnetic field applied divided by the sensor's resistance with zero magnetic field applied.

In the above, both duration $t_1$ and duration $t_2$ are chosen to meet noise requirements. Noise introduced by the time-variance of the system that results from a finite $t_1$ can be minimized by choosing a $t_1$ such that the proportion of accumulation time that is not modulo $2\pi$ radians for the signals at $\omega_1$, $\omega_1$, $\omega_1-\omega_2$ and $\omega_1+\omega_2$ is small compared to the total accumulation time. Random noise can be reduced by increasing $t_1$. In a similar way to $t_1$, duration $t_2$ is chosen.

With the disclosed technique, there is no need to bias away from balance, allowing for optimal gain staging and improved signal-to-noise ratio level. Resistive and reactive components can be decomposed, and parasitic elements can be measured and removed. Moreover, some difficult-to-deal-with artifacts can be cancelled, such as converter group delays which otherwise appear as large phase offsets without special handling. Further, cancellation of transfer functions upstream and downstream of the GMR sensor which is under test provides an obvious research and development advantage because of high hardware independence on tolerance of components. As the measurement will not be perturbed by elements outside of Ckt1 and Ckt2, there are three distinct benefits: (1) Designers are afforded great freedom to modify circuit elements external to Ckt1 and Ckt2 without changing output telemetry; (2) A high precision measurement can be obtained even without tight tolerances for elements external to Ckt1 and Ckt2; (3) High precision measurement requires no explicit modeling for elements outside of Ckt1.

One skilled in the art will understand that FIGS. 24A-C are only a few limited examples of the applicable circuit topologies. The GMR-based analyte detection system can be built around any of these and other available circuit topologies. Output of R0, dR and MR telemetry may be directly compared in any of these circuits. The performance of these circuits can be evaluated in terms of system specifications. These evaluations during system development will likely lead to changes to the circuit topology. By outputting signals in terms of magnetoresistance instead of voltage, circuit topologies can be changed without disruption of workflow of the end user.

An exemplary GMR-based analyte detection system is given hereafter to illustrate in detail the performance and structure of such systems. This exemplary system describes a phase-sensitive AC measurement of an amplitude-modulated magnetoresistance signal in a reconfigurable on-chip Wheatstone Bridge topology shown in FIG. 24C. The Wheatstone Bridge shown in FIG. 24C includes GMR sensor pairs in the GMR sensor chip 280 and reference resistor pairs RTX1a-RTX2b disposed on the cartridge assembly 200 or the cartridge reader 310 or both. The GMR sensors marked in black color GMR1a, GMR2b are functionalized for the assay and the GMR sensors marked in white color GMR1b, GMR2a are blocked.

As mentioned above, a GMR sensor itself is an electrically resistive element with resistance that depends on the size and direction of total magnetic field. The total magnetic field includes the field applied from a magnetic field generator (which can be either external or integrated with the GMR sensor chip) along with any disturbance from magnetic nanoparticles near the sensor.

Thus, the basic principle of the system is to monitor the resistance and magnetoresistance of GMR sensing elements before, during, and after application of functionalized magnetic nanoparticles. Components of the assay may either cause an increase or decrease in the number of magnetic nanoparticles bound to the sensor surface. This increase or decrease can be observed relative to reference elements. The reference elements can be reference sensors with negative control or reference resistors. This group of reference elements may serve as a baseline to observe a change in the active sensors.

The exemplary system uses electrical subtraction to observe the change in resistance and magnetoresistance of active GMR sensors as compared to reference sensors with negative control (or reference resistors) after the application of functionalized magnetic nanoparticles by applying a sinusoidal voltage and simultaneously observing the sensor behavior as compared to the reference elements in the presence of this sinusoidal voltage or current. In this example, because the applied signal is voltage, the currents through the sensor and reference elements may be subtracted directly. The electrical subtraction in the presence of an applied sinusoidal voltage may be accomplished by placing the active GMR sensor and reference elements into voltage dividers and subtracting the voltages at the midpoints. In other examples, if the applied sinusoid is current, the electrical subtraction may be accomplished by subtracting the voltage drops across the active GMR sensor and reference elements.

Between each observation of the active-sensor-and-reference-element subtraction, the system observes a signal subtraction across high-precision reference resistors with values known to the code in the signal processor 1330. The signal processor 1330 uses arithmetic division of each sensor, reference element observation by its preceding (or following) reference resistor, reference resistor observation to cancel the transfer functions of all circuitry supplying the sinusoidal voltage or current signal upstream from the sensor and to cancel the transfer functions of all circuitry being used to observe the signals downstream from the sensor. This provides a phase-sensitive measurement that is also immune to variations in the circuitry for which the transfer functions have been cancelled. This immunity to variation is effective within a single unit over time, from one unit to the next, and from one system design revision to the next.

The amplitude-response of the circuitry supplying the applied field is dealt with separately from the signal processor 1330's division-based transfer function cancellation with a per-unit calibration to ensure the strength of the applied magnetic field is as intended. In the case the applied field is sinusoidal and not DC, this creates an amplitude modulation of the applied sinusoidal current or voltage carrier. In the presence of this amplitude modulation, the magnetoresistance appears in upper and lower sidebands. The phase response of the circuitry supplying the applied field appears in the sidebands, where the lower sideband is rotated by the negative of the phase of the applied field and the upper sideband is rotated by the positive of the phase of the applied field. This rotation from the field is cancelled by the code of the signal processor system 1330 by rotating the phases of the sidebands to their mean. Thus, the transfer function of the circuitry applying the field is fully accounted for, enabling a phase-sensitive and phase-accurate magnetoresistance measurement even when the applied field is AC. Importantly, the phase-sensitive and phase-accurate measurement allows for distinction between scenarios where magnetoresistance is decreasing from those where it is increasing. Without a phase-sensitive measurement, this can otherwise be difficult to discern.

The high precision reference resistors 2460 can be placed on either the cartridge reader 310 or the cartridge assembly 200. In either location, their logical function and connection is the same, but there is a cost-performance trade off to their physical placement. Placing the high precision reference resistors 2460 in proximity to the GMR sensors on the cartridge assembly 200 can theoretically improve performance through further cancellation of common artifacts. This can also allow matching of the reference resistors to their mating GMR sensors on a cartridge-by-cartridge basis. However, if the cartridge assembly 200 is very cost-sensitive and the cartridge assembly 200 is a higher-volume-production-item than the signal preparing unit 1540 of the cartridge reader 310, there is a cost advantage to placing the high precision reference resistors 2460 on the cartridge reader 310.

Similarly, the multiplexer(s) can be placed on the cartridge assembly 200, the cartridge reader 310, or both. The placement of the multiplexer(s) should be chosen to optimize system cost and performance, while constraining the design to a manageable number of connections between the cartridge assembly 200 and the cartridge reader 310 and yet supporting the desired number of addressable sensors in the system. In the design where multiplexers are placed on both the cartridge assembly 200 and the cartridge reader 310 and are all used together to address GMR sensors, many signals are run from the cartridge assembly 200 to on-reader multiplexers. A second layer of multiplexers on the cartridge assembly allow for bank switching. With this, the number of sensors that can be addressed is multiplied.

Observations of the GMR sensors and reference resistors are made by measuring currents through them or voltages across them in discrete time with the analog-to-digital converter 1910. The digital-to-analog converter 1910 generating the applied sinusoidal voltage or current and generating the applied field are clocked from the same source as the analog-to-digital converter 1980. The signal processor 1330 implements a lock-in amplifier in code that measures the correlation between the signals observed at the analog-to-digital converter 1980 and in-phase and quadrature (rotated 90 degrees) sinusoids generated internally at all frequencies of interest. The signals from the analog-to-digital converter 1980 are multiplied by the internal in-phase and quadrature sinusoids producing an in-phase product and a quadrature product for each sample at each frequency of interest. These products are accumulated through the duration of each observation.

In a time invariant system with an infinite duration of observation, for given circuit and sensor conditions, the ratio of the in-phase and quadrature accumulations will be fixed. The signal processor 1330 automatically selects generator frequencies and observation duration such that all signals of interest are at the same phase angle at the beginning and end of each observation. This allows the system to mimic the operation of a time invariant system, even with very short observation periods. The signal processor 1330 also starts sensor observations with all generator phase angles consistent from one observation to the next. This removes variability that could otherwise be introduced by differences in phase response and group delay of the circuits generating the applied sinusoidal current or voltage and the circuitry generating an applied field.

The GMR sensor measurement proceeds as follows. The signal processor 1330 configures the circuit for observation of the reference resistor structure by sending appropriate commands to the multiplexer 1950 which can be on the cartridge assembly 200 or on the cartridge reader 310 or both. The digital-to-analog converter 1910 is used to generate the applied sinusoidal voltage or current and the applied field. A minimum wait time is observed in order to allow transients from multiplexer switching to settle. After this minimum wait time, the signal processor 1330 begins accumulating the in-phase and quadrature products derived from the reference resistor signals observed at the analog-to-digital converter 1980. After an integer number of cycles have elapsed for all internal (and external) sine wave generators 2110, the integrator 2130 is frozen and captured. The numbers of elapsed cycles will be different at the various observation frequencies, but must all be integers. After initial capture of the integrator 2130, signal generation from the digital-to-analog generator 1910 continues while the signal processor 1330 commands the multiplexer 1950 to configure the circuit for observation of GMR sensor(s). A minimum wait time is observed in order to allow transients from multiplexer switching to settle. After this minimum wait time, the signal processor 1330 waits for all signal generators to arrive at a predefined phase angle. After arrival at the predefined phase angle, the signal processor 1330 begins accumulating the in-phase and quadrature products derived from the sensor signals observed at the analog-to-digital converter 1980. After integer numbers of cycles have elapsed for all internal (and external) sine wave generators 2110, the integrator 2130 is again frozen and captured. The signal processor 1330 divides the captured sensor accumulations by the captured reference accumulations and, with prior knowledge of the reference resistance values, uses the quotients to compute phase-accurate sensor resistance and magnetoresistance quantities that are not influenced by the frequency, amplitude or phase of the applied sinusoidal current or voltage, or by the amplitude or phase response of the circuits supplying this. The sensor resistance and magnetoresistance quantities are also not influenced by the frequency or phase angle of the applied field, and are not influenced by the phase response of the circuits supplying this. Thus, any of these elements can be freely modified, for instance to achieve optimal signal-to-noise ratio, without perturbation of the resistance and magnetoresistance telemetry.

As mentioned above, a GMR sensor is modeled as a resistance that changes in proportion to the total magnetic field. This resistance value may be expressed as $$R = Rn(1+kH),$$

where Rn is the nominal resistance of the GMR sensor with zero magnetic field applied to it, H is the total magnetic field, k is a property of the GMR sensor that relates the change in resistance to the total magnetic field, and R is the total resistance with inclusion of the change in resistance induced by the magnetic field.

A dimensionless quantity, magneto resistance (MR), is defined as a measure of the change in resistance of the GMR sensor. It is expressed as the total resistance in the presence of the magnetic field divided by the nominal resistance with zero field. Thus:

$$MR = Rn(1+kH)/Rn = 1+kH.$$

For those GMR sensors functionalized for the assay, magnetic nanoparticles become bound to the sensor surface, thus changing the total field, which will in turn change the magneto resistance. This change in MR, delta(MR), is what is ultimately observed, as this is a quantity directly related to the concentration of magnetic nanoparticles in close proximity to the functionalized sensor and can therefore be used to infer their presence and measure their concentration.

As shown in FIG. 24C, voltage divider sensor pairs are provided for the full bridge topology, where each pair comprises one sensor functionalized for the assay and one blocked sensor. Applying voltage across any of these voltage dividers, and assuming behavior of the functionalized and blocked sensors are otherwise identical, one can observe a voltage at the midpoint of each divider that changes solely due to the delta(MR) imparted by attachment of magnetic nanoparticles to the functionalized sensor. To the extent the other aspects of the sensors' behavior may be unstable over time, the arrangement of the otherwise identical sensors into voltage divider pairs also provides a mechanism for cancellation of the artifacts introduced by these changes over time (for instance, thermal changes).

As can be seen in FIG. 24C, the voltage divider sensor pairs may have one of two arrangements. The functionalized sensors (the black GMR1$a$, GMR2$b$ in FIG. 24C) may either be connected to the voltage source or to ground; the blocked sensors (the white GMR1$b$, GMR2$a$ in FIG. 24C) are adjacent. Although at least one multiplexer is shown in the topologies, actually, banks of freely configurable switches can be used such that multiple nodes can be routed in at the same time. By use of a freely configurable, multi-channel switch with drains (for example, drains A and B), one can connect the midpoint of any voltage divider to either the inverting or non-inverting input of an instrumentation amplifier.

For example, a meaningful delta(MR) measurement may be performed by connecting one or more dividers of one arrangement to drain A and one or more dividers of the other arrangement to drain B. Alternatively, the midpoints of dividers of like arrangement may be connected to drain A or B and the midpoint of a high-precision reference resistor divider pair (where reference resistors are designated RTX1$a$, RTX1$b$, RTX2$a$ and RTX2$b$ in FIG. 24C) may be connected to the other drain. Yet a third arrangement is to connect the midpoints of two high-precision reference resistor divider pairs, one to each drain. This third arrangement provides a means to measure characteristics of the circuitry external to the bridge.

As an example, the measurement of the topology shown in FIG. 24C may proceed as follows: prior to introduction of magnetic nanoparticles, all sensor dividers may be measured separately in bridges configured with a sensor divider's midpoint connected to one drain and a high-precision resistor divider's midpoint connected to the other. One can confirm resistive balance and magneto-resistive balance for each sensor divider individually. For dividers that are out of specification, one can quarantine individual dividers rather than entire bridges as would be necessary in designs where bridges are statically configured.

For the assay measurement itself, in some embodiments, any number of divider pair' midpoints may be connected to the drains simultaneously, so long as divider pairs' functionalized sensors are functionalized for the same target and the midpoints of dividers of like arrangement are connected to the same drain, with the midpoints of dividers of the other arrangement connected to the other drain. In other embodiments, since the differential voltage probe does not need to be biased away from 0 volts, midpoint(s) of one or more divider sensor pairs in Arrangement 1 (or 2) may be connected to one input, and midpoint(s) of one or more divider sensor pairs also in Arrangement 1 (or 2) to the other input of the voltage probe. The advantages are then two-fold: first, effective sensor area can be increased by routing in many dividers, and second, the voltage that appears at the differential probe is 0 until functionalized sensors change with respect to non-functionalized sensors. In other words, voltage only arises due to this difference, which means optimal gain staging and improved SNR.

It is advantageous to connect many voltage dividers simultaneously, as this can reduce noise and the coefficient of variation: for dividers connected simultaneously, their sensors then act as a single unit and combine the free layer volume, and magneto-resistive sensor noise drops off as one over the square root of the free layer volume. The coefficient of variation is reduced because the random distribution of magnetic nanoparticles will be better measured by a larger sensing area (and it is well known in the literature that magneto-resistive sensors detect nanoparticles differently based on the position of nanoparticles relative to the free layer).

In an example, a further refinement is carried out to ensure that the same number of divider pairs are connected to drain A as are connected to drain B. Connecting an equal number of dividers presents balanced impedances to the instrumentation amplifier's inverting and non-inverting inputs, and thus maximizes the instrumentation amplifier's common mode rejection ratio. However, the procedures and algorithms described in this example are equally valid for other examples wherein a mismatched number of dividers are connected to the two drains.

For the observation of sensor magnetoresistance, an AC voltage is connected to the configured bridge while an AC magnetic field is applied. Application of the AC field modulates the sensors' resistances via the magneto-resistive effect. With attachment of magnetic nanoparticles to sensors functionalized for the assay, the sensor voltage dividers become unbalanced in a way that's predictably related to delta(MR). This in turn presents an amplitude-modulated voltage across the instrumentation amplifier with upper and lower sideband components related to delta(MR).

The analog-to-digital converter 1980 is connected to the output of the instrumentation amplifier 1970. The analog-to-digital converter 1980's output is collected by the signal processing unit 1550. Internal to the signal processing unit 1550, in-phase and quadrature (rotated 90 degrees) sinusoids are generated at the frequency of the carrier voltage applied to the bridge and at the frequencies of the sideband voltages arising from the amplitude modulation of the carrier. Correlations between the internal in-phase and quadrature signals and the signals observed at the analog-to-digital converter 1980 are measured by evaluating the accumulated means of the products of the internally-generated signals and the samples observed at the output of the analog-to-digital converter 1980 over a course of time during which an integer number of cycles have elapsed at all three frequencies. The in-phase and quadrature correlations at each frequency are equivalent to the complex voltages observed at each frequency, normalized by multiplication with the transfer functions of the circuitry and logic external to the bridge.

Immediately before or after each sensor bridge observation, an observation of the high-precision reference resistor bridge is performed. In order to create a non-zero voltage across the reference resistor bridge, one or more reference resistors 1955 must be mismatched from the others. In the arithmetic presented here, one resistor may be mismatched from the others, and the other three may be of equal value.

Because the reference resistor bridge is insensitive to the field, no amplitude-modulated sidebands voltages will appear across it. Instead, voltages at the carrier and two sideband frequencies generated, added and applied together directly to the reference resistor bridge. As with the sensor bridge observation, the complex voltages at the three frequencies are measured by multiplication by internally generated in-phase and quadrature sinusoids. The mean correlations are here also accumulated over a period of time during which an integer number of cycles have elapsed at all three frequencies. The observed complex voltages across the reference resistor bridge at the three frequencies of interest are normalized by multiplication with the same transfer functions as appear in the sensor voltages.

For a solution to delta(MR) from these six voltages, three observed across the sensor bridge and three observed at the same frequencies across the reference resistor bridge, the model of magnetoresistance, $R=R_n(1+kH)$, is decomposed into a first-order Taylor approximation where the constant term describes the relation between the observed sensor bridge voltage at the carrier frequency and the second term, proportional to H, describes the relation between the sensor bridge voltage observed at the two sidebands and all of $R_n$, $k$ and H.

A division by the voltages observed across the reference resistor bridge can lead to direct, phase-sensitive solutions for the components of delta(MR) appearing at the lower and upper sidebands as follows:

$$\text{delta}(MR,\text{lower}) = (4*(RTX'-RTX)*(RTX+RTX')*v_s(\text{lower})*v_{rx}(\text{carrier})*v_{rx}(\text{carrier}))/((RTX'-RTX)*(RTX'-RTX)*v_s(\text{carrier})*v_s(\text{carrier})*v_{rx}(\text{lower}) - 4*(RTX+RTX')*(RTX+RTX')*v_{rx}(\text{lower})*v_{rx}(\text{carrier})*v_{rx}(\text{carrier}))$$

$$\text{delta}(MR,\text{upper}) = (4*(RTX'-RTX)*(RTX+RTX')*v_s(\text{upper})*v_{rx}(\text{carrier})*v_{rx}(\text{carrier}))/((RTX'-RTX)*(RTX'-RTX)*v_s(\text{carrier})*v_s(\text{carrier})*v_{rx}(\text{upper}) - 4*(RTX+RTX')*(RTX+RTX')*v_{rx}(\text{upper})*v_{rx}(\text{carrier})*v_{rx}(\text{carrier}))$$

In the above equations, variables are defined as:
delta(MR, lower): a complex quantity; the component of delta-MR observed from the lower sideband voltage
delta(MR, upper): a complex quantity; the component of delta-MR observed from the upper sideband voltage
RTX: the value of the three matched resistors in the reference resistor bridge
RTX': the value of a fourth, mis-matched resistor in the reference resistor bridge
$v_s$(carrier): the complex voltage at the carrier frequency observed across the sensor bridge
$v_s$(lower): the complex voltage at the lower sideband frequency observed across the sensor bridge
$v_s$(upper): the complex voltage at the upper sideband frequency observed across the sensor bridge
$v_{rx}$(carrier): the complex voltage at the carrier frequency observed across the reference resistor bridge
$v_{rx}$(lower): the complex voltage at the lower sideband frequency observed across the reference resistor bridge
$v_{rx}$(upper): the complex voltage at the upper sideband frequency observed across the reference resistor bridge By virtue of the reference resistor voltage division, transfer functions of the circuitry external to the sensor bridge are largely canceled. The only remaining step to obtaining a phase-sensitive and phase-accurate measurement of delta (MR) is to cancel the phase angle of the applied AC magnetic field, by which both delta(MR, lower) and delta (MR, upper) are rotated, one negatively and one positively. It is known that MR is purely resistive, and so the components of delta(MR) appearing at the various frequencies should all be the same and should all be strictly real. Therefore, the rotation of delta(MR) by the phase offset of the applied field can be canceled by computing the mean of the apparent phase angles of delta(MR, lower) and delta (MR, upper). This will be approximately 0 for positive delta(MR) and approximately 180 degrees for negative delta(MR). That is, delta(MR) appears on the real axis. The apparent deviation of delta(MR) from the real axis can be minimized by balanced placement of parasitic elements on each side of the bridge. With such balanced placement (for instance, by use of a single multi-channel switch for configuration of both sides of the bridge), the apparent deviation of delta(MR) from the real axis can be minimized, often to the system's noise floor.

The magnitude of delta(MR) may be computed simply as the sum of the magnitudes of delta(MR, lower) and delta (MR, upper). Taking then the real component of this computed delta(MR), a phase-sensitive and phase-accurate (i.e. real) notion of magnetoresistance is realized in a single, dimensionless quantity which may be negative or positive, and may cross zero freely without perturbation. This delta (MR) is also immune to a large collection of possible variations in external circuitry, as well as non-MR variations in the sensors themselves.

In GMR detection systems according to prior art, the GMR-depended voltage magnitudes were used directly without calculating the phase. This works to some degree, but has disadvantages relative to the design described above. In contrast, the present disclosure has the following advantages:

- constant runtime calibration of circuitry for which there is transfer function cancellation;
- immunity to variation over time in these circuits with respect to things like temperature;
- very good unit-to-unit consistency for aspects of system operation related to these circuits without any particular additional effort on our part;
- ability to freely optimize design for performance without disturbance of output telemetry, which streamlines R&D;
- phase sensitivity, which means one always retains the ability to discern cases where magnetoresistance is increasing from case where magnetoresistance is decreasing.

In accordance with embodiments herein, there is provided a signal processing system used for GMR-based detection of a target analyte in a sample under test. The system comprises: a measurement circuit configuration unit configured to build a GMR sensor measurement circuit by routing in at least one GMR sensor, and to build a reference resistor measurement circuit by routing in at least one reference resistor; a magnetic field excitation unit configured to apply an AC magnetic field of frequency $\omega 2$ to the at least one GMR sensor; a carrier signal applying unit configured to apply a carrier signal of frequency $\omega 1$ to the GMR sensor measurement circuit, and apply carrier signals of frequency $\omega 1$, $\omega 1+\omega 2$, and $\omega 1-\omega 2$ to the reference resistor measurement circuit; a measurement signal pick-up unit coupled to the measurement circuits, configured to collect reference resistor measurement signals from the reference resistor measurement circuit and GMR sensor measurement signals from the GMR sensor measurement circuit; and a phase sensitive solution unit coupled to the measurement signal pick-up unit, configured to analytically solve for resistance change of the at least one GMR sensor based on both the reference resistor measurement signals from the reference resistor measurement circuit and the GMR sensor measurement signals from the GMR sensor measurement circuit.

In some embodiments, the phase sensitive solution unit comprises: reference signal generators, configured to generate in-phase and quadrature sinusoid reference signals at all frequencies of interest; a multiplier, configured to multiply the measurement signals by the reference signals to produce in-phase products and quadrature products at all frequencies of interest for each of the reference resistor measurement signals and the GMR sensor measurement signals; an integrator, configured to accumulate the in-phase products and quadrature products at all frequencies of interest for each of the reference resistor measurement signals and the GMR sensor measurement signals; and a close-form solver, configured to solve for the resistance change of the GMR sensor from the accumulations of the in-phase products and quadrature products at all frequencies of interest for each of the reference resistor measurement signals and the GMR sensor measurement signals. In some embodiments, the frequencies of interest are $\omega 1$, $\omega 1+\omega 2$, and $\omega 1-\omega 2$.

In some embodiments, the phase sensitive solution unit is further configured to solve for magnetoresistance change of the at least one GMR sensor. In some embodiments, the signal processing system comprises a detection result determination unit which is configured to determine, from the solved magnetoresistance change of the at least one GMR sensor, presence or not of the target analyte in the sample under test. In some embodiments, the signal processing system further comprises a detection result determination unit which is configured to determine, from the solved magnetoresistance change of the at least one GMR sensor, concentration of the target analyte in the sample under test.

In some embodiments, the carrier signal applying unit is a carrier current source which is configured to apply a carrier current to the measurement circuits, wherein the reference resistor measurement circuit is formed by a reference resistor connected in series between the carrier current source and ground, wherein the GMR sensor measurement circuit is formed by a GMR sensor connected in series between the carrier current source and ground, or by a parallel combination of more than one GMR sensor which is connected in series between the carrier current source and ground, and wherein the GMR sensor is functionalized for the target analyte.

In some embodiments, the carrier signal applying unit is a carrier voltage source which is configured to apply a carrier voltage to the measurement circuits, wherein the GMR sensor measurement circuit is a Wheatstone full bridge circuit formed by a first bridge arm and a second bridge arm, wherein the first bridge arm comprises one first voltage divider or a parallel combination of more than one first voltage divider, wherein the first voltage divider is formed by a GMR sensor functionalized for the target analyte and a reference element, wherein the second bridge arm comprises one second voltage divider or a parallel combination of more than one second voltage divider, wherein the second voltage divider formed by a GMR sensor functionalized for the target analyte and a reference element, wherein the functionalized GMR sensor in the first voltage divider is connected to the carrier voltage source while the reference element in the first voltage divider is connected to ground, and wherein the functionalized GMR sensor in the second voltage divider is connected to ground while the reference element in the second voltage divider is connected to the carrier voltage source.

In some embodiments, the carrier signal applying unit is a carrier voltage source which is configured to apply a carrier voltage to the measurement circuits, wherein the GMR sensor measurement circuit is a Wheatstone full bridge circuit formed by a first bridge arm and a second bridge arm, wherein the first bridge arm comprises one first voltage divider or a parallel combination of more than one first voltage divider, wherein the first voltage divider is formed by a GMR sensor functionalized for the target analyte and a reference element, wherein the second bridge arm comprises one second voltage divider or a parallel combination of more than one second voltage divider, wherein the second voltage divider is formed by a GMR sensor functionalized for the target analyte and a reference element, wherein the functionalized GMR sensor in the first voltage divider is connected to the carrier voltage source while the reference element in the first voltage divider is connected to ground, and wherein the functionalized GMR sensor in the second voltage divider is connected to the carrier voltage source while the reference element in the second voltage divider is connected to ground.

In some embodiments, the reference resistor measurement circuit is a Wheatstone full bridge circuit formed by four reference resistors, wherein three of the four reference resistors have matched resistance value, and wherein the fourth reference resistor has a mis-matched resistance value.

In some embodiments, the carrier signal applying unit is a carrier current source which is configured to apply a carrier current to the measurement circuits, wherein the reference resistor measurement circuit are an Anderson loop circuit comprised of a reference resistor voltage divider formed of two reference resistors, wherein the GMR sensor measurement circuit are an Anderson loop circuit comprised of one GMR sensor voltage divider or a parallel combination of more than one GMR sensor voltage divider, and wherein the GMR sensor voltage divider is formed of a GMR sensor functionalized for the target analyte and a reference element.

In some embodiments, the reference element is a GMR sensor un-functionalized to the analyte to be detected.

In some embodiments, the reference element is a reference resistor.

In some embodiments, the measurement circuit configuration unit comprises at least one multiplexer.

In some embodiments, the measurement circuit configuration unit comprises a bank of freely configurable switches.

In some embodiments, a buffer is coupled between the carrier signal applying unit and the measurement circuits, making the carrier signal applying unit present a low impedance output relative to the measurement circuits.

In some embodiments, the measurement signal pick-up unit comprises a differential amplifier and an A/D converter, wherein the differential amplifier is coupled to the measurement circuits, and is configured to differentially amplify the measurement signals from the measurement circuits, and wherein the A/D converter is coupled to the differential amplifier and is configured to convert the amplified measurement signals from analog signals to digital signals.

In some embodiments, a buffer is coupled between the measurement circuits and the differential amplifier, making the measurement circuits present a high impedance output relative to the differential amplifier.

In accordance with embodiments, a signal processing method is used for GMR-based detection of a target analyte in a sample under test, comprising: obtaining GMR sensor measurement signals, which comprises: building a GMR sensor measurement circuit by routing in at least one GMR sensor, applying a carrier signal of frequency $\omega 1$ to the GMR sensor measurement circuit, applying an AC magnetic field of frequency $\omega 2$ to the at least one GMR sensor, and collecting the GMR sensor measurement signals from the GMR sensor measurement circuit; obtaining reference resistor measurement signals, which comprises: building a reference resistor measurement circuit by routing in at least one reference resistor, applying carrier signals of frequency $\omega 1$, $\omega 1+\omega 2$, and $\omega 1-\omega 2$ to the reference resistor measurement circuit, and collecting the reference resistor measurement signals from the reference resistor measurement circuit; and analytically solving for resistance change of the at least one GMR sensor based on both the reference resistor measurement signals from the reference resistor measurement circuit and the GMR sensor measurement signals from the GMR sensor measurement circuit.

In some embodiments, the method comprises obtaining the reference resistor measurement signals precedes to obtaining the GMR sensor measurement signals.

In some embodiments, analytically solving for resistance change of the at least one GMR sensor comprises: generating in-phase and quadrature sinusoid reference signals at all frequencies of interest; multiplying the measurement signals by the reference signals to produce in-phase products and quadrature products at all frequencies of interest for each of the reference resistor measurement signals and the GMR sensor measurement signals; accumulating the in-phase products and quadrature products at all frequencies of interest for each of the reference resistor measurement signals and the GMR sensor measurement signals; and solving for the resistance change of the GMR sensor from the accumulations of the in-phase products and quadrature products at all frequencies of interest for each of the reference resistor measurement signals and the GMR sensor measurement signals. In some embodiments, the frequencies of interest are $\omega 1$, $\omega 1+\omega 2$, and $\omega 1-\omega 2$.

In some embodiments, analytically solving for resistance change of the at least one GMR sensor further comprises solving for magnetoresistance change of the at least one GMR sensor. In some embodiments, the method comprises: determining, from the solved magnetoresistance change of the at least one GMR sensor, presence or not of the target analyte in the sample under test.

In some embodiments, the method comprises determining, from the solved magnetoresistance change of the at least one GMR sensor, concentration of the target analyte in the sample under test.

In some embodiments, applying the carrier signal to the measurement circuits comprises applying a carrier current to the measurement circuits using a carrier current source, wherein building the reference resistor measurement circuit comprising connecting a reference resistor in series between the carrier current source and ground, wherein building the GMR sensor measurement circuit comprising connecting a GMR sensor in series between the carrier current source and ground, or connecting a parallel combination of more than one GMR sensor in series between the carrier current source and ground, and wherein the GMR sensor is functionalized for the target analyte.

In some embodiments, applying the carrier signal to the measurement circuits comprises applying a carrier voltage to the measurement circuits using a carrier voltage source, wherein building the GMR sensor measurement circuit comprises building a Wheatstone full bridge circuit formed by a first bridge arm and a second bridge arm, wherein the first bridge arm comprises one first voltage divider or a parallel combination of more than one first voltage divider, wherein the first voltage divider is formed by a GMR sensor functionalized for the target analyte and a reference element, wherein the second bridge arm comprises one second voltage divider or a parallel combination of more than one second voltage divider, wherein the second voltage divider is formed by a GMR sensor functionalized for the target analyte and a reference element, wherein the functionalized GMR sensor in the first voltage divider is connected to the carrier voltage source while the reference element in the first voltage divider is connected to ground, and wherein the functionalized GMR sensor in the second voltage divider is connected to ground while the reference element in the second voltage divider is connected to the carrier voltage source.

In some embodiments, applying the carrier signal to the measurement circuits comprises applying a carrier voltage to the measurement circuits using a carrier voltage source, wherein building the GMR sensor measurement circuit comprises building a Wheatstone full bridge circuit formed by a first bridge arm and a second bridge arm, wherein the first bridge arm comprises one first voltage divider or a parallel combination of more than one first voltage divider, wherein the first voltage divider is formed by a GMR sensor functionalized for the target analyte and a reference element, wherein the second bridge arm comprises one second voltage divider or a parallel combination of more than one second voltage divider, wherein the second voltage divider is formed by a GMR sensor functionalized for the target analyte and a reference element, wherein the functionalized GMR sensor in the first voltage divider is connected to the carrier voltage source while the reference element in the first voltage divider is connected to ground, and wherein the functionalized GMR sensor in the second voltage divider is connected to the carrier voltage source while the reference element in the second voltage divider is connected to ground.

In some embodiments, building the reference resistor measurement circuit comprises building a Wheatstone full bridge circuit formed by four reference resistors, wherein three of the four reference resistors have matched resistance value, and wherein the fourth reference resistor has a mismatched resistance value.

In some embodiments, applying the carrier signal to the measurement circuits comprises applying a carrier voltage to the measurement circuits using a carrier voltage source, wherein building the reference resistor measurement circuit comprises building an Anderson loop circuit comprised of a reference resistor voltage divider formed of two reference resistors, wherein building the GMR sensor measurement circuit comprises building an Anderson loop circuit comprised of one GMR sensor voltage divider or a parallel combination of more than one GMR sensor voltage divider, and wherein the GMR sensor voltage divider is formed of a GMR sensor functionalized for the target analyte and a reference element.

In some embodiments, the reference element in the method is a GMR sensor un-functionalized to the analyte to be detected.

In some embodiments, the reference element in the method is a reference resistor.

In some embodiments, building the measurement circuits comprises configuring at least one multiplexer.

In some embodiments, building the measurement circuits comprises configuring a bank of freely configurable switches.

In some embodiments, collecting measurement signals at the measurement circuits comprises: differentially amplifying the measurement signals at the measurement circuits, and converting the amplified measurement signals from analog signals to digital signals.

While the principles of the disclosure have been made clear in the illustrative embodiments set forth above, it will be apparent to those skilled in the art that various modifications may be made to the structure, arrangement, proportion, elements, materials, and components used in the practice of the disclosure.

It will thus be seen that the features of this disclosure have been fully and effectively accomplished. It will be realized, however, that the foregoing preferred specific embodiments have been shown and described for the purpose of illustrating the functional and structural principles of this disclosure and are subject to change without departure from such principles. Therefore, this disclosure includes all modifications encompassed within the spirit and scope of the following claims.

What is claimed is:

1. A signal processing system used for Giant Magneto-Resistive (GMR)-based detection of a target analyte in a sample under test, comprising:
   a measurement circuit configuration unit configured to build a GMR sensor measurement circuit by routing in at least one GMR sensor, and to build a reference resistor measurement circuit by routing in at least one reference resistor, the GMR sensor measurement circuit comprising at least one GMR sensor voltage divider, and the reference resistor measurement circuit comprising at least one reference resistor voltage divider;
   a magnetic field excitation unit configured to apply an Alternating Current (AC) magnetic field of frequency $\omega_2$ to the at least one GMR sensor;
   a carrier signal applying unit configured to apply a carrier signal of frequency $\omega_1$ to the GMR sensor measurement circuit, and apply carrier signals of frequency $\omega_1$, and $\omega_1+\omega_2$, and $\omega_1-\omega_2$ to the reference resistor measurement circuit;
   a measurement signal pick-up unit coupled to the measurement circuits, configured to collect reference resistor measurement signals from the reference resistor measurement circuit and GMR sensor measurement signals from the GMR sensor measurement circuit; and
   a phase sensitive solution unit coupled to the measurement signal pick-up unit, configured to analytically solve for resistance change of the at least one GMR sensor based on both the reference resistor measurement signals from the reference resistor measurement circuit and the GMR sensor measurement signals from the GMR sensor measurement circuit.

2. The signal processing system according to claim 1, wherein the phase sensitive solution unit comprises:
   reference signal generators, configured to generate in-phase and quadrature sinusoid reference signals at all frequencies of interest;
   a multiplier, configured to multiply the measurement signals by the reference signals to produce in-phase products and quadrature products at all frequencies of interest for each of the reference resistor measurement signals and the GMR sensor measurement signals;
   an integrator, configured to accumulate the in-phase products and quadrature products at all frequencies of interest for each of the reference resistor measurement signals and the GMR sensor measurement signals; and
   a close-form solver, configured to solve for the resistance change of the GMR sensor from the accumulations of the in-phase products and quadrature products at all frequencies of interest for each of the reference resistor measurement signals and the GMR sensor measurement signals.

3. The signal processing system according to claim 1, wherein the phase sensitive solution unit is further configured to solve for magnetoresistance change of the at least one GMR sensor.

4. The signal processing system according to claim 3, wherein the signal processing system comprises a detection result determination unit which is configured to determine, from the solved magnetoresistance change of the at least one GMR sensor, presence or not of the target analyte in the sample under test and/or concentration of the target analyte in the sample under test.

5. The signal processing system according to claim 1, wherein the carrier signal applying unit is a carrier current source which is configured to apply a carrier current to the measurement circuits,
wherein the reference resistor measurement circuit is formed by a reference resistor connected in series between the carrier current source and ground,
wherein the GMR sensor measurement circuit is formed by a GMR sensor connected in series between the carrier current source and ground, or by a parallel combination of more than one GMR sensor which is connected in series between the carrier current source and ground, and
wherein the GMR sensor is functionalized for the target analyte.

6. The signal processing system according to claim 1, wherein the carrier signal applying unit is a carrier voltage source which is configured to apply a carrier voltage to the measurement circuits,
wherein the GMR sensor measurement circuit is a Wheatstone full bridge circuit formed by a first bridge arm and a second bridge arm,
wherein the first bridge arm comprises one first voltage divider or a parallel combination of more than one first voltage divider,
wherein the first voltage divider is formed by a GMR sensor functionalized for the target analyte and a reference element,
wherein the second bridge arm comprises one second voltage divider or a parallel combination of more than one second voltage divider,
wherein the second voltage divider formed by a GMR sensor functionalized for the target analyte and a reference element,
wherein the functionalized GMR sensor in the first voltage divider is connected to the carrier voltage source while the reference element in the first voltage divider is connected to ground, and
wherein the functionalized GMR sensor in the second voltage divider is connected to ground while the reference element in the second voltage divider is connected to the carrier voltage source.

7. The signal processing system according to claim 6, wherein the reference resistor measurement circuit is a Wheatstone full bridge circuit formed by four reference resistors,
wherein three of the four reference resistors have matched resistance value, and
wherein the fourth reference resistor has a mis-matched resistance value.

8. The signal processing system according to claim 6, wherein the reference element is a GMR sensor un-functionalized to the analyte to be detected, or a reference resistor.

9. The signal processing system according to claim 1, wherein the carrier signal applying unit is a carrier voltage source which is configured to apply a carrier voltage to the measurement circuits,
wherein the GMR sensor measurement circuit is a Wheatstone full bridge circuit formed by a first bridge arm and a second bridge arm,
wherein the first bridge arm comprises one first voltage divider or a parallel combination of more than one first voltage divider,
wherein the first voltage divider is formed by a GMR sensor functionalized for the target analyte and a reference element,
wherein the second bridge arm comprises one second voltage divider or a parallel combination of more than one second voltage divider,
wherein the second voltage divider is formed by a GMR sensor functionalized for the target analyte and a reference element,
wherein the functionalized GMR sensor in the first voltage divider is connected to the carrier voltage source while the reference element in the first voltage divider is connected to ground, and
wherein the functionalized GMR sensor in the second voltage divider is connected to the carrier voltage source while the reference element in the second voltage divider is connected to ground.

10. The signal processing system according to claim 1, wherein the carrier signal applying unit is a carrier current source which is configured to apply a carrier current to the measurement circuits,
wherein the reference resistor measurement circuit comprises an Anderson loop circuit,
wherein the GMR sensor measurement circuit comprises an Anderson loop circuit, and
wherein the GMR sensor voltage divider is formed of a GMR sensor functionalized for the target analyte and a reference element.

11. The signal processing system according to claim 1, wherein the measurement circuit configuration unit comprises at least one multiplexer, or a bank of freely configurable switches.

12. The signal processing system according to claim 1, wherein a buffer is coupled between the carrier signal applying unit and the measurement circuits, making the carrier signal applying unit present a low impedance output relative to the measurement circuits.

13. The signal processing system according to claim 1, wherein a buffer is coupled between the measurement circuits and a differential amplifier, making the measurement circuits present a high impedance output relative to the differential amplifier.

14. A signal processing method used for Giant Magneto-Resistive (GMR)-based detection of a target analyte in a sample under test, comprising:
obtaining GMR sensor measurement signals, which comprises
building a GMR sensor measurement circuit by routing in at least one GMR sensor, the GMR sensor measurement circuit comprising at least one GMR sensor voltage divider,
applying a carrier signal of frequency $\omega_1$ to the GMR sensor measurement circuit,
applying an Alternating Current (AC) magnetic field of frequency $\omega_2$ to the at least one GMR sensor, and
collecting the GMR sensor measurement signals from the GMR sensor measurement circuit;
obtaining reference resistor measurement signals, which comprises:
building a reference resistor measurement circuit by routing in at least one reference resistor, the reference resistor measurement circuit comprising at least one reference resistor voltage divider, applying carrier signals of frequency $\omega_1$, $\omega_1+\omega_2$, and $\omega_1-\omega_2$ to the reference resistor measurement circuit, and collecting the reference resistor measurement signals from the reference resistor measurement circuit; and analytically solving for resistance change of the at least one GMR sensor based on both the reference resistor measurement signals from the reference resistor measurement circuit and the GMR sensor measurement signals from the GMR sensor measurement circuit.

15. The signal processing method according to claim 14, wherein analytically solving for resistance change of the at least one GMR sensor comprises:

generating in-phase and quadrature sinusoid reference signals at all frequencies of interest;

multiplying the measurement signals by the reference signals to produce in-phase products and quadrature products at all frequencies of interest for each of the reference resistor measurement signals and the GMR sensor measurement signals;

accumulating the in-phase products and quadrature products at all frequencies of interest for each of the reference resistor measurement signals and the GMR sensor measurement signals; and solving for the resistance change of the GMR sensor from the accumulations of the in-phase products and quadrature products at all frequencies of interest for each of the reference resistor measurement signals and the GMR sensor measurement signals.

16. The signal processing method according to claim 14, wherein analytically solving for resistance change of the at least one GMR sensor further comprises solving for magnetoresistance change of the at least one GMR sensor.

17. The signal processing method according to claim 16, further comprising:

determining, from the solved magnetoresistance change of the at least one GMR sensor, presence or not of the target analyte in the sample under test and/or concentration of the target analyte in the sample under test.

18. The signal processing method according to claim 14, wherein applying the AC carrier signal to the measurement circuits comprises applying a carrier current to the measurement circuits using a carrier current source, wherein building the reference resistor measurement circuit comprising connecting a reference resistor in series between the carrier current source and ground, wherein building the GMR sensor measurement circuit comprising connecting a GMR sensor in series between the carrier current source and ground, or connecting a parallel combination of more than one GMR sensor in series between the carrier current source and ground, and wherein the GMR sensor is functionalized for the target analyte.

19. The signal processing method according to claim 14, wherein applying the carrier signal to the measurement circuits comprises applying a carrier voltage to the measurement circuits using a carrier voltage source, wherein building the GMR sensor measurement circuit comprises building a Wheatstone full bridge circuit formed by a first bridge arm and a second bridge arm, wherein the first bridge arm comprises one first voltage divider or a parallel combination of more than one first voltage divider, wherein the first voltage divider is formed by a GMR sensor functionalized for the target analyte and a reference element, wherein the second bridge arm comprises one second voltage divider or a parallel combination of more than one second voltage divider, wherein the second voltage divider is formed by a GMR sensor functionalized for the target analyte and a reference element, wherein the functionalized GMR sensor in the first voltage divider is connected to the carrier voltage source while the reference element in the first voltage divider is connected to ground, and wherein the functionalized GMR sensor in the second voltage divider is connected to ground while the reference element in the second voltage divider is connected to the carrier voltage source.

20. The signal processing method according to claim 19, wherein building the reference resistor measurement circuit comprises building a Wheatstone full bridge circuit formed by four reference resistors, wherein three of the four reference resistors have matched resistance value, and wherein the fourth reference resistor has a mis-matched resistance value.

21. The signal processing method according to claim 19, wherein the reference element is a reference resistor.

22. The signal processing method according to claim 14, wherein applying the carrier signal to the measurement circuits comprises applying a carrier voltage to the measurement circuits using a carrier voltage source, wherein building the GMR sensor measurement circuit comprises building a Wheatstone full bridge circuit formed by a first bridge arm and a second bridge arm, wherein the first bridge arm comprises one first voltage divider or a parallel combination of more than one first voltage divider, wherein the first voltage divider is formed by a GMR sensor functionalized for the target analyte and a reference element, wherein the second bridge arm comprises one second voltage divider or a parallel combination of more than one second voltage divider, wherein the second voltage divider is formed by a GMR sensor functionalized for the target analyte and a reference element, wherein the functionalized GMR sensor in the first voltage divider is connected to the carrier voltage source while the reference element in the first voltage divider is connected to ground, and wherein the functionalized GMR sensor in the second voltage divider is connected to the carrier voltage source while the reference element in the second voltage divider is connected to ground.

23. The signal processing method according to claim 14, wherein applying the carrier signal to the measurement circuits comprises applying a carrier voltage to the measurement circuits using a carrier voltage source, wherein building the reference resistor measurement circuit comprises building an Anderson loop circuit, wherein building the GMR sensor measurement circuit comprises building an Anderson loop circuit, and wherein the GMR sensor voltage divider is formed of a GMR sensor functionalized for the target analyte and a reference element.

24. The signal processing method according to claim 14, wherein building the measurement circuits comprises configuring at least one multiplexer, or a bank of freely configurable switches.

* * * * *